US007011814B2

(12) United States Patent
Suddarth et al.

(10) Patent No.: US 7,011,814 B2
(45) Date of Patent: Mar. 14, 2006

(54) SYSTEMS, METHODS AND DEVICES FOR IN VIVO MONITORING OF A LOCALIZED RESPONSE VIA A RADIOLABELED ANALYTE IN A SUBJECT

(75) Inventors: Steven Suddarth, Durham, NC (US); Charles W. Scarantino, Raleigh, NC (US); Robert D. Black, Chapel Hill, NC (US)

(73) Assignee: Sicel Technologies, Inc., Morrisville, NC (US)

( * ) Notice: Subject to any disclaimer, the term of this patent is extended or adjusted under 35 U.S.C. 154(b) by 349 days.

(21) Appl. No.: 10/127,207

(22) Filed: Apr. 22, 2002

(65) Prior Publication Data

US 2003/0012731 A1 Jan. 16, 2003

Related U.S. Application Data

(60) Provisional application No. 60/285,923, filed on Apr. 23, 2001.

(51) Int. Cl.
*A61K 51/00* (2006.01)
*A61K 49/00* (2006.01)

(52) U.S. Cl. ................. 424/9.2; 424/1.81; 600/300; 600/301

(58) Field of Classification Search ............ 424/9.2, 424/9.1, 1.81; 600/300, 301, 407, 326
See application file for complete search history.

(56) References Cited

U.S. PATENT DOCUMENTS

| | | | |
|---|---|---|---|
| 3,638,640 A | 2/1972 | Shaw | 128/2 R |
| 3,972,320 A | 8/1976 | Kalman | 128/2.1 A |
| 4,163,380 A | 8/1979 | Masoner | 72/342 |
| 4,326,535 A | 4/1982 | Steffel et al. | 128/631 |
| 4,361,153 A | 11/1982 | Slocum et al. | 128/419 P |
| 4,397,313 A | 8/1983 | Vaguine | 128/399 |
| 4,397,314 A | 8/1983 | Vaguine | 128/399 |
| 4,416,283 A | 11/1983 | Slocum | 128/419 PG |
| 4,431,004 A | 2/1984 | Bessman et al. | 128/635 |
| 4,484,076 A | 11/1984 | Thomson | |
| 4,494,545 A | 1/1985 | Slocum et al. | 128/1.5 |
| 4,519,401 A | 5/1985 | Ko et al. | 118/748 |
| 4,523,279 A | 6/1985 | Sperinde et al. | 364/416 |
| 4,541,901 A | 9/1985 | Parker et al. | 204/1 T |
| 4,543,953 A | 10/1985 | Slocum et al. | 128/419 PT |
| 4,556,063 A | 12/1985 | Thompson et al. | 128/419 PT |
| 4,571,292 A | 2/1986 | Liu et al. | 204/412 |
| 4,571,589 A | 2/1986 | Slocum et al. | 128/419 PG |
| 4,575,676 A | 3/1986 | Palkuti | 324/158 D |
| 4,625,733 A | 12/1986 | Säynäjäkangas | 128/687 |
| 4,638,436 A | 1/1987 | Badger et al. | 364/414 |
| RE32,361 E | 2/1987 | Duggan | 128/696 |
| 4,651,741 A | 3/1987 | Passafaro | 128/633 |
| 4,655,880 A | 4/1987 | Liu | 204/1 T |

(Continued)

FOREIGN PATENT DOCUMENTS

| | | |
|---|---|---|
| DE | 3219558 A1 | 12/1983 |
| DE | 33 32 075 | 3/1984 |
| DE | 4341903 A1 | 6/1995 |
| EP | 0 420 177 A1 | 4/1991 |
| EP | 0 471 957 A2 | 2/1992 |
| EP | 0537761 A2 | 4/1993 |
| EP | 0245073 B1 | 12/1993 |
| EP | 0386218 B1 | 1/1996 |
| GB | 2 263 196 A | 7/1993 |
| WO | WO95/17809 | 6/1995 |
| WO | WO 97/33513 | 9/1997 |
| WO | WO 98/02209 A2 | 1/1998 |
| WO | PCT/US98/05965 | 2/1998 |
| WO | WO 98/43701 | 10/1998 |
| WO | WO 98/58250 | 12/1998 |
| WO | WO 99/48419 | 9/1999 |
| WO | WO 99/58065 | 11/1999 |
| WO | WO 99/63881 | 12/1999 |
| WO | WO 00/29096 | 5/2000 |
| WO | WO00/18294 | 6/2000 |
| WO | WO 00/18294 | 6/2000 |
| WO | WO 00/40299 | 7/2000 |
| WO | WO02/39917 | 11/2000 |
| WO | WO 02/09775 | 2/2002 |
| WO | WO02/39918 | 5/2002 |
| WO | WO02/100485 | 6/2002 |

(Continued)

OTHER PUBLICATIONS

Alecu et al., *Dose perturbations due to in vivo dosimetry with diodes* Radiotherapy and Oncology, pp. 289–291, vol. 42, (1997).

Jornet et al., *Calibration of semiconductor detectors for dose assessment in total body irradiation*, Radiotherapy and Oncology, pp. 247–251, vol. 38, (1996).

Loncol et al., "Entrance and exit dose measurements with semiconductors and thermoluminescent dosemeters: a comparison of methods and in vivo results", Radiotherapy and Oncology, pp. 179–187, vol. 41, (1996).

Akin et al; "RF telemetry powering and control of hermetically sealed integrated sensors and actuators," Proc. Solid–State Sensors & Actuators Workshop, Hilton Head, SC, pp 145–148 (1990).

(Continued)

*Primary Examiner*—Michael Hartley
(74) *Attorney, Agent, or Firm*—Myers Bigel Sibley & Sajovec PA

(57) ABSTRACT

Methods, systems, devices and computer program products monitor in vivo detected radiation in a target localized site within a subject, over a selected time period, to do one or more of: (a) quantify a radiation dose received at a local site; (b) assess bioreceptiveness to a particular treatment time or type; (c) evaluate the pharmacokinetics of a radiolabeled analyte corresponding to a non-radiolabeled analyte; (d) monitor or evaluate metabolic activity; or (e) evaluate a tumor prior to or after a therapeutic treatment.

50 Claims, 24 Drawing Sheets

U.S. PATENT DOCUMENTS

| | | |
|---|---|---|
| 4,678,916 A | 7/1987 | Thomson .................... 250/370 |
| 4,681,111 A | 7/1987 | Silvian ................ 128/419 PT |
| 4,703,756 A | 11/1987 | Gough et al. ............... 128/635 |
| 4,719,919 A | 1/1988 | Marchosky et al. ........ 128/401 |
| 4,750,495 A | 6/1988 | Moore et al. ......... 128/419 PG |
| 4,769,547 A | 9/1988 | Uber, III .................... 250/374 |
| 4,793,825 A | 12/1988 | Benjamin et al. ........... 128/419 |
| 4,796,641 A | 1/1989 | Mills et al. ................. 128/748 |
| 4,804,847 A | 2/1989 | Uber, III ................ 250/370 F |
| 4,846,191 A | 7/1989 | Brockway et al. .......... 128/748 |
| 4,847,617 A | 7/1989 | Silvian .................. 340/970.16 |
| 4,900,422 A | 2/1990 | Bryan et al. ................. 204/401 |
| 4,919,141 A | 4/1990 | Zier et al. ................... 128/635 |
| 4,935,345 A | 6/1990 | Guilbeau et al. ............. 435/14 |
| 4,944,299 A | 7/1990 | Silvian ................. 128/419 PG |
| 4,958,645 A | 9/1990 | Cadell et al. ............... 128/903 |
| 4,961,422 A | 10/1990 | Marchosky et al. ........ 128/399 |
| 4,970,391 A | 11/1990 | Uber, III .................... 250/374 |
| 4,976,266 A | 12/1990 | Huffman et al. ............ 128/659 |
| 4,989,601 A | 2/1991 | Marchosky et al. ........ 128/399 |
| 5,008,546 A | 4/1991 | Mazziotta et al. .......... 250/366 |
| 5,012,411 A | 4/1991 | Policastro et al. ..... 364/413.06 |
| 5,098,547 A | 3/1992 | Bryan et al. ................. 204/401 |
| 5,109,850 A | 5/1992 | Blanco et al. .............. 128/635 |
| 5,117,113 A | 5/1992 | Thomson et al. |
| 5,117,824 A | 6/1992 | Keimel et al. ........ 128/419 PG |
| 5,126,937 A | 6/1992 | Yamaguchi et al. ... 364/413.11 |
| 5,127,404 A | 7/1992 | Wyborny et al. ........ 128/419 P |
| 5,137,022 A | 8/1992 | Henry .................. 128/419 PT |
| 5,159,262 A | 10/1992 | Rumbaugh et al. |
| 5,163,380 A | 11/1992 | Duffy et al. ................... 119/15 |
| 5,166,073 A | 11/1992 | Lefkowitz et al. ............. 436/57 |
| 5,186,172 A | 2/1993 | Fiddian-Green ............ 128/632 |
| 5,193,538 A | 3/1993 | Ekwall ................ 128/419 PT |
| 5,197,466 A | 3/1993 | Marchosky et al. ........ 128/399 |
| 5,205,294 A | 4/1993 | Flach et al. ................. 128/696 |
| 5,215,887 A | 6/1993 | Saito ............................ 435/14 |
| 5,264,843 A | 11/1993 | Silvian ........................ 340/870 |
| 5,309,085 A | 5/1994 | Sohn ........................ 324/71.5 |
| 5,314,450 A | 5/1994 | Thompson ................... 607/32 |
| 5,324,315 A | 6/1994 | Grevious ..................... 607/60 |
| 5,330,634 A | 7/1994 | Wong et al. ................. 204/409 |
| 5,354,314 A | 10/1994 | Hardy et al. ................ 128/653 |
| 5,354,319 A | 10/1994 | Wyborny et al. ............. 607/32 |
| 5,355,880 A | 10/1994 | Thomas et al. .............. 128/633 |
| 5,372,133 A | 12/1994 | Hogen Esch et al. ....... 128/631 |
| 5,383,909 A | 1/1995 | Keimel ........................... 607/5 |
| 5,425,361 A | 6/1995 | Fenzlein et al. ............ 128/635 |
| 5,431,171 A | 7/1995 | Harrison et al. ............ 128/698 |
| 5,444,254 A | 8/1995 | Thomson ............... 250/370.07 |
| 5,466,246 A | 11/1995 | Silvian ......................... 607/32 |
| 5,470,345 A | 11/1995 | Hassler et al. ................ 607/36 |
| 5,476,488 A | 12/1995 | Morgan et al. ............... 607/30 |
| 5,480,415 A | 1/1996 | Cox et al. ..................... 607/32 |
| 5,481,262 A | 1/1996 | Urbas et al. ........... 340/870.17 |
| 5,497,772 A | 3/1996 | Schulman et al. .......... 128/635 |
| 5,505,828 A | 4/1996 | Wong et al. ............. 205/777.5 |
| 5,507,786 A | 4/1996 | Morgan et al. ............... 607/27 |
| 5,517,313 A | 5/1996 | Colvin, Jr. .................. 356/417 |
| 5,535,752 A | 7/1996 | Halperin et al. ............ 128/670 |
| 5,538,005 A | 7/1996 | Harrison et al. ............ 128/698 |
| 5,545,187 A | 8/1996 | Bergstrom et al. ............ 607/31 |
| 5,549,113 A | 8/1996 | Halleck et al. .............. 128/633 |
| 5,549,654 A | 8/1996 | Powell ......................... 607/25 |
| 5,556,421 A | 9/1996 | Prutchi et al. ................ 607/36 |
| 5,557,702 A | 9/1996 | Yoshikawa et al. ......... 385/143 |
| 5,562,713 A | 10/1996 | Silvian ......................... 607/32 |
| 5,564,434 A | 10/1996 | Halperin et al. ............ 128/675 |
| 5,571,148 A | 11/1996 | Loeb et al. ................... 607/57 |
| 5,591,217 A | 1/1997 | Barreras ........................ 607/5 |
| 5,593,430 A | 1/1997 | Renger ........................... 607/9 |
| 5,596,199 A | 1/1997 | McNulty et al. |
| 5,606,163 A | 2/1997 | Huston et al. ............... 250/337 |
| 5,620,472 A | 4/1997 | Rahbari ....................... 128/903 |
| 5,620,475 A | 4/1997 | Magnusson ................... 607/30 |
| 5,620,479 A | 4/1997 | Diederich ..................... 607/97 |
| 5,626,630 A | 5/1997 | Markowitz et al. ........... 607/60 |
| 5,626,862 A | 5/1997 | Brem et al. ................. 424/426 |
| 5,628,324 A | 5/1997 | Sarbach ....................... 128/670 |
| 5,630,413 A | 5/1997 | Thomas et al. ............. 128/633 |
| 5,656,815 A | 8/1997 | Justus et al. ................. 250/337 |
| 5,681,611 A | 10/1997 | Yoshikawa et al. ....... 427/163.2 |
| 5,682,888 A | 11/1997 | Olson et al. .............. 128/653.1 |
| 5,720,771 A | 2/1998 | Snell ............................ 607/60 |
| 5,732,704 A | 3/1998 | Thurston et al. ............ 128/659 |
| 5,744,804 A | 4/1998 | Meijer et al. ................ 250/369 |
| 5,744,805 A | 4/1998 | Raylman et al. ........ 250/370.01 |
| 5,759,199 A | 6/1998 | Snell et al. ................... 607/60 |
| 5,791,344 A | 8/1998 | Schulman et al. ........... 128/635 |
| 5,811,814 A | 9/1998 | Leone et al. ................. 250/368 |
| 5,814,089 A | 9/1998 | Stokes et al. ................. 607/32 |
| 5,833,603 A | 11/1998 | Kovacs et al. .............. 600/317 |
| 5,840,148 A | 11/1998 | Campbell et al. ......... 156/275.5 |
| 5,857,463 A | 1/1999 | Thurston et al. ............ 128/659 |
| 5,879,375 A | 3/1999 | Larson et al. ................. 607/30 |
| 5,891,179 A | 4/1999 | Er et al. ........................ 607/27 |
| 5,916,167 A | 6/1999 | Kramer et al. .............. 600/436 |
| 5,918,110 A | 6/1999 | Abraham-Fuchs et al. .... 438/48 |
| 5,928,150 A | 7/1999 | Call ............................. 600/436 |
| 5,932,879 A | 8/1999 | Raylman et al. ........ 250/370.06 |
| 5,987,350 A | 11/1999 | Thurston ..................... 600/436 |
| 6,015,390 A | 1/2000 | Krag ........................... 600/549 |
| D423,377 S | 4/2000 | Atterbury et al. ............. D10/47 |
| 6,047,214 A | 4/2000 | Mueller et al. ............... 607/61 |
| D424,453 S | 5/2000 | Atterbury et al. ............. D10/47 |
| 6,076,009 A | 6/2000 | Raylman et al. ............ 600/436 |
| 6,087,666 A | 7/2000 | Huston et al. ............ 250/484.5 |
| 6,093,381 A | 7/2000 | Triozzi et al. .............. 424/1.49 |
| 6,099,821 A | 8/2000 | Rich et al. ................. 424/1.61 |
| 6,172,368 B1 | 1/2001 | Tarr et al. |
| 6,239,724 B1 | 5/2001 | Doron et al. |
| 6,240,312 B1 | 5/2001 | Alfano et al. ............... 600/476 |
| 6,242,741 B1 | 6/2001 | Miller et al. ........... 250/363.02 |
| 6,259,095 B1 | 7/2001 | Bouton et al. ............ 250/336.1 |
| 6,272,373 B1 | 8/2001 | Bouton ........................ 600/436 |
| 6,295,680 B1 | 10/2001 | Wahl et al. ...................... 14/1 |
| 6,363,940 B1 | 4/2002 | Krag ........................... 128/899 |
| 6,444,475 B1 | 9/2002 | Anderson, Jr. et al. ..... 436/161 |
| 6,614,025 B1 | 9/2003 | Thomson et al. |
| 6,650,930 B1 | 11/2003 | Ding ........................... 600/436 |

OTHER PUBLICATIONS

Akin, T., K. Najafi, R.M. Bradley, "An implantable multi-channel digital neural recording system for a micromachined sieve electrode," Proc. Int. Conf. on Solid–State Sensors and Actuators, Stockholm, Sweden, vol. 1, pp. 51–54. (Jun. 1995).

Barthe, Jean: "Electronic dosimeters based on solid state detectors," Nuclear. Instruments. and Methods in Physics Research Sec. B vol. 184, pp 158–189 (2001).

Berthold et al., "Method for in–situ detection of tritium in water," McDermott Technology Inc./RDTPA 99–03, pp. 1–9 (Sep. 19–22, 1999).

Biotelemetrics, Inc., 6520 Contempo Lane, Boca Raton, Florida 33433, Tel: 407-394-0315. Biotelemetry Page, http://speed.nimh.nih.gov/telemetry/classx.html, Feb. 1997.

Brochure, "Be as smart as you can be with BMDS and Smart Alec™ your partners in intelligence," Bio Medic Data Systems, Inc. (©1999).

Brochure, "Come along for the incredible journey in the development of the IPTT–200," Bio Medic Data Systems, Inc. (©2000).

Butson, Martin J. et al; "A new radiotherapy surface dose detector: The MOSFET," *Medical Physics, American Institute of Physics, vol. 23* (5) pp 655–658 (May 1996).

Cosofret et al., "Microfabricated sensor arrays sensitive to pH and K+ for ionic distribution measurements in the beating heart," *Analytical Chemistry*, vol. 67, pp. 1647–1653 (1995).

Data Sciences International, http://www.ispex.ca/companies/instrumentation/DataScInt.html, Profile web pp. 1–2 and Instrumental Products 1–7, Copyright Ispex Exchange Inc., 2003; for examination purposes, applicant admits similar devices were available prior to earlier filing date of application.

Deutsch, S., "Fifteen–electrode time–multiplex eeg telemetry from ambulatory patients," *IEEE Transactions on Biomedical Engineering*, vol. BME–26, pp. 153–159 (1979).

Dewhirst, "Concepts of oxygen transport at the microcirculatory level," *Seminars in Radiation Oncology*, vol. 8, 1998, pp. 143–150.

Dienes et al., *Radiation Effects in Solids, Interscience Monographs in Physics and Astronomy*, vol. II, Interscience Publishers, Inc., pp. 1–4; 56–85; 90–122 and 129–177 (©1957).

Fernald, "A microprocessor–based system for the fast prototyping of implantable instruments for biomedical research applications", Doctoral Dissertation, Elect. & Computer Eng., NC State Univ., (1992).

Fernald, K., T. Cook, T. Miller, III, J. Paulos, "A microprocessor–based implantable telemetry systems," *Computer*, vol. 24, No. 7, pp. 23–30 (1991).

Fryer, T., H. Sndler, W. Freund, E. McCutcheon, E. Carlson, "A multichannel implantable telemetry system for flow, pressure, and ECG measurements," *Jour. of Applied Physiology*, vol. 39, pp. 318–326 (1973).

Gerweck, "Tumor pH: Implications for Treatment and Novel Drug Design," 8 Seminars in Radiation Oncology, No. 5, pp. 176–182 (Jul. 1998).

Gilligan et al. , "Evaluation of a subcutaneous glucose sensor out to 3 months in a dog model," *Diabetes Care*, vol. 17, pp. 882–887 (1994).

Griffiths et al., "The OxyLite: a fibre–optic oxygen sensor," British J. of Radiology, vol. 72 pp. 627–630 (1999).

Gschwend, S., J. Knutti, H. Allen, J. Meindl, "A general–purpose implantable multichannel telemetry system for physiological research," *Biotelemetry Patient Monitoring*, vol. 6, pp. 107–117 (1979).

Hansen, B., K. Aabo, J. Bojsen, "An implantable, externally powered radiotelemetric system for long–term ECG and heart–rate monitoring," *Biotelemetry Patient Monitoring*, vol. 9., pp. 228–237 (1982).

Hines, "Advanced Biotelemetry Systems for Space Life Sciences: PH Telemetry," Biotelemetry XIII, Mar. 26–31, pp 131–137 (1995).

Holmstrom, N., P. Nilsson, J. Carlsten, S. Bowald, "Long–term in vivo experience of an electrochemical sensor using the potential step technique for measurement of mixed venous oxygen pressure," *Biosensors & Bioelectronics* 13, pp. 1287–1295 (1998).

Konigsberg Instruments, Inc., http://guide.labanimal.com/guide/companyd jsp?b=3930, Lab Animal p. 1, Product Categories p. 1, Lab Animal Buyers Guide 2003 p. 1 and Animal Research Equipment pp 1–12, Nature Publishing Group, 2003; for examination purposes, applicant admits similar devices were available prior to earlier filing date of application.

Lambrechts, M., Sansen, W., *Biosensors: Microelectrochemical Device*, NY, NY: IOP Publishing Ltd., pp. 206–208 (1992).

Lowe, S., et al., "p53 status and the efficacy of cancer therapy in vivo," *Sci.,* vol. 266, pp. 807–810 (1994).

Mackay, "Bio–Medical Telemetry, Sensing and Transmitting Biological Information from Animals and Man" Second edition, New York, NY: IEEE Press (1993).

Marzouk et al., "Electrodeposited Iridium Oxide pH Electrode for Measurement of Extracellular Myocardial Acidosis during Acute Ischemia," Anal. Chem., vol. 70, pp. 5054–5061 (1998).

Mathur, V.K; "Ion storage dosimetry," *Nuclear Instruments and Methods in Physics Research B* vol. 184 pp 190–206 (2001).

Mittal et al., Evaluation of an Ingestible Telemetric Temperature Sensor for Deep Hyperthermia Applications,: Int. J. Radiation Oncology Biol. Phys., vol. 21, pp. 1353–1361 (1991).

Moreno, D.J. et al; A Simple Ionizing Radiation Spectrometer/Dosimeter based on Radiation Sensing Field Effect Transistors (RadFETs) *TRANSDUCERS '97 International Conference on Solid–State Sensors and Actuators Chicago*, pp 1283–1286 (Jun. 16–19, 1997).

Mueller, J. S., H. T. Nagle, "Feasibility of inductive powering of miniature low–power biotelemetry for use with microfabricated biomedical sensors," Proc. Biotelemetry XIII, Williamsburg, VA, Mar., pp. 372–377 (1995).

NASA Fact Sheet, Radiation Detector for Badges for Space Walkers, 3 sheets (Oct. 2001).

Olthuis, W., Bergveld, P., "Simplified design of the coulometric sensor–actuator system by the application of a time–dependent actuator current," *Sensors and Actuators B,* vol. 7, pp. 479–483 (1992).

Oshima et al., "Development of Micro–Telemetering Multi–Sensor Capsule System with newly developed LSI for the clinical applications," Transducers '87, The 4th International Conference on Solid–State Sensors and Actuators; pp 163–166 (1987).

Pauley, Donald J., R. Martin, "A microminiature hybrid multichannel implantable biotelemetry system," *Biotelemetry Patient Monitoring,* vol. 8, pp. 163–172 (1981).

PCT Search Report PCT/US 02/38111, 2002.

Puers, B., P. Wouters, M. DeCooman, "A low power multi–channel sensor interface for use in digital telemetry," *Sensors and Actuators A,* vols. 37–38, pp. 260–267 (1993).

Small Business Innovation Research Program Phase One Grant Application entitled "An Implantable Multi–channel System for Monitoring Tumors," submitted on or about Dec. 1996 to U.S. Public Health Service.

Small Business Innovation Research Program Phase One Grant Application entitled "An Implantable Multi–channel System for Monitoring Tumors," resubmitted with revisions on or about Aug. 1997 to the National Institute of Health.

Small Business Innovation Research Program Phase One Grant Application entitled "An Implantable Multi-channel System for Monitoring Tumors," resubmitted to the U.S. funding authority on or about Apr. 1998.

Tarr, N.G. et al "A Floating Gate MOSFET Dosimeter Requiring No External Bias Supply" Redecs 97. Fourth European Conference on Radiation and Its Effects on Components and Systems (Cat. No. 97$^{TH}$ 8294) pp 277–281 (1998).

Taylor et al., The Forces in the Distal Femur and the Knee During Walking and Other Activities Measured by Telemetry, J. of Anthroplasty, vol. 13, No. 4, pp. 428–437 (1998).

Watanabe et al., "A Preliminary Report on Continuous Recording of Salivary pH Using Telemetry in an Edentulous Patient," Int'l J. Proshodontics, vol. 12, No. 4, pp. 313–317 (1999).

Webster, Editor, "Design of Cardiac Pacemakers," New York, NY: IEEE Press, pp. 155–157 (1995).

Williams et al., "Multipurpose chip for physiological measurements," IEEE International Symposium on Circuits and Systems, vol. 4, pp. 255–258, Proc. (1994).

Wolf et al., "Potential of microsensor–based feedback bioactuators for biophysical cancer treatment," Biosensors & Bioelectronics, vol. 12, pp. 301–309 (1997).

Wouters, P., M. De Cooman, R. Puers, "A multi–purpose CMOS sensor interface for low–power applications," IEEE Journal of Solid–State Circuits, vol. 29, No. 8, pp. 952–956 (Aug. 1994).

Young, R. C., V. T. DeVita, "Cell cycle characteristics of human solid tumors in vivo," Cell Tissue Kinetics vol. 3, pp. 285–290 (1970).

Zuckier et al., "Remotely Pollable Geiger–Muller Detector for Continuous Monitoring of Iodine–131 Therapy Patients," J. of Nuclear Med., vol. 39, No. 9, pp. 1558–1562 (Sep. 1998).

National Aeronautics and Space Administration, Extravehicular Activity Radiation Monitoring (EVARM), Fact Sheet FS 2001–11–192–MSFC, abstract review, Oct. 2001.

Reece M.H. et al., Semiconductor Mosfet Dosimetery, Health Physics Society annual Meeting, pp. 1–14, 1988.

Shortt, Dr. Ken et al., A New Direct Reading Exremity Dosimeter—How the ED–1 SENSOR works, Health Physics Society Annual Meeting, Jul. 1994.

Soubra, M. et al., Evaluation of a dual bias dual metal oxide–silicon semiconductor field effect transistor detector as radiation dosimeter, American Assoc. Phys. Med., vol. 21, No. 4, pp. 567–572, Apr. 1994.

Farrar IV, Harry et al., Gamma–Ray Dose Mapping in Operational Candu Reactor Containment Areas Using MOS Dosimeters, pp. 441–446, Reactor Dosimetry, ASTM, 1994.

Pendower, J., Spontaneous Disappearance of Gall–stones, Medical Memoranda, British Medical Journal, pp. 492, 1964.

Thomson, I. et al., Radiation Dosimetry with MOS Sensors, Radiation Protection Dosimetry, Viol. 6, No.1–4, Nuclear Technology Publishing, pp. 121–124, 1984.

Wayne, E. et al., Treatment of Thyroid Disorders, To–day's Drugs, British Medical Journal, pp. 493–496, Aug. 22, 1964.

PCT International Search Report, International Application No. PCT/US02/12855 dated Dec. 16, 2002.

Barber et al., Comparison of NaI(Tl), CdTe, and Hgl2 surgical probes: physical characterization, Med. Phys., 18(3):373–381 (May–Jun. 1991).

Blackstock et al., Tumor retention of 5–fluorouracil following irradiation observed using 19F nuclear magnetic resonance spectroscopy, Init J Radiat Oncol Biol Phys, 36(3):641–648 (Oct. 1, 1996).

Bojsen et al., A portable external two–channel radiotelemetrical GM–detector unit, for measurement of radionuclide–tracers in vivo, Int J Appl Radiat Isot, 24(4):161–166 (Apr. 1974).

Bojsen et al., A radiotelemetrical measuring device, implantable on animals, for long term mersurements of radionuclide tracers, Int J Appl Radiat Isot, 23(11):505–511 (Nov. 1972).

Daghighian et al., Intraoperative beta probe: a device for detecting tissue labeled with positron or electron emitting isotopes during surgery, Med Phys, 21(1):152–157 (Jan. 1994).

Dewhirst et al., Soft–Tissue Sarcomas: MR Imaging and MR Spectroscopy for Prognosis and Therapy Monitoring, Radiology, 174:847–853 (1990).

Dimitrakopoulou et al., Studies with Position Emission Tomography After Systemic Administration of Fluorine–18–Uracil in Patients with Liver Metastases from Colorectal Carcinoma, J Nucl Med, 34:1075–1081 (Jul. 1993).

Fisher, DR, Radiation dosimetry for radioimmunotherapy. An overview of current capabilities and limitations, Cancer, 73(3 Suppl):905–911 (Feb. 1, 1994).

Gelezunas et al., Silicon avalanche radiation detectors: the basis for a new ini vivo radiation detection probe, Eur J Nucl Med, 8(10):421–424 (1983).

Hamburger et al, Primary Bioassay of Human Tumor Stem Cells, Science, 197:461–463 (1977).

Hassan e al., A radiotelemetry pill for the measurement of ionizing radiation using a mercuric iodide detector, Phys med Biol, 23(2):302–308 (Mar. 1978).

Heij et al., Intraoperative search for neuroblastoma by MIBG and radioguided surgery with the gamma detector, Med Pediatr Oncol, 28(3):171–174 (Mar. 1997).

Hoffman et al., Intraoperative probes and imaging probes, Eur Jnl Nucl Med, 26(8):913–935 (Aug. 1999).

Kastrissios et al., Screening for Sources of Interindividual Pharmacokinetic Variability in Anticancer Drug Therapy: Utility of Population Analysis, Cancer Investigation, 19(1):57–64 (Jan. 30, 2001).

Kern, D.H., Tumor Chemosensitivity and Chemoresistance Assays, Cancer 79(7):1447–1450 (1997).

Khouri et al., An implantable semiconductor beta–radiation detector, Am J Physiol, 232(1):H95–98 (Jan. 1977).

Kissel et al., Noninvasive determination of the arterial input function of an anticancer drug from dynamic PET scans using the population approach, Med Phys 26(4):609–615 (Apr. 1999).

Koutcher et al., Potentiation of a Three Drug Chemotherapy Regimen by Radiation, Cancer Res, 53:3518–3523 (1993).

Piwnica–Worms et al., Functional Imaging of Multidrug–resistant P–Glycoprotein with an Organotechnitium Complex, Cancer Res, 53:977–984 (1993).

Presant et al., Enhancement of Fluorouracil Uptake in Human Colorectal and Gastric Cancer by Interferon or by High–Dose Methotrexate: An In Vivo Human Study Using Noninvasive $^{19}F$–Magnetic Resonance Spectroscopy, J Clin Oncol, 18:255–261 (2000) Jan. 4, 1999.

Present et al., *Human tumor fluorouracil trapping: clinical correlations of in vivo 19F nuclear magnetic resonance spectroscopy pharmacokinetics,* J Clin Oncol, 8(11):1868–1873 (Nov. 1990).

Raylman et al., *Evaluation of ion–implanted–silicon detectors for use in intraoperative positron–sensitive probes,* Med Phys, 23(11):1889–1895 (Nov. 1996).

Stevens et al., *5–Flourouracil metabolism monitored in vivo by $^{19}F$ NMR,* Br J Cancer, 50:113–117 (1984).

UCL Christian de Duve Institute of Cellular Pathology, Ludwig Institute for Cancer Research, URL www.Icp ucl ac be/report95/licr95html (1995).

Von Hoff et al., *Selection of Cancer Chemotherapy for a Patient by an In Vitro Assay Versus a Clinician,* JNCI 82:110–116 (1990) Oct. 25, 1989.

Wolf et al., *19F–MRS studies of fluorinated drugs in humans,* Adv Drug Deliv Rev, 41(1):55–74 (Mar. 15, 2000).

Wolf et al., *Non–invasive 19F–NMRS of 5–fluorouracil in pharmacokinetics and pharmacodynamic studies,* NMR Biomed 11(7):380–387 (Nov. 1998).

Wolf et al., *Tumor trapping of 5–fluorouracil: In vivo $^{19}F$ NMR spectroscopic pharmacokinetics in tumor–bearing humans and rabbits,* Proc Natl Acad Sci USA, 87:492–496 (Jan. 1990).

Woolfenden et al., *Radiation detector probes for tumor localization using tumor–seeking radioactive tracers,* AJR Am J Roentgenol, 153(1):35–39 (Jul. 1989).

Yarnell et al., *Drug Assays on Organ Cultures of Biopsies from Human Tumours,* Br Med J 2:490–491 (1964).

Zanzonico et al., *The intraoperative gamma probe: basic principles and choices available,* Semin Nucl Med 30 (1):33–48 (Jan. 2000).

Ranii, D., N&O Article, *Company's device aims to monitor disease from inside.,* Mar. 30, 2000.

Ranii, D., N&O Article, *Sicel seeks go–ahead for clinical trials.* Apr. 17, 2002.

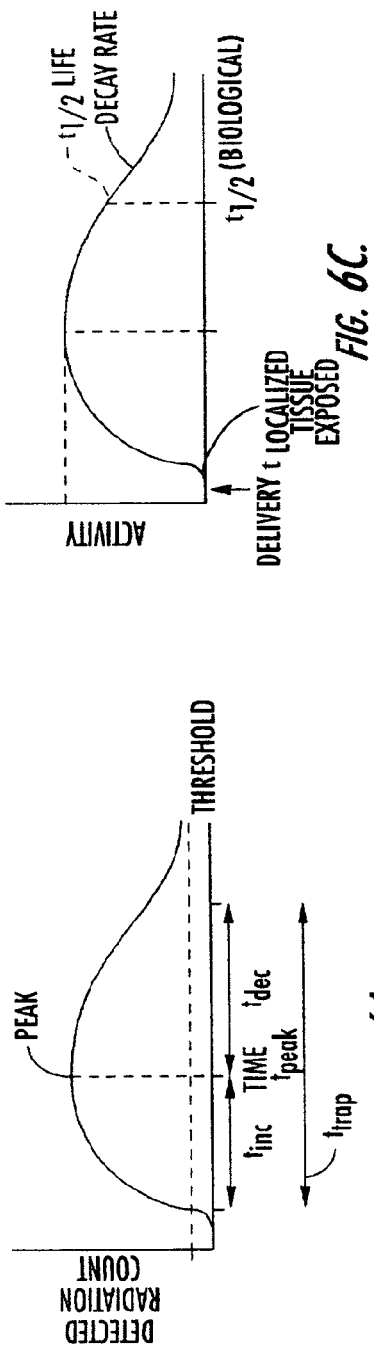
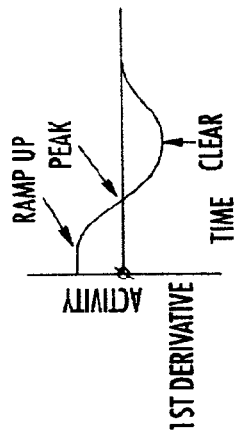
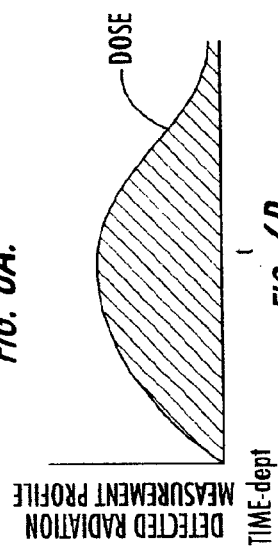
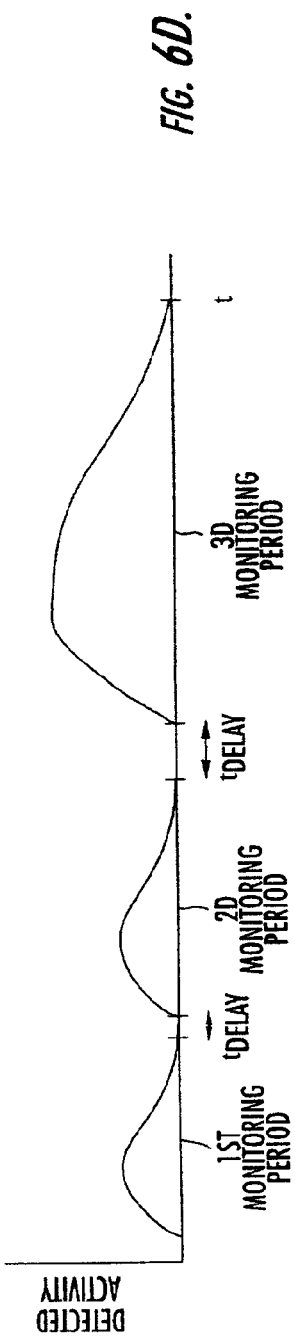
FIG. 6A.
FIG. 6B.
FIG. 6C.
FIG. 6D.
FIG. 6E.

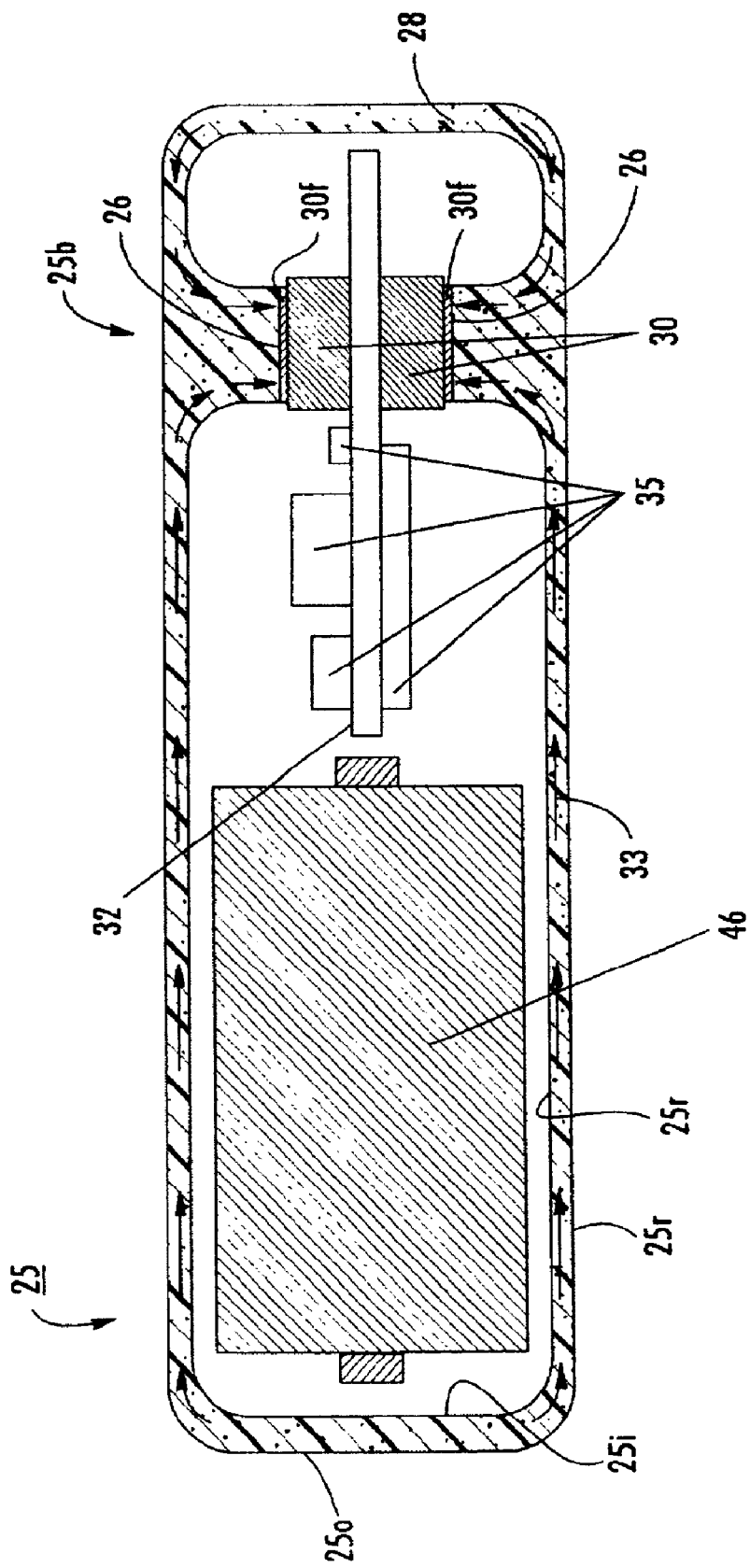

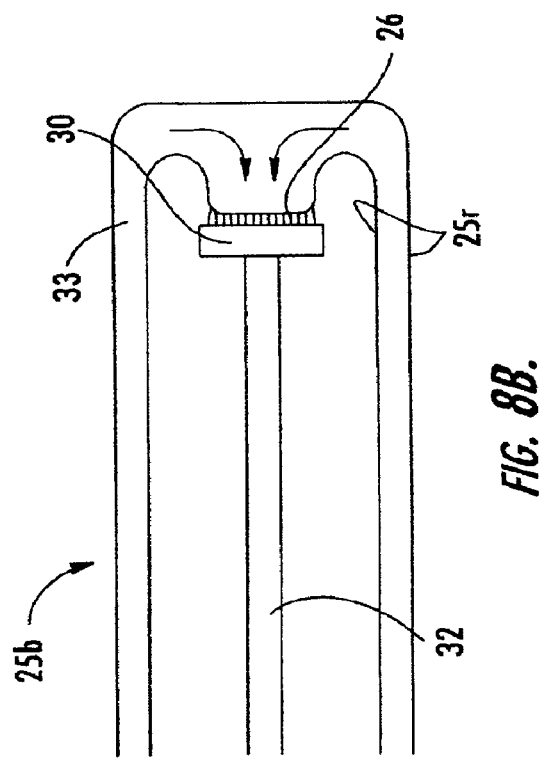
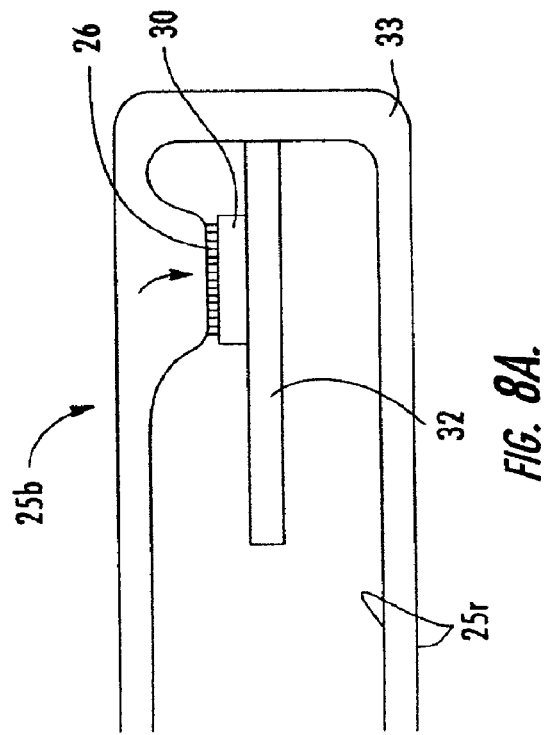

SYSTEMS, METHODS AND DEVICES FOR IN VIVO MONITORING OF A LOCALIZED RESPONSE VIA A RADIOLABELED ANALYTE IN A SUBJECT

RELATED APPLICATION

This application claims priority from U.S. Provisional Ser. No. 60/285,923, filed Apr. 23, 2001, the contents of which are hereby incorporated by reference as if recited in full herein.

FIELD OF THE INVENTION

The present invention is related to systems and methods for monitoring radiation and/or metabolic activity in a subject.

BACKGROUND OF THE INVENTION

One of the major problems in the management of the cancer patient is the predictability or determination of therapy response prior to the initiation of treatment. This can be particularly important for the patient receiving chemotherapy. The conventional approaches in the determination of the treatment protocol (to establish a treatment agent or drug(s) regimen) to be used in the treatment of specific tumor type remains largely empirical. That is, the conventional therapeutic approach is to utilize what is considered to be the most effective treatment as determined by prospective randomized trials across a sampled population. This approach overlooks the fact that, as each patient is different, so is each patient's tumor and/or response to the treatment selected. The biological and physiological uniqueness of each patient is not considered nor is the potential for an individualized therapeutic approach. See generally Kastrissios et al., *Screening for Sources of Interindividual Pharmacokinetic Variability in Anticancer Drug Therapy: Utility of Population Analysis*, Cancer Investigation, 19(1), 57–64 (2001).

Both the need for and potential benefits of a predictive test for a patient's response to a particular treatment protocol, particularly for the cancer patient, have long been recognized. The benefits include (a) an increased chance for tumor response from initial effective therapy, (b) a reduction in the potential for development of resistant cells when less effective therapy is given (c) a decreased morbidity associated with non effective therapy, and (d) an improved probability of cure or positive outcome with the timely administration of effective therapy. It is generally accepted that the initial treatment approach is the most important to obtain the best tumor response. Second and third line therapies are typically less effective and primarily palliative. Therefore, the availability of a method to determine the most appropriate and effective drug (s) prior to the initiation of therapy may allow for a maximum response. That is, if, for a given tumor, several drugs have been shown to be effective in large clinical trials, the question as to which one (s) to use in a particular patient can be important. Since, as noted above, differences do exist between individual tumors of the same site, choosing the most effective therapeutic agents should increase the likelihood of a beneficial response and reduce the chance for the development of a resistant cell population. It may also reduce the possibility of utilizing a particular drug as a second or third line therapy, when its effectiveness may be reduced because of the development of drug resistant populations.

An important additional benefit to the patient may be a lower morbidity rate than that which is associated with a "try and see" approach (that is, to "try" a specific regimen and "see" how the patient responds). A knowledge of effective drugs may reduce the morbidity of therapy, since it will offer the patient an increased chance for response and/or reduce the need for second and third line therapies.

The early attempts to establish predictive tests were dependent on the availability of cell culture techniques and cell lines. The tests included evaluation of cell morphology, exclusion of vital dyes, and incorporation of radioactive precursor molecules after incubation of tumor cells with anticancer agents. The primary problem was a lack of predictive value in most correlative studies. See, e.g., Yarnell et al., *Drug Assays on Organ Cultures of Biopsies from Human Tumours*, Br Med J 1964; 2:490–491. More recently, the culture of human tumors was reported by Hamburger et al., in *Primary Bioassay of Human Tumor Stem Cells*, Science 1977;197:461–463. Since its introduction, the Human Tumor Clonogenic Assay (HTCA) has been investigated as a predictive assay for human tumors. Contrary to the previously identified assays, inhibition of cellular proliferation is directly used as the experimental endpoint. In addition, it defines results in terms of chemoresistance and chemosensitivity. The cumulative results of over 2300 correlations between the HTCA and clinical response was reported by Von Hoff et al. in 1990. See Von Hoff et al., *Selection of Cancer Chemotherapy for a Patient by an In Vitro Assay Versus a Clinician*, JNCI 1990;82:110–116. The results revealed a 69% probability for a patient to have at least a partial response if the tumor specimen is sensitive to the drug in vitro. However, if the tumor is resistant in vitro, there appears to be a 91% chance for clinical resistance. The major technical problems with most clonogenic assays include the lack of growth in 40 to 60% of all specimens and a relatively long incubation time (generally on the order of at least 14 days) before results are available. In addition, there is insufficient data available on the effect of assay-guided chemotherapy on patient survival, and most clinically observed responses are partial responses.

More recently, a commercially available assay has alleged a 99% accuracy in prediction of clinical failure. The success of the assay purportedly results from extended exposure of the patient tumor cells to levels of chemotherapy agents, which approximate the peak plasma levels attained after conventional IV administration. If a patient's cells proliferate after extended exposure to peak plasma levels of chemotherapy agents, then it can be accurately predicted that these cells will also demonstrate resistance to normal exposures in vivo. However, the reported accuracy to predict chemo-sensitivity is only about 60–70%. Moreover, the assay method is not able to address tumor response over time or in real time. The sample represents the biology of only one point in time of the treatment history of each tumor; it does not consider conditions that effect drug delivery to the tumor, including poorly perfused tumors, local areas of hypoxia or acidosis and host-dependent resistance mechanisms which can cause high false-positive prediction of in vitro chemo-sensitivity. See Kem D H, *Tumor Chemosensitivity and Chemoresistance Assays*, Cancer, 79:7, 1447–1450, 1997.

Others have proposed alternative methods such as Single Photon Emission Tomography (SPECT) and Positron Emission Tomography (PET), which have been found to be useful for obtaining functional data of tumors when radiopharmaceuticals are utilized. There are several approaches for the assessment of chemotherapeutic effects that include measurement of tumor metabolism, quantification of pharmacokinetics of radiolabeled drugs and evaluation of multidrug resistance. A commonly used positron emitting radiopharmaceutical for oncological studies is F-18-Fluordeoxyglucose (FDG). FDG is a tracer, which parallels the transport and phosphorylation of glucose into the cell but is then trapped. Therefore, it is used as an estimate for the regional tumor glucose metabolism. In addition, FDG is a tracer that shows a preferential accumulation in most of the tumor types. As a result, therapy monitoring may be performed using multiple follow-up PET studies where a decrease in tumor uptake correlates with clinical response to therapy, and conversely an increase is indicative of tumor growth. PET can typically be utilized to measure the kinetics of the drug over a target area in normal tissue and in the vascular system. Generally stated, only 5FU (5-Fluorouracil) has been found useful for routine PET scanning. See Kissel et al., *Noninvasive determination of the arterial input function of an anticancer drug from dynamic PET scans using the population approach*, Med Phys 1999 April; 26(4):609–15.

In operation, the PET methodology may allow for the direct measurement of radiotracer concentrations and, thus, a quantification of the 5-[F-18]FU accumulation. Dimitrakopoulou et al., *Studies with Positron Emission Tomography After Systemic Administration of Fluorine-18-Uracil in Patients with Liver Metastases from Colorectal Carcinoma*, J Nucl Med, 1993 July, 34:1075–1081. When utilized to assess liver metastasis from the colon, kinetic data showed different distribution patterns for the metastases, the normal liver parenchyma and the vessels. The normal liver parenchyma has the highest 5-[F-18]FU uptake about 30 minutes after onset of the infusion of the tracer, followed by a decrease to 25% of the maximum at the end of the acquisition time. The uptake in the metastases was low and relatively constant during the 120-minute acquisition time. The mean uptake was one-third of the liver uptake at the same time interval. Two caveats associated with the distribution pattern reflect the difficulty in utilizing one (single) observation in determining effective therapeutic response. It was observed that the early 5-FU uptake is primarily determined by the intracellular uptake of non-metabolized 5-FU. Late 5-[F-18]FU uptake values, e.g., 120 minutes after onset of the 5-FU application, are used as a prognostic parameter for therapy response, since the data obtained from that time interval are most likely to mirror the therapeutically active fraction of the drug. In addition, 5-[F-18]FU studies demonstrated a great variability of drug uptake in liver metastases even in the same patient, which may explain the low response rates and the variability in response to therapy. The 5-[F-18]FU concentration as measured with PET prior to onset of 5-FU chemotherapy is predictive of therapy outcome, since only a high 5-FU trapping in the metastasis is correlated with regression, while low 5-FU concentration are not capable of preventing tumor growth during chemotherapy.

PET can also be used to study mechanisms of drug resistance by employing a combination of O-15 labeled water and 5-[F-18]FU. The former has been used to study the transport system and identified a difference between a passive and active energy-dependent transport systems. Enhanced 5-FU trapping was noted in 70% of these lesions. Since only tumor lesions with an energy-dependent transport system of 5-FU are likely to respond to 5-FU therapy, this information is believed to be of clinical value for the individualization of the therapeutic protocol. PET can be used to select those patients with metastases possessing an active 5-FU transport system, which can aid the oncologist to direct therapy by modifying the treatment protocol.

Multidrug resistance (MDR) occurs when cells appear to overcome the cytotoxic effect of chemotherapy. Cytotoxic drugs are rapidly eliminated, especially in cells with a high concentration of P-glycoprotein (Pgp), a transmembrane drug flux. Tumors from the colon, kidney, liver and pancreas frequently express the Pgp at high levels. Studies by Piwnica-Worms et al. reported on the use of Tc-99m-sestamibi, a synthetic organotechnetium complex, that can act both as a substrate for Pgp and can act as a marker for the expression of Pgp. See Piwnica-Worms et al., *Functional Imaging of Multidrug-resistant P-Glycoprotein with an Organotechnetium Complex*, Cancer Res 53, 977–984, 1993. A high Sestamibi accumulation in the tumor correlated with a low Pgp expression and a good prognosis for chemotherapy. Despite these advances and observations, there are limitations of PET methodology. Practically speaking, this evaluation method would potentially be available to only a limited number of patients since it can be time consuming, expensive and impractical for application, not only to every patient, but on multiple occasions. Secondly, PET scans cannot discriminate metabolites. In order to improve the interpretation of the PET data, Nuclear Magnetic Resonance Spectroscopy (NMRS) has also been used in some patients.

Following the observation in 1984 by Stevens et al., 5-*Flourouracil metabolism monitored in vivo by* $^{19}F$ *NMR*, Br J Cancer 1984, 50:113–117, who showed that 19F-NMRS could detect 5-FU in the liver of mice, the work was extended to observations in the tumors of rats and mice. See Wolf et al., *Tumor trapping of 5-fluorouracil: In vivo* $^{19}F$ *NMR spectroscopic pharmacokinetics in tumor-bearing humans and rabbits*, Proc Natl Acad Sci USA, 1990, January, 87:492–496. In 1990, Presant et al. reported their initial observations on the clinical experience with NMRS in 11 patients. They described a "trapped" pool of intratumoral 5-FU, defined as a pool of 5-FU whose disappearance half-life ($T_{1/2}$) is longer than its $T_{1/2}$ in peripheral blood. They also presented information on the correlation between the $T_{1/2}$ of 5-FU in tumors and anti-tumor response to 5-FU. Generally stated, they found that the six patients with $T_{1/2}$ of greater than 20 minutes responded to chemotherapy and that the converse was also true. More recently, Presant et. al., in *Enhancement of Fluorouracil Uptake in Human Colorectal and Gastric Cancers by Interferon or by High-Dose Methotrexate: An In Vivo Human Study Using Noninvasive* $^{19}F$-*Magnetic Resonance Spectroscopy*, J Clin Oncol 18:255–261; 2000, reported that the in vivo modulation of the tumoral pharmacokinetics of 5-FU could be measured non-invasively by 19F-MRS and; suggested that such information correlates with subsequent clinical outcomes. Further, they suggested that interferon (IFNa-2a) and high-dose methotrexate could increase the intratumoral 5-FU in some patients.

31P/NMR spectra contain peaks from nucleoside triphosphates (NTP), phosphocreatine (PCr), and inorganic phosphates (Pi) and can therefore provide information about tumor energy status. The potential of 31P/NMR spectroscopy for evaluating the effect of treatment (radiation and hyperthermia) on sarcomas has been studied by Dewhirst et al. Dewhirst et al., *Soft-Tissue Sarcomas: MR Imaging and MR Spectroscopy for Prognosis and Therapy Monitoring*, Radiology 174:847–853, 1990. They purportedly observed a relationship between treatment-induced decrease in ATP/Pi with the probability of development of necrosis and in a related study showed an increase in oxygenation after treatment correlated with the amount of tumor necrosis. Another example of an application of 31P/NMR spectroscopy is in the monitoring of biochemical inhibition of specific metabolic pathways. This inhibition is designed to enhance tumor response to radiation and chemotherapy. Agents such as 2-deoxyglucose, lonidamine, 6-aminonicotinamide (6AN) can inhibit biochemical pathways and enhance responses to chemotherapy and radiation. Koutcher et al. (in Koutcher et al., *Potentiation of a Three Drug Chemotherapy Regimen by Radiation*, Cancer Res 53:3518–3523, 1993) observed changes in spectra of mammary carcinoma before and after treatment with a 3-drug combination. The observed changes were used to determine the timing between the drugs and radiation based on when tumor metabolism was maximally inhibited. While the drugs alone induced no complete responses and radiation only induced a single (1/20) "complete response" (CR), the combination of the drugs and radiation (administered when the NMR data demonstrated maximal metabolic inhibition) yielded a 65% CR rate and a 25% durable (<1 year) CR rate, without further treatment.

Several groups have proposed the use of intraoperative radiation probes for the purpose of identifying cancerous regions in the body. See e.g., Zanzonico et al., *The intraoperative gamma probe: basic principles and choices available*, Semin Nucl Med 30 (1), pp. 33–48 (January 2000); Barber et al., *Comparison of NaI(Tl), CdTe, and HgI2 surgical probes: physical characterization*, Med. Phys.; 18(3), pp.373–381 (May–June 1991); and Hoffman et al., *Intraoperative probes and imaging probes*, Eur Jnl. Nucl. Med. 26(8), pp. 913–935 (August 1999). These techniques can be characterized as belonging to one of two primary applications: radioimmunoguided surgery (RIGS) and sentinel node detection. It is believed that the RIGS applications may be generally described as radiolabeling an antibody specific to a target tumor and then probing in the operational field with a radiation detector to evaluate which tissue may be suspect. It is believed that this technique can provide better localization than is available with SPECT (Single Photon Emission Computed Tomography).

The sentinel node detection techniques can be described as using an injection of a radiolabeled substance -into a tumor and then recording or evaluating the "downstream" activity of the radiolabeled substance to determine the degree of lymph node involvement. A clinician can use a pen-like gamma probe to trace or detect the signal associated with the radioactivity of the lymph nodes (such as during a surgical procedure).

It is also known that there are changes in glycolysis in normal versus tumor cells. The facilitative glucose transporters (GLUT 1–5 and 7) have been reported as proteins that regulate transport of glucose from the blood to cytoplasm. These proteins are passive transporters and, thus, provide glucose to the interior of a cell if a concentration gradient exists. As previously suggested, increased uptake of glucose by cancer cells may be due to an up-regulation of the GLUT genes responsible for the proteins. Because transport of glucose by these transmembrane proteins is passive, the concentration in the cytoplasm is kept below the level in the interstitial fluid. This means that glycolysis can accelerate to keep up with the process and to attempt to maintain the desired internal cell level or transmembrane concentration gradient. Therapies that disrupt a key element of glycolysis may arrest the avid uptake of glucose by tumors by reducing the transmembrane concentration gradient. [18F]FDG has been used recently to look at alterations in glucose uptake following radiation therapy. This observation may be important in assessing the onset of apoptosis due to radiation exposure. Glucose transport has been studied after induction of apoptosis by gene therapy designed for a rat tumor model.

[11C]glucose labeled in the 1 and 6 carbon positions was used to look at the "pentose cycle." This cycle preferentially selects carbon in the first position and incorporates it into $CO_2$. Thus, it has been proposed that the ratio of C1/C6 could be predictive of the staging of gliomas. However, this proposed evaluation method may be difficult in that there is a low (approximately 5%) amount of glucose entering the pentose cycle and because the evaluation method is performed in successive runs (first for C1 and then for C6) with a clinically challenging PET isotope.

Despite the foregoing, there remains a need to provide cost-effective and/ or alternative methods, systems and devices that can individualize and customize therapy to improve response and outcome and/or otherwise monitor therapeutic response or delivery of radiolabeled agents in the body. There is also a need for methods, systems and devices that can provide increased information on normal and/or tumor glycosis and/or the impact of therapies on same.

SUMMARY OF THE INVENTION

The present invention provides methods, systems, devices and computer program products for in vivo dynamic monitoring of detected radiation which is emitted from localized tissue in a target region of the body over a selected response or watch period. Generally described, the monitoring can be carried out as a general metabolic assessment, to evaluate or monitor therapy types (including antibody and pharmaceutical therapies) and/or to obtain data and evaluate metabolic, biokinetic parameters, or predictor variables associated with the in vivo detected radiation. The data can be used, inter alia, to: (a) predict or assess the likelihood that a planned treatment will be effective (before or after a first or subsequent therapeutic dose is actually administered to the subject); (b) identify which drug or drugs will provide a suitable clinical response for that subject; (c) monitor intratumoral kinetics; (d) study pharmacokinetics and/or pharmacodynamics; (e) study the impact of modifying agents, treatments, or procedures on drug or antibody uptake and/or retention or tumor kill or morbidity; (f) measure uptake, trapping, or retention of radiolabeled analytes (for any desired treatment, whether drug, antibody, and/or radioimmunology); (g) study an individual's bio-response to a therapy; (h) exclude certain therapy choices; and (i) to evaluate metabolic activity or behavior.

Operations of certain embodiments can be carried out to assess glycolysis and/or to examine specific therapies with respect to altered glycolysis or dynamic changes in glycolysis. Such analysis may be carried out by employing [$^{14}$C]glucose and/or glucose derivatives as well as the resulting constituents resulting from the glycolysis or metabolic biochemical process in the body.

Alternatively, the monitoring may be used to quantitatively measure the radiation dose received at localized tissue in the target region (such as used for radioimmunotherapy). While in other embodiments, the present invention can use the detected radiation to analyze the pharmacokinetics/ pharmacodynamics or in vivo performance of certain pharmaceutical grade drugs or drug products or derivatives thereof, as well as analytes, antibodies, metabolites or other therapeutic treatments in the body.

Advantageously, in certain embodiments, the present invention-can provide cost-effective minimally invasive methods, systems, and devices that can evaluate, in substantially real-time, one or more selected biokinetic parameters or predictor variables of a subject. Certain embodiments of the devices and systems can be configured to identify the differences in response between normal and malignant tissue and/or the differences in the physiology and biology of individual tumors (or the same at different times) and to utilize the identified information regarding same to develop individualized treatment decisions, and/or to predict therapeutic outcome or to improve tumor response.

Other embodiments may allow improved individualized treatment protocols based on an in vivo detected uptake or trapping or other desired response (over a selected time) of a non-therapeutic dose of a drug typically evaluated before and proximate in time to the delivery of the therapeutic dose) to predict the response of the subject to a therapeutic dose of a drug in advance of administration thereof. Such predelivery assessment capability may be able to allow an improved selection of chemical or treatment drug, reducing unnecessary ineffective administration of cytotoxic agents which are unlikely to be clinically effective. Thus, the present invention can identify, by measuring detected radiation associated with the uptake and retention of a radiolabeled or radioactive substance, the sensitivity or receptiveness of a tumor for a particular treatment, proximate in time to the planned delivery or administration of same.

Other embodiments gather data during a treatment cycle and evaluate it to determine the likely clinical efficacy based on the detected kinetic activity data.

Certain embodiments of the present invention are directed to methods for determining the in vivo clinical efficacy of a treatment in a subject. The method can include the steps of: (a) positioning a sensor in tissue in a region of interest in the body; (b) administering a radiolabeled analyte to a subject; (c) detecting in vivo from the implanted sensor a signal corresponding to the radiation emitted from the radiolabeled analyte in the region of interest in the subject; (d) relaying the signal to a location external of the subject's body; and (e) monitoring the (relayed) signal over time to determine the response of the subject to the administered analyte to predict or assess at least one of the in vivo clinical efficacy of a selected treatment and/or the metabolic activity in the region of interest.

In certain embodiments, the radiolabeled analyte may be a C-14 (beta emitter) labeled version of a non-labeled corresponding drug or antibody that is undergoing pharmacokinetic/pharmacodynamic evaluation in clinical or pre-clinical drug trials (or other drug development testing). In other embodiments, the radiolabeled analtye may be an analog of a chemotherapeutic agent for cytotoxic cancer treatment such as, but not limited to, a C-14 labeled chemotherapeutic or cytotoxic agent.

Certain embodiments of the present invention are directed to methods for determining the clinical efficacy or the metabolic behavior of the subject when exposed to a selected pharmaceutical or chemical product in a subject. The method comprises the steps of: (a) administering a first quantity of a C-14 radiolabeled version of a pharmaceutical product (such as a drug or antibody) to a subject; (b) detecting a signal from an in situ sensor, the signal corresponding to the radiation emitted by the radiolabeled pharmaceutical product in a region of interest in the subject; (c) relaying the signal to a location external of the subject's body; (d) repeating said detecting and relaying steps over at least about 0.25–12 hours; and (e) monitoring the signals over time.

In certain embodiments, the monitoring step can be used to determine the metabolic and/or biokinetic response of the subject to thereby predict or assess the in vivo clinical efficacy or local tissue sensitivity to a therapeutic dose of a pharmaceutical product prior to administration thereof.

The administrating step can be carried out in vivo and performed such that the radiolabeled pharmaceutical product is either delivered locally to the region of interest (such as via injection thereat) or such that the radiolabeled pharmaceutical product is delivered systemically (such as through a syringe or an intravenous catheter). The C-14 pharmaceutical can be provided as a first quantity amount which is less than a therapeutic quantity of a corresponding non-radiolabeled pharmaceutical product.

Other embodiments of the present invention are directed to a detection system for detecting radiation emitted from an internally administered radioanalyte. The system includes at least one radiation sensor configured for in vivo operation. The sensor is configured to detect beta radiation emitted from the radiolabeled analyte or its biochemical constituents, in or proximate targeted localized tissue in the body. The sensor is configured to detect emitted beta radiation, at least intermittently, over a period of time extending from about 0.25–24 hours (the evaluation period can be proximate in time to and at least before each of a plurality of planned therapeutic treatments which are administered temporally separate from each other). The system also includes a processor operably associated with (each of) the radiation sensor(s). The processor is configured to receive signal data associated with the detected radiation from the sensor. The processor includes computer program code for monitoring selected in vivo parameters associated with time-dependent measurement profile and/or the uptake and/or retention of the radioactive substance in the targeted localized tissue.

Yet other embodiments of the present invention are directed to computer program products for evaluating an individual's response to a planned cancer treatment regimen, the computer program product comprising a computer readable storage medium having computer readable program code embodied in the medium. The computer-readable program code comprising: (a) computer readable program code for receiving a first measurement of radiation detected in vivo in tissue located about a local targeted site in the body of a subject, the detected radiation corresponding to radiation emitted from a radioactive or radiolabeled substance administered internally to the subject; (b) computer readable program code for receiving a second measurement of the radiation detected in the tissue located about the targeted site after the first measurement the detected radiation corresponding to radiation emitted from the radioactive substance or radiolabeled analyte administered internally to the subject; and (c) computer readable program code for generating a time-dependent measurement profile for evaluating selected parameters associated with at least one of the uptake and retention of the radioactive or radiolabeled analyte in the localized tissue of the subject based on the first and second measurements.

In other embodiments, the computer program code can be configured to obtain third and fourth measurements (or more measurements).

Other embodiments are directed to computer program products and methods for quantifying the amount of radiation delivered to tissue in a targeted local site in the body of a subject in response to a radioimmunology treatment. The program product can include computer readable program code for (a) receiving data associated with radiation detected in vivo in tissue located about a local targeted site in the body of a subject, (b) computer readable program code for generating a time-dependent measurement profile of the detected radiation at the local site; and (c) computer readable program code for evaluating the amount of radiation delivered to the localized tissue based on the time-dependent measurements.

The detected radiation can be based on internally administered radiation that is directed as a therapeutic pharmaceutical treatment to a target region of interest in the subject. The computer program product can include computer program code for initiating the first and second measurements a plurality of times over an active treatment period extending at least from about 5–10 minutes to 24 hours or more, over one or a plurality treatments (such as a plurality of radioimmunology treatment sessions for the treatment of cancerous tumors or tissue).

The detected radiation can be used to confirm delivery of the product to the targeted site and/or to quantify dose or uptake/retention or response of the tumor to the product thereat. Such information may be used for monitoring a selected therapeutic treatment(s). The system or program can be configured to detect radiation related to the internal activity of C-14 labeled glucose. This data or information may also be used for therapeutic assessment and/or monitoring.

Other systems or computer programs can be configured for evaluating an individual's metabolic activity using an in vivo administered beta radiolabeled analtye or metabolite. The program includes: (a) computer readable program code for receiving data for a first measurement of radiation detected in vivo in tissue located about a local targeted site in the body of a subject, the detected radiation corresponding to radiation associated with a radiolabeled analyte administered internally to a subject; (b) computer readable program code for receiving data for a second measurement of the radiation detected in the tissue located about the targeted site after the first measurement, the detected radiation corresponding to radiation associated with the radiolabeled analyte administered internally to the subject; and (c) computer readable program code for monitoring the received data over time to evaluate the metabolic activity of the local targeted site.

Other embodiments are directed to a method of quantifying the amount of radiation delivered to or the metabolic activity of tissue in a targeted local site in the body of a subject. The method comprises the steps of: repeatedly detecting radiation in vivo in tissue located about a local targeted site in the body of a subject over a response window; and evaluating the uptake and retention of radiation in the local site over the response window to determine the amount of radiation delivered to the localized tissue based on the detecting step.

Additional embodiments are directed to systems for analyzing in vivo metabolic activity of a subject. The system includes detection means for detecting metabolic kinetic activity in vivo based on the levels of radiation present in a localized in vivo region of interest responsive to an internally administered radioanalyte in the subject over a desired time interval of interest; and analyzing means for analyzing data associated with the detected radiation to determine the in vivo metabolic kinetic activity of the subject.

The system may further include a biocompatible radiolabeled analyte configured for human or animal administration and the detection means can be adapted to detect the concentration activity of the radiolabeled analyte in the region of interest.

The present invention can acquire data associated with the detected radiation and generate at least one time-dependent measurement profile of the radioactivity in a localized region of the subject. The time-dependent profile can be analyzed to identify or quantify one or more predictor variables which captures desired information corresponding to one or more of the efficacy, performance, activity, or status of the radiolabeled substance in the body and/or targeted or localized tissue. The predictor variables or parameters can include (but are not limited to) the biological ½ life of the radiolabeled analyte in the localized tissue, the amount of time the detected radiation is above a predetermined threshold level, the amount of time that the radiation detected is increasing, the peak value of the detected radiation, the time at which the peak radiation level occurs, and the decay rate of the detected radiation.

The foregoing and other objects and aspects of the present invention are explained in detail in the specification set forth below.

BRIEF DESCRIPTION OF THE DRAWINGS

FIGS. 6A–6E are graphs of simulated or predicted radiation activity measurements over time or time-dependent measurement profiles which can be monitored according to embodiments of the present invention. FIGS. 6A and 6C illustrate time dependent measurement profiles with examples of some predictor variables or kinetic parameters. FIG. 6B illustrates that the dose can be based on a mathematical integral of the area under the curve of the measurement profile. FIG. 6E illustrates that a first derivative of count per second can be mathematically derived for dose evaluation. FIG. 6D illustrates that a plurality of time-dependent profiles can be obtained on the localized tissue at different time or evaluation periods to obtain substantially real time or dynamic information so as to assess the status or receptiveness/sensitivity or performance of the drug at the localized tissue.

FIG. 7 is a cross-sectional view of an implantable radiation sensor according to embodiments of the present invention.

FIG. 8A is a partial cross-sectional view of an alternate embodiment of a radiation sensor according to the present invention.

FIG. 8B is a partial cross-sectional view of an additional embodiment of a radiation sensor according to the present invention.

DESCRIPTION OF EMBODIMENTS OF THE INVENTION

Figure 1:
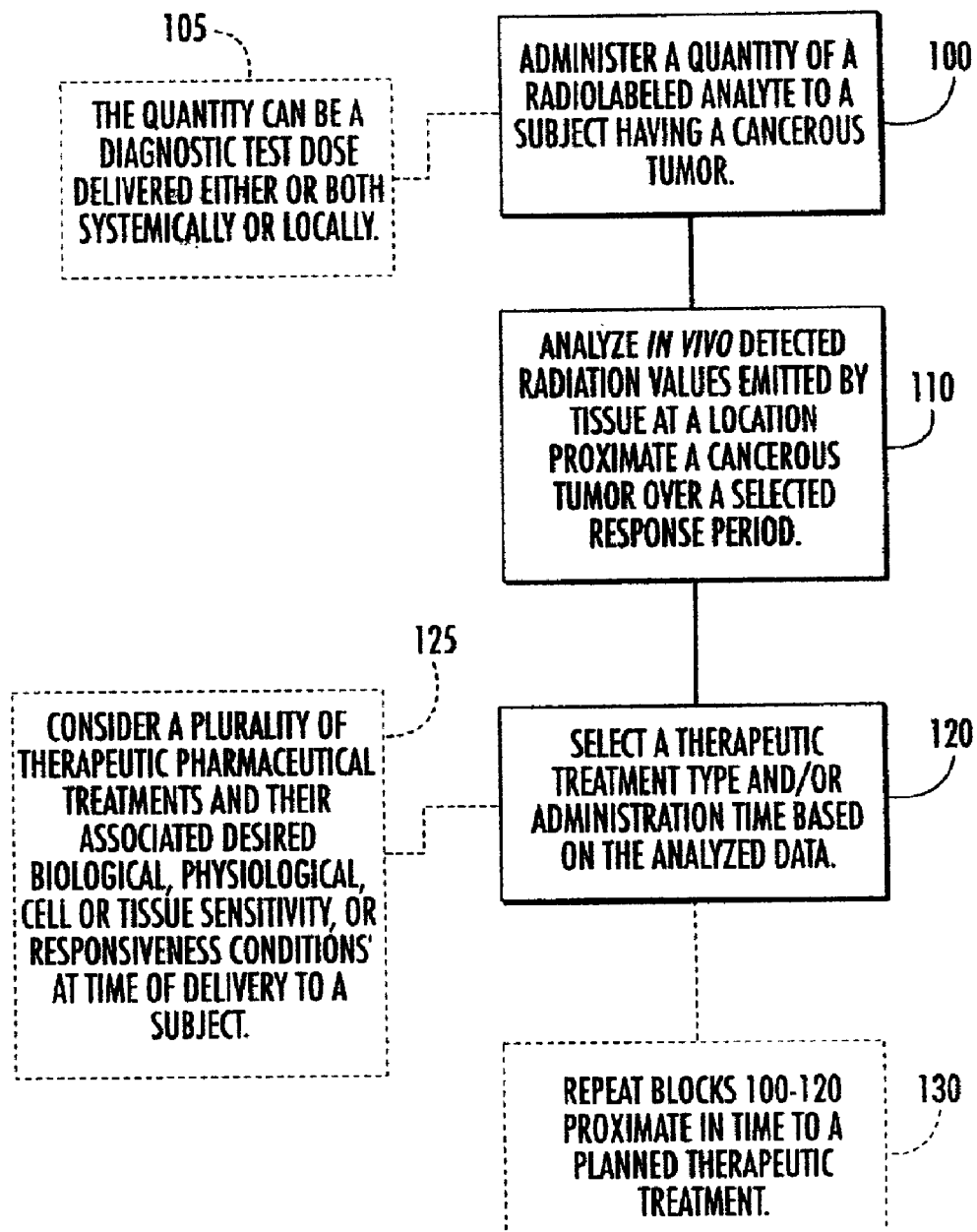
FIG. 1 is a block diagram of a method of operation according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers may be exaggerated for clarity. In the figures, broken lines, unless stated otherwise, represent optional steps or features.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer, processor (such as a digital signal processor), or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

Generally described, in certain embodiments, the proposed device and systems can be used to obtain data and/or measure or monitor the emission of radiation from radiolabeled analytes. The term "radiolabeled analytes" includes, but is not limited to, radiolabeled antibodies, radiolabeled antigens, radiolabeled nucleic or amino acids, other radiolabeled endogenous substances or molecules such as glucose or other naturally occurring substances and/or their derivatives, metabolites, or constituents, and radiolabeled exogenous substances and/or molecules such as pharmaceutical drugs or derivatives thereof, and the like, as well as combinations of the above. The emitted radiation from the radiolabeled analyte(s) can be detected in vivo from tissue in target or localized region(s) in the body. This detected and monitored radiation can provide information on one or more of the metabolic activity in the localized region, tissue, or cells, the pharmacokinetics/pharmacodynamics of a corresponding non-radiolabeled analyte or substance, the likelihood of the uptake and the retention of certain chemotherapeutic drugs in the localized region or tissue, and/or a substantially real-time or kinetic analysis of the biological status or metabolism and/or proliferation of malignant and/or normal cells in the localized tissue or region at desired points in time. The radiolabeled version of the non-radiolabeled analyte can be formulated to have the same or substantially similar pharmacological or biochemical activity as the parent analyte.

Such systems and methods can be used to obtain and/or analyze data or physical quantities from the living body to provide intermediate data that may be provided to a clinician or researcher for further consideration. The detection can be carried out at multiple sites about a region of interest or at a plurality of different spaced apart sites in the body. The systems, methods, and operations of the present invention may be carried out to monitor for longer times over conventional systems, the biological or physiological impact of a selected therapy (or combinations of therapies) on a target disease, disorder, or condition of the body (pharmacodynamics) in addition to the in vivo levels, activity, retention, uptake, delivery, etc., of one (or more) therapeutic agents (pharmacokinetics).

Certain embodiments of the systems and methods of the present invention may be used with any analyte which can be radiolabeled or made radioactive, including, but not limited to, as noted above, endogenous material that can be radiolabeled and re-introduced to the subject, or exogenous material. As also noted above, suitable analytes can include radiolabeled versions of nuclides, pharmaceuticals and derivatives thereof, antibodies, antigens, proteins, peptides, amino acids, nucleic acids, glucose and metabolites and derivatives thereof. The radiolabeled analyte may be a genetically engineered substance, which has a site-specific or tumor or tissue specific delivery target, a differentiation antigen, or an analyte which can be activated upon delivery to a particular region or tissue or which can otherwise be locally "activated" or targeted. The radiolabeled analyte or substance may be selected based on its presence or expression, i.e., a radiolabeled marker associated with a disease or cancer in the region or at the targeted site, such as an over or under expression of an antigen, antibody, peptide, protein, enzyme, amino acid or other endogenous analyte, or other genome or phenotype(s) criteria or behavior. Thus, it is contemplated that radioactive monitoring for dynamic amounts of the marker or antigen expression can provide valuable internal real time or dynamic information about cellular activity.

The term "glucose derivative" includes glucose molecules with a modified glucose chemical structure that is biocompatible and can be biochemically processed by the body. Examples of glucose derivatives include, but are not limited to, dextraglucose (D-glucose), and 2-deoxyglucose (2-DG).

Examples of marker or expression-based evaluation of antigens/antibodies (which may be radiolabeled) include those used in cancer evaluation and/or treatment. Examples of tumor-associated antigens of interest may include the CD-20 antigen (on B lymphocytes) for which treatment may include agents having antibodies to the CD-20 antigen and human epidermal growth factor (HER2) associated with some breast tumors. It is noted that HERCEPTIN may be radiolabeled and is currently approved for HER2 breast cancer treatment.

It is contemplated that other biomaterials may also be suitable to carry out operations of the present invention. Examples of potentially suitable biomaterials may include, but are not limited to, mixed cultures containing tumor cells and blood-derived lymphocytes (which may be from the patient him or herself) to produce cytolytic T lymphocytes (CTL) (or CTL clones or autologous CTL), that lyse the autologous tumor cells (which may be used in connection with melanoma, renal, bladder, head and neck carcinomas, non-small lung cancer, and the like). Other potential antigens/antibodies of interest include MAGE-1, MAGE-3, BAGE, GAGE-1, and GAGE-3. See, e.g., UCL Christian de Duve Institute of Cellular Pathology, *Ludwig Institute For Cancer Research*, URL www.Icp.ucl.ac.be/report95/licr95.html.

In any event, the radiolabeled analyte may be combined with other substances and formulated for the desired delivery (injection, intraveneous, subcutaneous, etc . . . ) to produce the desired composition and/or bolus. In certain embodiments, the analyte can be formulated into a liquid solution. The solution can be formulated to dilute the concentration of the radiolabeled constituent or ingredient or to provide other desired biocompatible materials. Examples of suitable radiolabeled or radioactive substances will be discussed further below. The radioactive or radiation label can be gamma, alpha, or beta radiation, depending on the application.

The term "subject," according to the present invention, includes subjects belonging to the animal kingdom, and are preferably mammalian subjects (e.g., humans, canines, felines, bovines, caprines, ovines, equines, rodents, porcines, and/or lagomorphs), and more preferably are human subjects.

In certain embodiments, the analyte is a therapeutic pharmaceutical drug or antibody that is configured to treat a selected physiologic or biologic condition, impairment, or disease. The radiolabel can be selected or formulated to be substantially transparent so that the non-radiolabeled version and the radiolabeled version of the same analyte has substantially the same biochemical activity in the body and/or the radiolabeled version does not interfere with the intended therapeutic, physiologic, or biologic reaction in the body. As such, the radiolabeled version of the analyte (or drug or antibody) can be such that the radiolabeled version biologically functions or is biochemically processed in substantially the same manner as a corresponding non-radiolabeled version. In certain embodiments, the radiolabel does not inhibit or interfere with the natural breakdown or reaction of the analyte and/or its constituents in the body.

The radiolabel can be a beta radiation label, wherein the beta radiation label is substantially transparent to the intended therapeutic physiologic or biologic reaction of the drug in the body. Examples of beta-emitting radioactive labels include one or more of C-14, P-32, P-33, I-131, Kr-85, Xe-133, Tl-201, Ga-77, F-18, Cs-137, Ca-45, Ca-47, Co-60, Fe-59, Hg-203, Ni-63, Rb-86, Ru-106, Ag-110m, Na-22, S-35, Sr-90, Tc-99, H-3, Zn-65, Cu-64, O-15, N-13, and other positron emitters and beta particles used therapeutically.

In certain embodiments, the radioactive label is C-14. Carbon is widely used in drug evaluations and C-14 has a suitably long decay half-life and an acceptably short biological half-life for most drugs of interest. The C-14 label can thus be used with a wide variety of pharmaceutical products and is not limited to one particular drug or a small number of drugs, thereby allowing for a relatively wide, evaluation model or protocol for available therapeutic agents.

In certain particular embodiments, the radioactive label may be selected for its ability to (a) be used across a wide variety of therapeutic drugs, (b) generate sufficient signal in the localized tissue in the body to allow for dynamic and/or quantitative monitoring over a desired response window (of between at least about 5 minutes–30 minutes, and typically at least 30 minutes –1 hour), and (c) have a biocompatible biological half-life with a suitable shelf-life. This is in contrast to conventional evaluation methods, which, as discussed above, employ various radioactive substances. For example, PET-based methods use radionuclides that emit positrons. F-18 is one common radionuclide used in these types of procedures; however, fluorine containing drugs or therapeutic products are not common. Other radioactive labels may also only be useful in a limited number of drugs while others may have an unduly short half-life that, in turn, can limit the amount of data or the width of the evaluation window over which data can be taken. Still other radioactive labels may not generate sufficient concentration or signal levels to allow quantitative evaluation in the body (to generate unfavorably weak signals).

Turning to FIG. 1, in the embodiment shown, a subject can be undergoing treatment for a cancerous tumor. A quantity of a radiolabeled or radioactive substance (alone or combined with other ingredients or substances) is administered to the subject (Block 100). As shown, the quantity and/or radioactive intensity or concentration of the substance or analyte may be such that it acts as a pre-diagnostic test dose, rather than a therapeutic dose, which is delivered in advance of the therapeutic dose to assess or predict the clinical efficacy of a treatment prior to delivery of the treatment itself. The radiolabeled analyte or substance can be delivered either systemically, locally, or both (Block 105).

In certain embodiments, a small test or diagnostic dose of a radiolabeled substance or analyte such as a C-14 labeled analog of a chemotherapy drug or pharmaceutical can be administered to the subject proximate in time (and/or before) a treatment session (for which a non-radiolabeled version of the pharmaceutical can be used to therapeutically treat the cancer). As used herein, a "small" dose means a dose which is less than a therapeutic dose. The detected radiation can provide kinetic or predictive information about the likelihood of the success of the treatment and allow a potential clinician to proceed with the planned treatment, delay the treatment, exclude one or more of a treatment, or select a different pharmaceutical agent for treatment. In certain embodiments, the radiolabeled dose can be sized in an amount which is about a 0.1%–60%, and can be about 1–10% of that of a corresponding therapeutic dose.

In certain embodiments, the radiolabeled substance or analyte can have a concentration of about 100–500 nanocuries/cc to about 1–10 millicuries/cc (mCi/cc) (the latter typically being more suitable for direct injection at the target site). In particular embodiments, the concentration may be from between about 10 $\mu$Ci ($10^{-6}$ Curies) to about 1 mCi. The dose may be sized according to weight (children may receive doses in the lower portion of the range with large adults receiving doses at or above the typical range).

In certain embodiments, the concentration can be selected such that it corresponds to whole body doses of about 1–10 milliGray corresponding to concentrations conventionally used for nuclear medicine scans. In other embodiments, the radiolabeled analyte or substance can be systemically delivered at higher radiation concentrations where it is targeted for the target site (selective target or site specific activation formulations such as antibodies). In these embodiments, the tagging system may be designed to deliver a total dose on the magnitude of about 10–99 Grays.

Systemic deliveries may be made by any suitable mode such as via IV introduction into the vein of the subject. Local deliveries may be made by injections from a lumen of a syringe or via introduction through a transcutaneous catheter configured to direct the radiolabeled substance substantially directly to or proximate to a target region.

Turning again to FIG. 1, the radiation emitted from local tissue (such as a cancerous tumor) is detected in vivo. The detected radiation can be analyzed over a selected response period, cycle, or time(s) (Block 110). For example, a radiation sensor can be operably configured such that it is at least intermittently or periodically activated and may be continuously operated or monitored to relay information to a clinician over a time which is proximate to the administration of the radiolabeled analyte to about 24 hours later. In certain embodiments, the radiation is detected every 30 seconds to every 15 minutes during a portion of the detection cycle when the detected radiation values change from the prior reading. This shortened interval may be in the early portion of the monitored response cycle (such as in the first 10–60 minutes after initiation of the administration of the radiolabeled analyte). The activation or detection interval can be automatically extended when there is little fluctuation between incremental readings (based on an average between more than two readings or the values between two consecutive readings). The adjustment between detection intervals may be beneficial for some embodiments, which may employ wireless implantable sensors to preserve power (and extend operative life). Examples of parameters which can be monitored or analyzed will be discussed below.

In certain embodiments, which may be particularly suitable for continuous mode monitoring (but may also be used otherwise), the radiation levels can be detected and summed until the completion of the test or at the end of the evaluation/response window. The first derivative can be mathematically calculated or determined (to provide data on the rate of change of concentration) (FIG. 6E) or the lineshape, profile, or curve of parameters associated with the time-dependent measurements can be analyzed to yield the radiation level in the target issue over time.

Referring again to FIG. 1, a therapeutic treatment type or administration time can be selected based on the analyzed data associated with the detected radiation (Block 120). For example, based on the detected radiation over the response cycle, a clinician can have access to individualized information concerning the status of the bioactivity of the local tissue, the likelihood of the receptiveness to a desired therapeutic treatment, and/or the likelihood of a suitable uptake and retention of the desired therapeutic agent based on the uptake and retention of the administered radiolabeled analyte. As such, a clinician can select which particular chemotherapeutic agent (or agents) to administer to the subject at that point in time. Similar evaluations can be carried out periodically over the treatment cycle (typically 2 or more different chemotherapy administrations may be performed over a period of weeks and months). In certain embodiments, the radiolabeled analyte can be administered just proximate to (typically prior to) a planned chemotherapeutic treatment session. In certain embodiments, the therapeutic administration can be performed in less than 24–48 hours (and before any additional intentional or unintentional perturbation) from the monitored response cycle to reduce the likelihood that the bioactive nature or status of the tissue and, thus, the predicted response, will shift substantially.

In certain embodiments, the clinician may determine that conditions are unfavorable for a therapeutic treatment and delay or exclude the therapeutic treatment until local conditions improve (thereby reducing the introduction of cytotoxic drugs when the treatment outcome is likely to be unfavorable). As such, the data obtained may be used to evaluate whether to exclude certain potential therapies (including changing or prescribing alternative drug therapies) as it may not be indicated to be a viable treatment for that individual, or to postpone the treatment for a more favorable time.

As the detected radiation values can be monitored over time to determine or assess the present status (i.e., substantially real-time) of the localized tissue or evaluate the biokinetic or metabolic or activity response and/or the physiological or biological status of the local tissue, the method can be repeated at desired intervals, such as proximate in time to each therapeutic treatment over the active treatment period (Block 130). The data can be obtained several times during a desired monitoring period (such as twice, thrice, four or even more times). In certain embodiments, the kinetic data or radiation values of interest can be obtained before and after a particular treatment or active treatment session. Further, a radiolabeled analyte may be administered before and after a therapeutic treatment to facilitate the detection in vivo of localized response data. This repeat administration of a radiolabeled analyte may increase the detectability of the signal (increase the signal strength) in the body, depending on the length of the therapeutic treatment, and/or may provide data regarding the state of the tissue after administration of a therapeutic agent and/or at a desired point in time.

When selecting the therapeutic treatment, the clinician can consider a plurality of different pharmaceutical treatments and/or cytotoxic agents based on the evaluated condition or response of the tumor of the subject (Block 125). In addition, combination therapies can be considered to attempt to generate increased receptiveness. For example, heat or an externally generated and directed radiation dose or other combination therapy modality may be desirable to improve the tissue receptiveness. In any event, each of the chemotherapeutic treatment agents or combinations can be evaluated to select those types that align with or match the predetermined associated desired biological and/or physiological conditions (such as cell proliferation or sensitivity associated with uptake and/or retention of the radiolabeled analyte in the tissue) with that of the subject to yield increased clinical effectiveness.

Thus, in certain embodiments, the methods and systems may be used to determine the timing and type of treatment to administer to a subject so as to promote clinical efficacy based on a dynamic or substantially real-time understanding of the physiological or biological status of the targeted tissue. Other embodiments can evaluate the metabolic activity of the subject and/or to study pharmacokinetics/pharmacodynamics. For example, the data can be obtained and evaluated in a manner that provides information on the influence and/or impact on metabolic activity that certain therapies, activities, foods, vitamins, food supplements, or environmental exposures, may have on the target region of interest.

The system can be configured as a minimally invasive device that can, in certain embodiments, employ an implantable wireless or telemetric based radiation sensor. In other embodiments, the radiation sensor(s) can be a catheter or probe based device and placed transcutaneously or inserted via a cavity or lumen to the site of interest where a fiber optic (or bundle of fiber optics) acts as the sensor. Exemplary sensor and system configurations will be discussed further below.

Figure 2A:
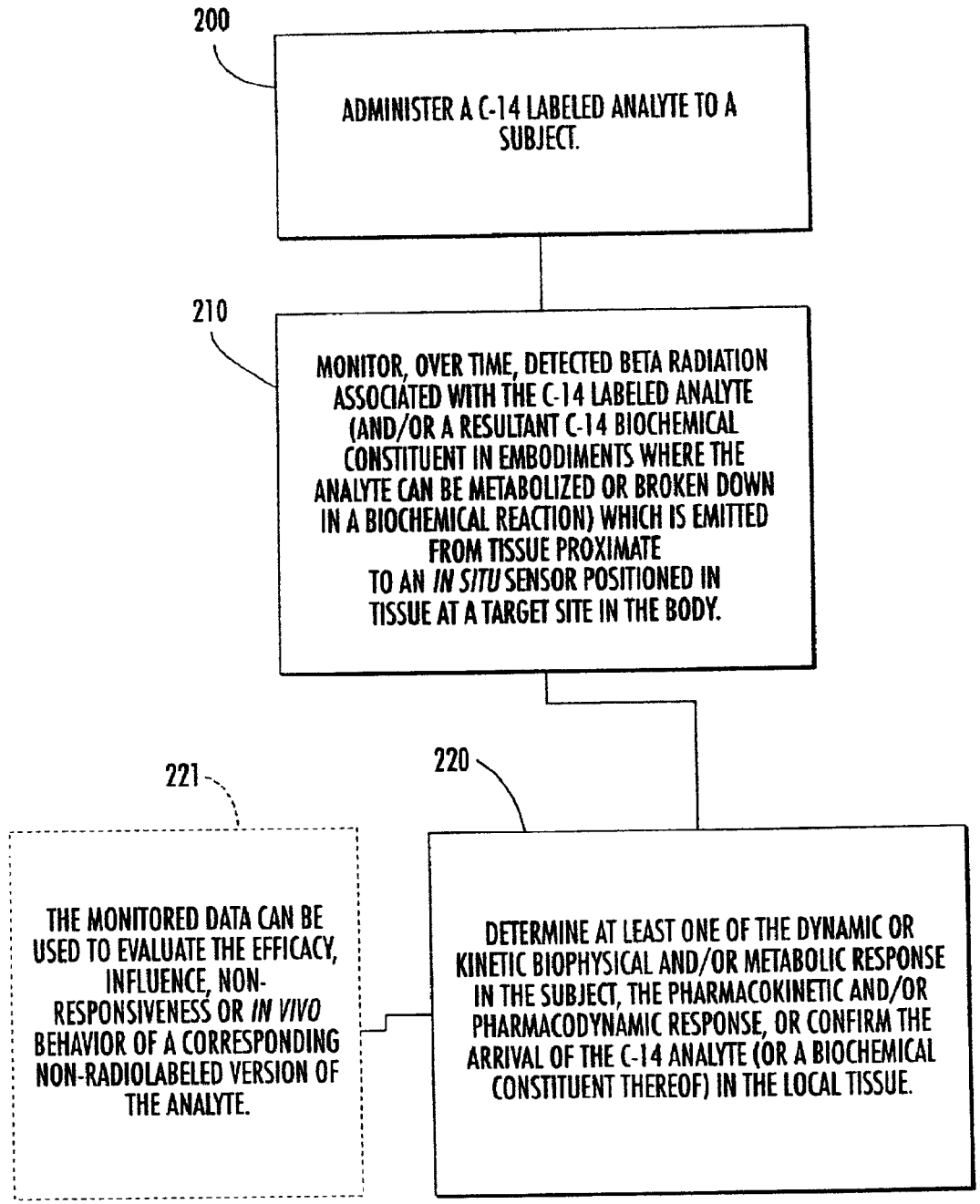
FIG. 2A is a block diagram of another method of operation according to embodiments of the present invention.

FIG. 2A illustrates that, in certain embodiments, a C-14 labeled analyte can be administered to a subject (Block 200). The beta radiation emitted from local tissue in the subject responsive to the administered radiolabeled analyte can be detected in vivo from a radiation sensor positioned in situ in tissue proximate to a target site in the body. The detected radiation can be monitored at desired times in a monitoring period (typically generating a signal or over time) (Block 210). At least one of the dynamic or kinetic biophysical response or activity (including the physiological or biological condition or response or activity) of the subject or the pharmacokinetic and/or pharmacodynamic activity associated with the radiolabeled analyte can be monitored or determined or the monitored data can confirm that the radiolabeled analyte (or biochemical constituent thereof) is delivered to the intended targeted tissue in the subject (Block 220). The data from the monitoring step can be used to assess desired in vivo response or activity such as, for example, the clinical performance, biophysical response or non-response of the subject, or efficacy of a non-radiolabeled counterpart analyte (Block 221).

The detected radiation may also be calibrated to quantitatively measure the radiation dose received at the tissue. The calibration can be based on signal strength or radiation counts detected based on in vitro values of levels in tissue or otherwise defined by experimental or clinical evaluations to correlate the signal to the amount of radiation present in vivo.

In certain embodiments, the radiolabeled analyte corresponds to a radiolabeled version of a (non-radiolabeled) drug in the discovery phase of development or evaluation (such as before or during clinical or pre-clinical trials) and is administered to evaluate the pharmacokinetics and/or pharmacodynamics thereof.

Figure 2B:
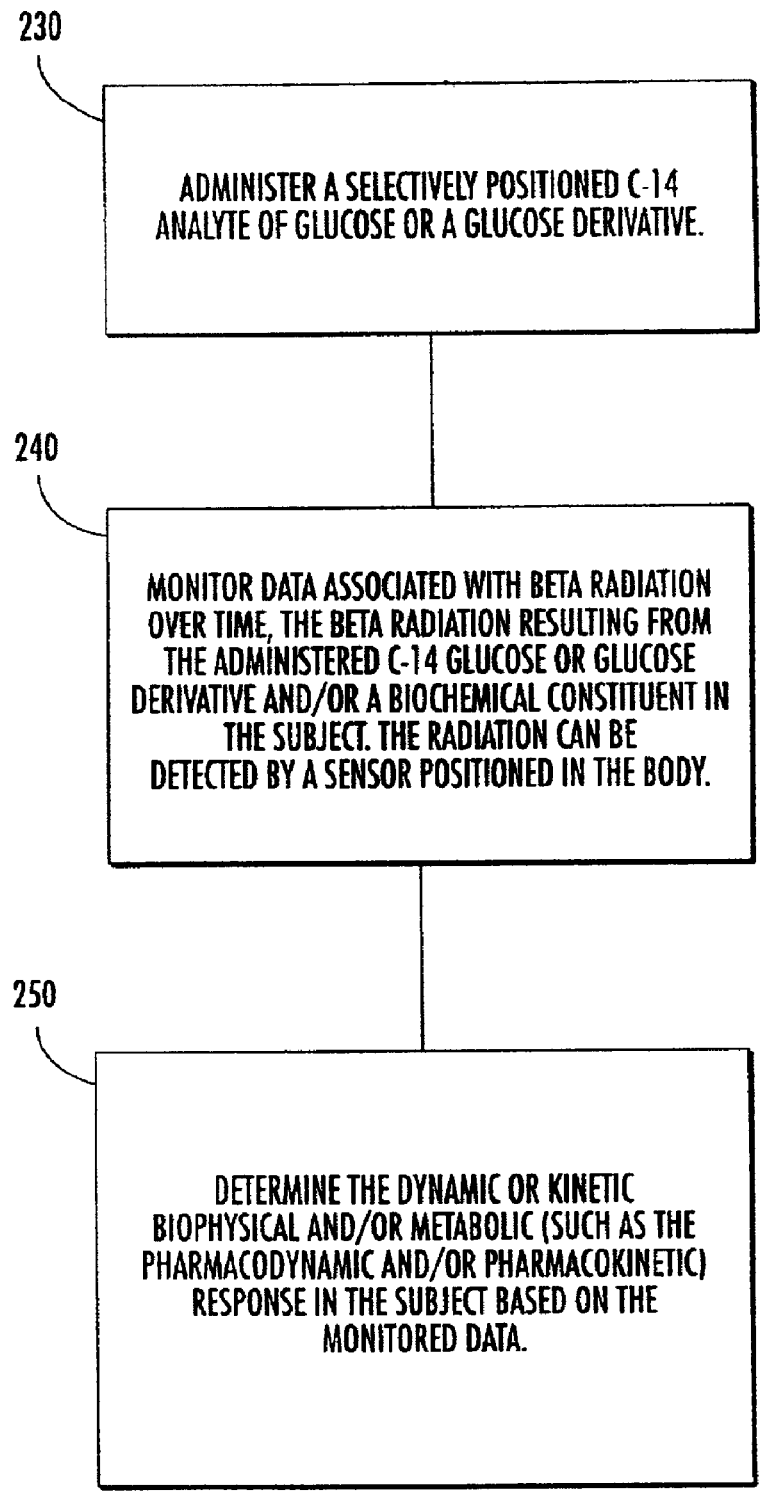
FIG. 2B is a block diagram of an additional method of operation according to embodiments of the present invention.

FIG. 2B illustrates that, similar to the operations described in FIG. 2A, the radiolabeled analyte is a C-14 labeled glucose molecule, also known as [$^{14}$C]glucose. The [$^{14}$C]glucose can be monitored as it proceeds through a biochemical reaction and breaks into metabolic constituent components in the body. The C-14 labeled glucose molecule may include glucose molecule derivatives such as, but not limited to, 2-deoxyglucose (2-DG), dextra-glucose (D-glucose), or other radiolabeled glucose molecule derivative suitable for in vivo administration to a subject (Block 230). Data associated with the beta radiation corresponding to the [$^{14}$C]glucose, and/or glucose derivatives, as well as one or more of its radiolabeled metabolic or biochemical constituents in the subject, which is emitted from targeted localized tissue, is obtained and monitored over time (Block 240). The dynamic kinetic biophysical and/or metabolic (that can include one or more of the pharmacodynamic or pharmacokinetic) response in the subject can be determined or evaluated based on the obtained data (Block 250).

The position of the C-14 label on the glucose molecule and/or a glucose derivative molecule can be selected based on one or more of a desired biochemical breakdown in the body, the desired residence time (longer or shorter) in the body, and/or the desired exit pathway of the C-14 radiolabel from the body. It is has been suggested that [3-$^{14}$C]- and [4-$^{14}$C] versions may release $^{14}$CO$_2$ earlier in the biochemical reaction process while [1-$^{14}$C]-, [2-$^{14}$C]-, and [6-$^{14}$C]- may release $^{14}CO_2$ later in the process cycle. See, e.g., Hawkins et al., *Cerebral glucose use measured with [14C] glucose labeled in the 1, 2 or 6 position*, American Physiological Soc., C-170–C173 (1985)(diagramming the fate of C-14 in various positions of the carbon bonds of a glucose molecule on metabolism by glycoslysis and the tricarboxylic acid cycle). See also, Hamkens et al., *PET in Clinical Oncology*, pp. 55–65, Edited by Wieler et al. (Springer, Darmstadt, Germany, 2000) (discussing, describing, and comparing, the biochemical pathways of the metabolism of glucose and FDG (denotation of the essential enzymes v.i.)). The contents of these references are hereby incorporated by reference as if recited in full herein. Thus, embodiments of the present invention can selectively position the C-14 label to a desired carbon site on the glucose molecule.

In certain embodiments, the radiolabel on the glucose or glucose derivative molecule may be expelled from the body based on what constituent component the C-14 metabolizes into or biochemically breaks down into, so that is may be expelled either via respiration (via $CO_2$), incorporated into the cell, and/or excreted in fluid. As noted above, selectively positioning the C-14 label on a carbon site on the glucose molecule can cause the body to release the radiolabeled constituent(s) earlier or later in the biochemical process (earlier discharge may also provide faster discharge of the radioactive component from the body). Monitoring the activity associated with the digestion or metabolized glucose may yield important information on the status of the localized tissue or tumor site. In contrast, 2-DG, is not metabolized by cells and may typically remain in the body for several hours to 1 day before it is de-phosphorylated and excreted.

Metabolized glucose data may be analyzed in a relative assessment or in an absolute assessment. For example, the signal data can be compared to absolute threshold data established from population norms (which may be segmented by population age or gender or disorder) or to relative data either normal or tumor data taken on the subject previously. The data can be used in a quantitative manner to establish concentration, quantity, rates (uptake and discharge), speed of the biochemical cycle, and the like.

In certain embodiments, two different response profiles can be generated, before and after certain therapies or temporally spaced apart in time, or with different analytes. For example, two response profiles can be taken with different radiolabeled analytes such as, but not limited to, both the [$^{14}$C]glucose and the C-14 labeled 2-DG analyte. One or both types of glucose-based data analysis may be able to provide information glycolysis and/or the tricarboxylic acid cycle. Such information may indicate normal or abnormal cellular behavior. For example, the information may be used to assess when a tumor or site is aerobic (oxygen rich) or anaerobic (oxygen deficient). It is known that tumors have abnormal glucose metabolic activity. Growing tumors can digest or take-in increased amounts of glucose relative to normal tissue (i.e., are hypermetabolic). Thus, the presence of increased amounts of C-14 glucose during the biochemical process may be representative of a growing, aerobic, or active tumor. Such information may be able to be used to assess tumor receptiveness to a particular treatment such as a cytotoxic agent and/or to indicate that the target region comprises healthy tissue.

In certain embodiments, operations carried out according to the present invention can evaluate whether a given therapy has altered, disrupted, inhibited, or impaired, or promoted, the glycolysis biochemical process. This alteration may be identified earlier in a treatment cycle before glucose uptake is substantially altered, potentially providing earlier indications of therapeutic efficacy or influence.

Figure 2C:
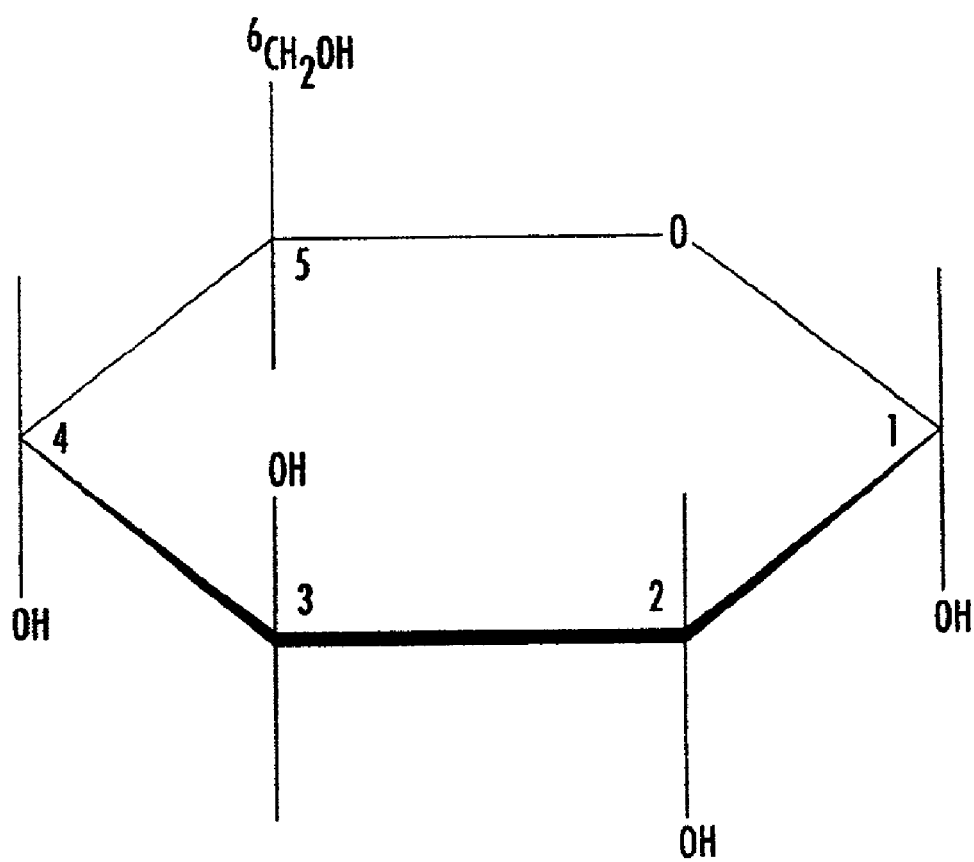
FIG. 2C is an example of a glucose chemical structure that may be radiolabeled according to embodiments of the present invention.

FIG. 2C illustrates an exemplary glucose molecule. The glucose may be in an alpha-pyranose form. Of course, the glucose may also be formulated in other biocompatible forms as is known to those of skill in the art. As noted above, one or more of the carbon sites in the glucose molecule may be replaced with the C-14 tag as desired. Due to the body's ability to metabolize glucose, a plurality of serially administered and/ or successive doses (separated over desired time intervals) of the radiolabeled analyte may be used to evaluate a patient's metabolic activity or tumor status. In certain particular embodiments, the C-14 label is selectively chosen for a particular carbon position, such as in positions C-1, C-2, C-3, C-4, C-6 or combinations thereof. In particular embodiments, the C-14 label can be located at C-3 or C-4 so as to promote metabolization with $^{14}CO_2$ discharge earlier in the biochemical process.

Figure 2D:
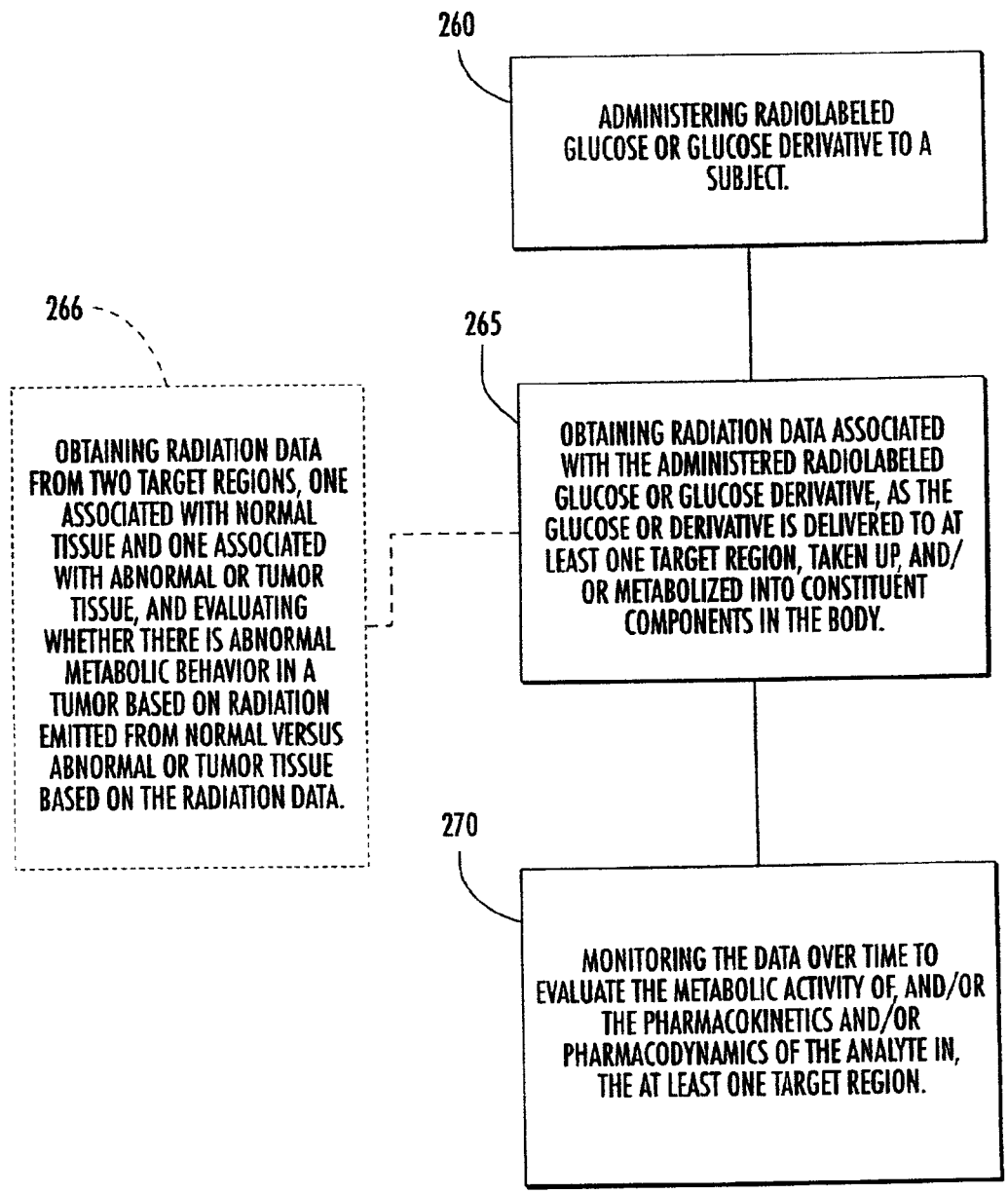
FIG. 2D is a block diagram of another method of operation according to embodiments of the present invention.

FIG. 2D illustrates a series of operations that may be carried out to obtain data of metabolic activity according to embodiments of the present invention. As shown, radiolabeled or tagged glucose or (a biocompatible) glucose derivative is administered to a subject (Block 260). Data associated with the administered radiolabeled glucose and/or glucose derivative is obtained as the radiolabeled glucose or glucose derivative is delivered to at least one target region and is taken up in localized tissue, and/or metabolized into constituent components in the body (Block 265). The data can be monitored over time to evaluate the metabolic activity, the pharmacokinetics and/or pharmacodynamics of at least one target region (Block 270). The data may relate to the metabolic status of a tumor or its biochemical metabolic activity. In certain embodiments, data can be obtained from two different target regions, one associated with normal or non-diseased tissue and the other associated with abnormal or tumor tissue. Data of the normal versus abnormal or tumor tissue can be obtained and compared as the radiolabeled glucose and/or glucose derivative is taken-up, metabolized, processed and/or transformed, by the body into constituent chemical components to assess whether there is abnormal or altered behavior or activity in the tumor or abnormal tissue (Block 266).

In any event, whatever methods of operation and/or analyte selected, the data can be obtained at discrete points in time and compared to generate a relative assessment of biochemical or metabolic change, efficacy or inefficacy in response to a therapy, and the like. In other embodiments, the data can be used to generate absolute or quantification values of the metabolic activity and/or radiation level at the target site(s).

In certain embodiments, data can be collected from a plurality of different target sites. For example, but not limited, the data can be obtained proximate to (near, adjacent, or in) tumor tissue and proximate to (typically in) normal tissue. In addition, multiple "normal" and/or "target or abnormal" tissue sites of interest may be concurrently monitored.

The in vivo detected beta radiation corresponds to radiation emitted from localized tissue or regions. The detected radiation is attributed to the uptake and/or retention of the analyte at the localized tissue at a certain point in time or at certain points over time. Selected parameters associated with the detected radiation can be monitored. The selected parameters can include one or a plurality of various parameters such as the flux, rate or acceleration of change, and/or a parameter having been identified as predictive of a desired therapeutic outcome. Examples of selected parameters will be discussed further below.

Figure 3:
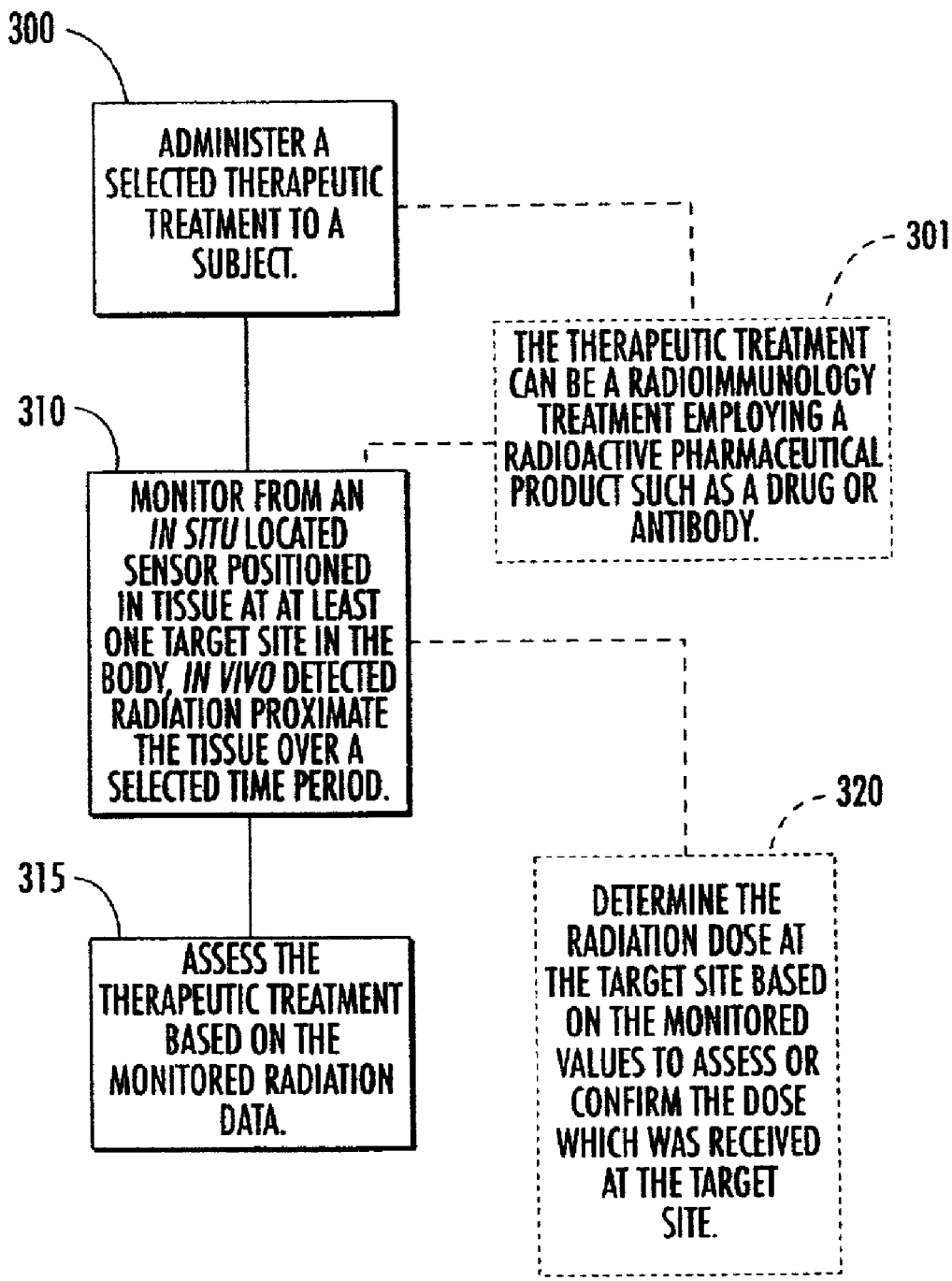
FIG. 3 is a block diagram of an additional method of physiologic or biologic evaluation according to embodiments of the present invention.

Referring now to FIG. 3, in certain embodiments the present invention can act as a radioimmunology radiation dosimeter using quantification of measured or detected internally administered radiation via the localized sensor. To begin, a selected therapeutic treatment can be administered to the subject (Block 300). The therapeutic radiation treatment may be an internally administered or radioimmunology treatment that may include gamma, beta, or alpha radiation (Block 301). The therapeutic radiation treatment can be delivered systemically or locally as described above. The systemic delivery may also include the administration of radioactive genetically engineered substances which target a cancerous tumor or diseased or organ or tissue of interest. The radiation can be monitored by an in situ sensor that is positioned in tissue in a target site in the body. As such, the radiation proximate to the target tissue is detected in vivo, (including adjacent to or within the tissue of interest) and is monitored over a selected time period (Block 310). The therapeutic treatment can be assessed based on the monitored radiation data (Block 315). The assessment can include determining whether the tissue exhibits a change in biocellular, biokinetic, or biochemical process, or exhibits a desired response, uptake, retention, signal strength, or a non-response to the selected therapy. In radioimmunology therapies, the amount of radiation which reaches the target site (the desired treatment destination) can be quantified. That is, the radiation dose can be quantitatively evaluated based on the monitored detected values to assess or confirm that a desired (typically therapeutic) dose at the diseased or targeted tissue was received at the target site and/or that the appropriate lower dose was received away from the targeted site (Block 320).

The term "tissue" includes all substances in the body, e.g., an aggregation of morphologically similar cells and intercellular matter performing one or more functions in the body (such as, but not limited to, muscle, arteries, veins, vessels, tissue, bone, bone marrow, and the like) as well as serum, interstitial fluid or liquid. The liquid or fluid detection may be more typically measured with a fiber version of a detection or senor probe rather than a non-fiber version of the sensor.

In certain embodiments, a plurality of radiation sensors or sensing probes can be positioned about different locations in the targeted region to evaluate the distribution of the radiation dose across this region. In other embodiments, at least one radiation sensor can also be positioned in normal tissue, sensitive tissue, or adjacent the target site to monitor the amount of radiation which is delivered thereto to attempt to reduce the likelihood that radiation is overdosed in undesirable amounts to undesired locations. This information can allow clinicians to refocus, adjust, or revise the strength or type of the treatment (during or after a therapy session). For example, a number of pharmaceutical products can be formulated into a corresponding radiolabeled version, which allows for the particular pharmaceutical to be analyzed locally in its radiolabeled form. The radiolabeled version has the same or substantially similar pharmacological activity as the parent drug or compound.

Further, C-14 radiolabeled drugs have been used in the past to evaluate its physiologic impact on a subject during regulatory reviews to analyze metabolic byproducts. Typically, these types of studies have used a scintillating fluid with urine or fecal samples or exhaled $^{14}CO_2$.

Examples of chemotherapeutic pharmaceutical products, which can be formulated with a C-14 tag, include antineoplastics such as alkylating agents, nitrogen mustards, nitrosureas, antibiotics, hormonal antagonists or androgens, antiandrogens, antiestrogens, estrogen/nitrogen mixtures, estrogens, gonadotroopin releasing hormones, immunomodulators, and other appropriate therapeutic agents. Other products not specifically listed may also be used as contemplated by embodiments of the present invention. Table 1 lists a few examples of products, which can be radiolabeled for cancer treatments according to the present invention.

TABLE 1

| Agent | Manufacturer |
| --- | --- |
| A. Alkylating agents | |
| 1. Myleran | GlaxoSmithKline (Glaxo) |
| 2. Paraplatin, platinol | Bristol Myers Squibb (BMS) |
| 3. Temodar | Schering |
| B. Nitrogen Mustards | |
| 1. Alkeran | Glaxo |
| 2. Cytoxan | BMS |
| 3. Ifex | BMS |
| 4. Leuderan | Glaxo |
| C. Nitrosureas | |
| 1. BCNU | BMS |
| 2. CCNU | BMS |
| 3. Gliadel wafer | Aventis |
| D. Antibiotics | |
| 1. Adriamycin | Pharmacia & Upjohn |
| 2. Blenoxane | BMS |
| 3. Idamycin | Pharmacia & Upjohn |
| 4. Mithracin | Bayer |
| 5. Mutamycin | BMS |
| 6. Novantrone | Immunex |
| 7. Rubex | BMX |
| 8. Fludara | Berlex |
| 9. FUDR | Roche |
| 10. Thioguanine | Glaxo |
| 11. Xeloda | Roche |
| E. Hormonal Antagonists | |
| 1. Nilandron | Aventis |
| 2. Teslac | BMS |
| F. Antiandrogens | |
| 1. Casodex | AstraZenaca |
| 2. Eulexin | Shering |
| G. Antiestrogens | |
| 1. Arimedex | AstraZenaca |
| 2. Aromasin | Pharmacia |
| 3. Femara | Novartis |
| 4. Nolvadex | AstraZenaca |
| H. Estrogen/Nitrogen mixture | |
| 1. Emcyt | Pharmacia |
| I. Estrogens | |
| 1. Estinyl | Schering |
| J. Gonadotroopin Releasing Hormones | |
| 1. Lupron | TAP |
| 2. Zoladex | AstraZeneca |
| K. Progestins | |
| 1. Megace | BMS |
| L. Immunomodulators | |
| 1. Ergamisol | Jansen |
| M. Miscellaneous | |
| 1. Camptosar | Pharmacia |
| 2. DTIC | Bayer |
| 3. Etopophos | BMS |

TABLE 1-continued

| Agent | Manufacturer |
|---|---|
| 4. Gemzar | Lilly |
| 5. Herceptin | Genetech |
| 6. Hydrea | BMS |
| 7. Intron A | Scherling |
| 8. Lysodren | BMS |
| 9. Navelbine | Glaxo |
| 10. Oncovin | Lilly |
| 11. Proleukin | Chiron |
| 12. Rituxan | IDEC |
| 13. Roferon A | Roche |
| 14. Taxon | BMS |
| 15. Taxotere | Aventis |
| 16. Velban | Lelly |
| 17. VePesid | BMS |

Figure 4A:
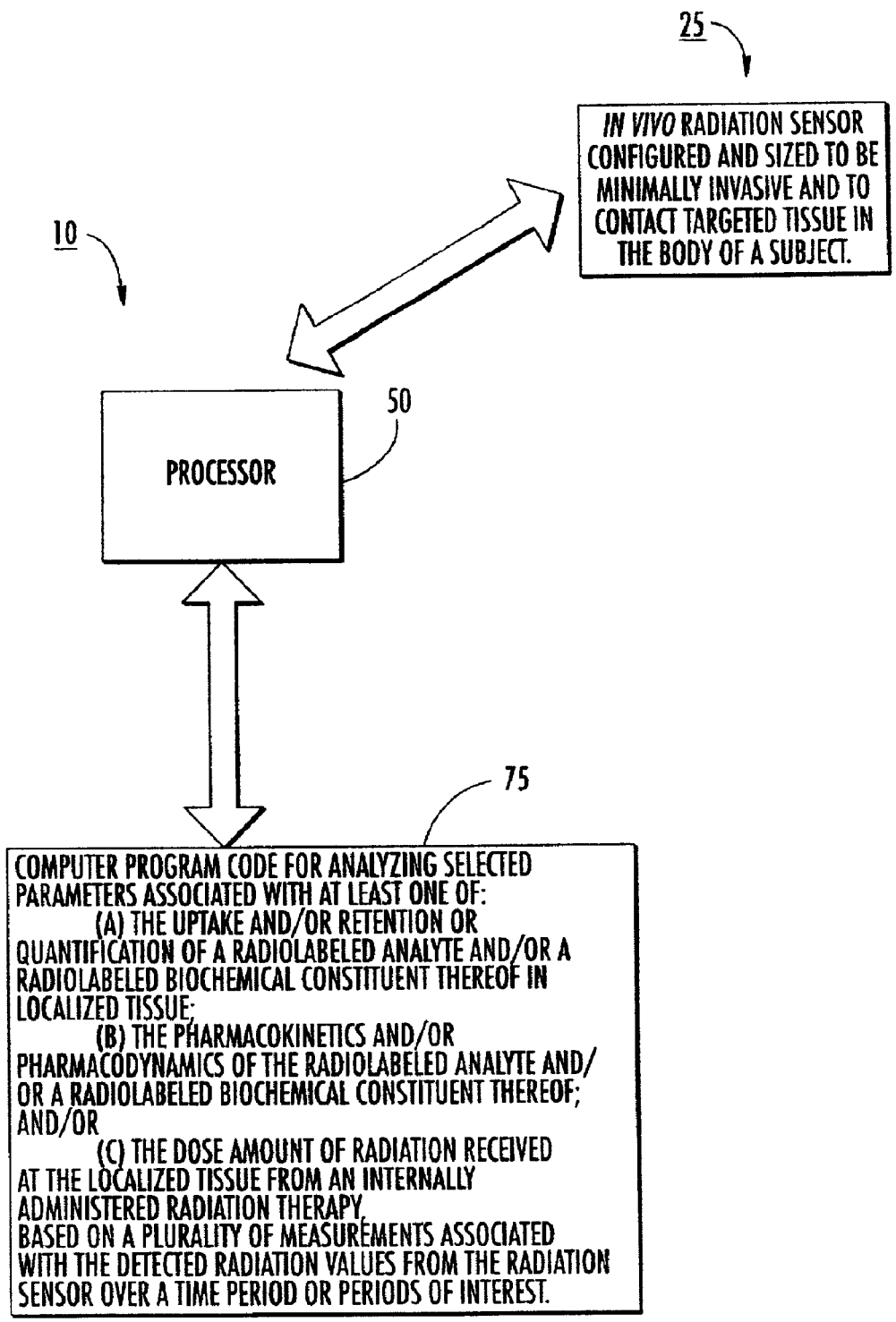
FIG. 4A is a schematic illustration of a system employing a wireless sensor according to embodiments of the present invention.

FIG. 4A illustrates one embodiment of a radiation detection system 10. As shown, the detection system 10 includes a radiation sensor 25 configured for in vivo wireless (telemetric) operation as it resides in a subject such that, during operation, the sensor 25 is proximate to or contacts tissue in the region of interest in the subject. The sensor 25 is operably associated with a processor 50 which can direct the activation of the sensor 25 and which can receive detected signals telemetrically transmitted from the sensor 25. The processor 50 is operably associated with computer program code or instructions 75 which analyze selected parameters associated with at least one of: (a) the uptake and/or retention of a radioactive or radiolabeled analyte and/or a radiolabeled biochemical constituent thereof in localized tissue; (b) the in vivo pharmacokinetics/pharmacodynamics of the radiolabeled analyte and/or a radiolabeled biochemical constituent thereof; and/or (c) the dose amount of radiation received at the localized tissue from an internally administered therapeutic radiation dose. Each of the selected parameters correspond to a plurality of values or measurements (such as one or more predictor variables taken from a time-dependent measurement profile) of a data signal associated with the radiation detected by the sensor 25 over a time period or periods of interest.

In certain embodiments, the sensor 25 is configured to be biocompatible and operable as it resides in the body for a period of at least about 1 day, and typically for at least about 1–3 weeks. In certain embodiments, the sensor 25 can reside in the body for about 1–3 months and is configured to be relatively non-invasive to the subject (so as to be biosealed to the environment, substantially non-irritating or unobstructive to the subject and/or so as to not unduly interfere with normal life activities).

Figure 4B:
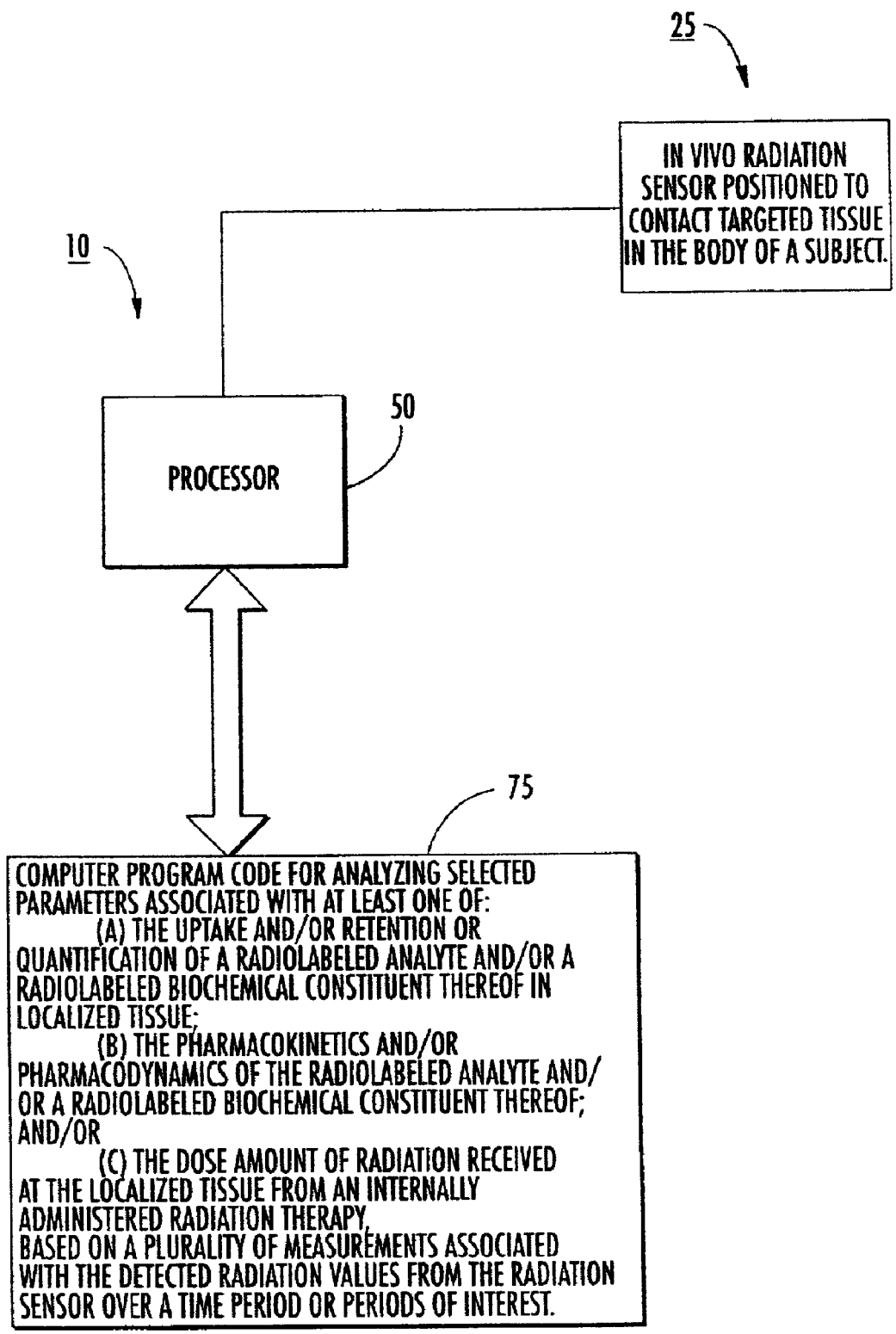
FIG. 4B is a schematic illustration of a system similar to that shown in FIG. 4A but with an alternate sensor/system configuration (wired) according to embodiments of the present invention.

As schematically shown in FIG. 4B, the sensor 25 can be mounted in a housing such as catheter and/or or be a fiber optic probe configured for insertion into the body and wired to an external operating system (represented by the solid lead lines drawn from the sensor to the processor). Such a system may be particularly suitable for short-term or acute positioning in the body and may be configured to collect data similar to the embodiment shown in FIG. 4A. The probe or catheter can be configured and sized to be positioned at the desired site intraoperatively, intraperitoneally (where the tumor or targeted tissue site is so located), subcutaneously, transcutaneously, or direct injection to the target site(s). In other embodiments, the catheter or probe can be guided or inserted into a cavity or natural lumen. In any event, the housing, probe or catheter is guided into the body until the sensor 25 is positioned in the desired location(s) in the body. In these embodiments, the sensor 25 may be hard-wired to (and powered by) the external system and activated by the processor 50 at desired monitoring times.

For certain embodiments, the system 10 may be a fiber-optic based radiation detector with the sensor probe comprising a plurality or bundle of fibers to provide intended surface areas for improved detectability. Light impeding cladding material may be placed over all but a desired tip portion of the fiber(s) to define a desired effective active detection surface area. One or more fibers (or a fiber bundle) may be employed. For example, a 2 mm fiber can be coupled directly to a channel multiplier head with about a 2.2 mm length exposed for active detection to define an effective active surface area of about 0.17 cm$^2$. Suitable active surface areas may be in the range of between about 0.10 cm$^2$–1 cm$^2$. Examples of fiber optic sizes include those having a diameter between about 2 mm to about 250 $\mu$m. Other sizes may be used depending on the application and number of fibers employed. As desired, an opposing end portion can be coated with a thin layer of aluminum or light shielding material to shield it from ambient light as needed, or measurements can be obtained in a light reduced room.

An example of an intraoperative surgical probe is described in U.S. Pat. No. 6,076,009, the contents of which are hereby incorporated by reference as if recited in full herein. In other embodiments, the sensor 25 can be configured as a wireless or telemetric implantable sensor 25 as discussed in relation to FIG. 4A above. Examples of suitable implantable sensors as will be discussed further below.

Figure 5A:
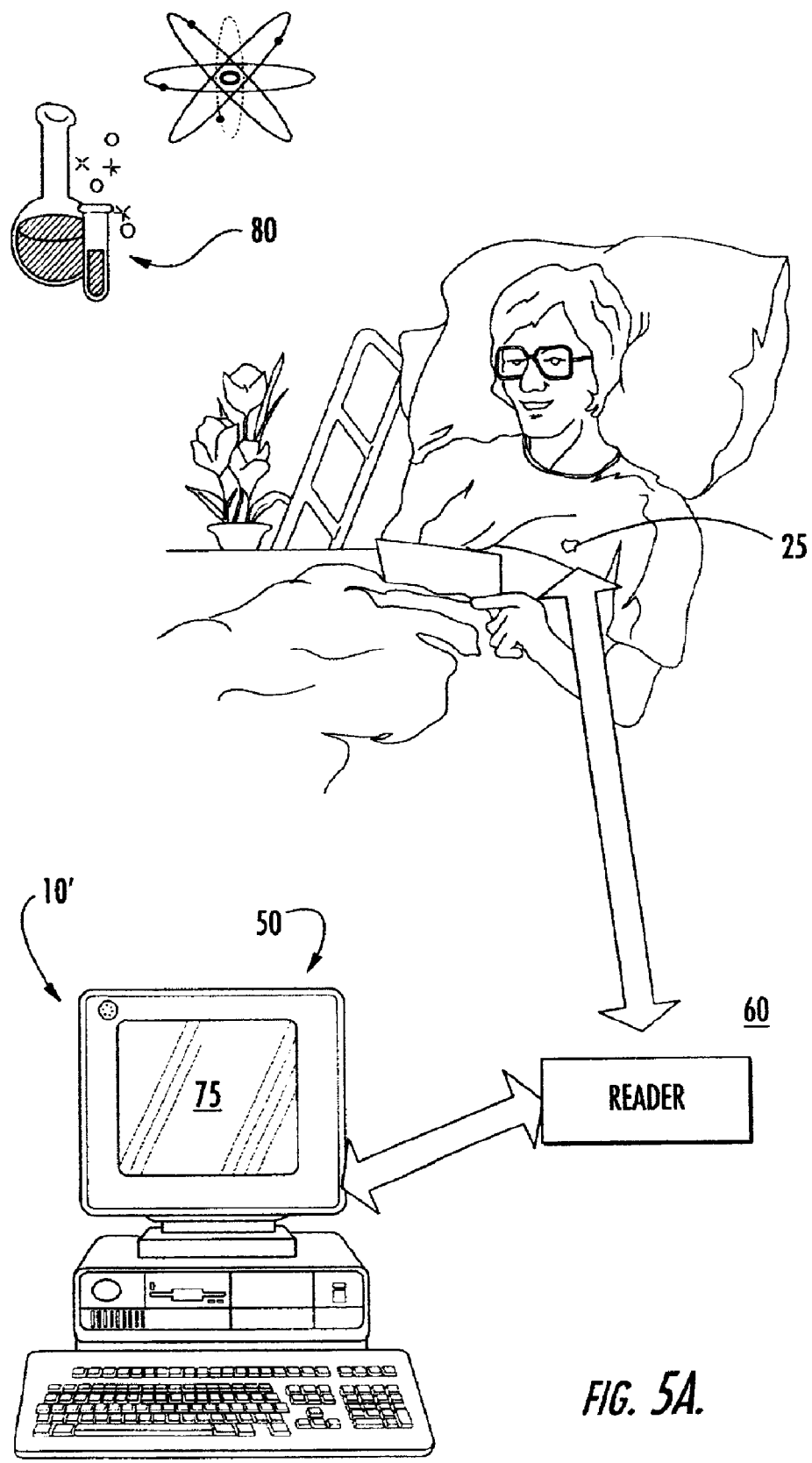
FIG. 5A is a schematic illustration of a radiation sensor located in vivo and associated monitoring system according to embodiments of the present invention.

FIG. 5A is a schematic illustration of other embodiments of the present invention. As shown, the sensor 25 is implanted in a subject at a desired target region in a subject so as to reside in the subject on a chronic basis for a desired period of time (typically between about 1 day–3 months). The system 10' includes a reader 60, which may be a wireless reader configured to wirelessly or telemetrically activate or initiate the activation of and reception of signals from the sensor 25 (the signals including data corresponding to the detected radiation). Co-pending U.S. patent application Ser. No. 09/407,359 filed Sep. 29, 1999, the contents of which are hereby incorporated by reference as if recited in full herein, includes descriptions of suitable telemetric configurations and sensors. As is also shown in FIG. 5A, the radiolabeled analyte 80 can be a liquid which can be formulated for injection into the subject.

Figure 5B:
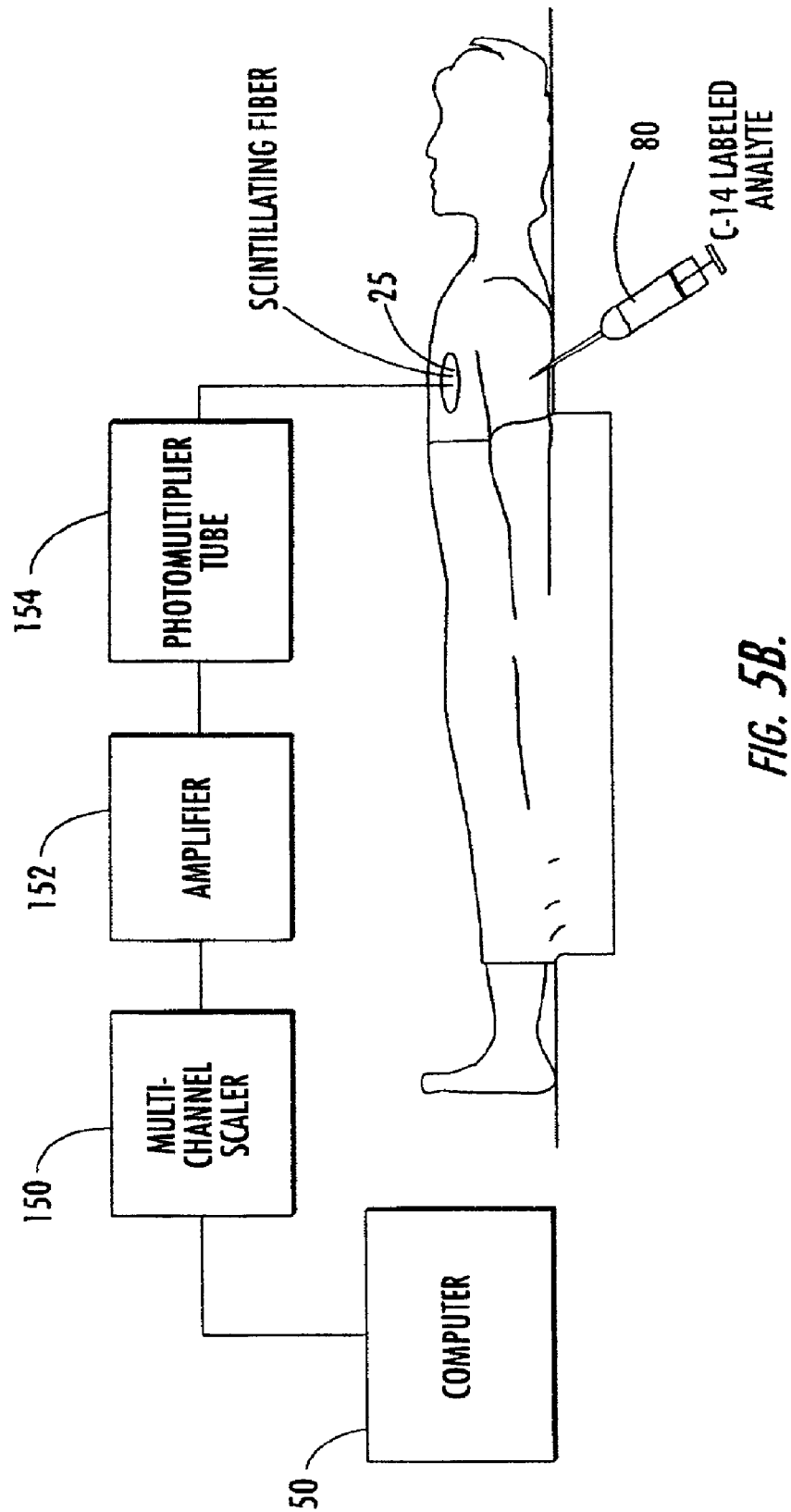
FIG. 5B is a schematic illustration of a detection system according to the present invention that can be configured as a transcutaneous, intralumen or intracavity catheter or probe-based sensor.

FIG. 5B illustrates another embodiment of the present invention. As shown, the radiolabeled analyte 80 may be formulated for systemic or direct injection, such as via syringe or IV injection. The system can include a photo multiplier tube (PMT) 154 in optical communication with the sensor 25 and an amplifier 152. The system may also include a multi-channel scaler 150 and a computer 50.

The present invention can acquire data associated with the detected radiation and generate at least one time-dependent measurement profile of the radioactivity in a localized region of the subject. The time-dependent profile can be analyzed to identify or quantify one or more predictor variables or parameters which capture desired information corresponding to one or more of the efficacy, performance, activity, response or status of the radiolabeled substance in the body and/the targeted or localized tissue.

Turning now to FIGS. 6A–6E, examples of parameters or predictor variables and time-dependent profiles which can be analyzed or monitored are illustrated. FIG. 6A illustrates that a monitored response time can be individualized such that measurements are obtained over a period during which the detected radiation is above a predetermined threshold value (the threshold value is represented by the broken line adjacent the X axis). In other embodiments, the response or monitoring period can be. pre-determined (such as between about 0.1–0.25 to 1–3 hours or to 24 hours or longer). As shown, radiation is detected over a period of time (t). The time at which the radiation is above a particular value (shown as the threshold value, but it may be at a higher value) can be defined as the time during which the local tissue is able to uptake, trap or accumulate or retain the radiolabeled or radioactive analyte ($t_{trap}$). The detected radiation may have a peak at a particular time in the response cycle ($t_{peak}$). In addition, the radiation may increase during a portion of the response cycle ($t_{inc}$) and decrease for a period of time thereafter ($t_{dec}$). The rate of increase or decrease or time to reach the peak or the lower threshold may also be calculated based on the monitored values. Further, the acceleration or deceleration or decay rate (either an average or at particular times during the monitored period) can be established.

For example, the energy from C-14 decay peaks at about 55 KeV. Generally described, in the time-dependent measurement profiles, each "count" or point in the profile or curve can correspond to a pulse of charge, and the pulse of charge can be quantified using a charge sensitive detector. In certain embodiments, signal to noise ratios can be enhanced in various ways, such as by allowing for signal integration over short time windows of about 1 μs so that dark counts are reduced. In certain embodiments, the time duration of the signal pulses can be about 10 ns or less.

One or a combination of parameters or appropriate predictor variables can be correlated or statistically evaluated to determine the impact on clinical outcome or performance in the body. As such, the parameter is predictive of a desired performance, response or status of the localized tissue in the subject (or in other embodiments of the delivery and/or the quantification of the amount of radioactive substance actually delivered to the targeted treatment site).

For example, if a subject has a relatively long trapping time, such that it is able to retain the radiation above a certain level for greater times (either absolute or relative) than previously or in comparable subjects or as established in clinical data, this capability may represent a positive predictive factor. Similarly, if the decay rate is slow or the peak (or time to saturation) is reached later in the response cycle, this may also represent a positive predictive factor for that a favorable treatment response is indicated. Other examples include later uptake and a smaller decrease from a peak value after a representative time. For example, if the signal exhibits less than a predetermined percentage drop from peak or maximum radiation activity after a representative time (such as 0.25 to 1–5 hours after initiation of the administration of the radiolabeled analyte to the subject), this may represent a favorable predictive factor.

For monitoring based on [$^{14}$C]glucose, or C-14 labeled glucose derivatives (such as dextraglucose), the biochemical processes associated with the metabolism or glycolysis of the glucose may be such that the radiolabeled component is discharged from the body in as little as 5–10 minutes from the time of administration, and the data collection may be carried out to obtain increased data points during a shorter collection time, such as, but not limited to, during the first 0.25 hours, such as during the time period extending between about time equal about 0 to about 15 minutes-1 hour post-initiation of the administration of the radiolabeled glucose/glucose derivative.

FIG. 6C represents monitoring of the biological half-life ($T_{1/2}$). Biological half-life times greater than a predetermined time may be an additional favorable or positive predictive factor. The presence of several of the positive predictive factors may indicate a particularly reliable indication of a favorable treatment opportunity.

FIG. 6B illustrates that the area under the curve can be used to calculate the dose of radiation received at the targeted site. Other dose correlation or calculation means can also be employed. FIG. 6E illustrates that the signal can be monitored and mathematically integrated and then a (first) derivative mathematically taken to represent the rate of change of concentration over time associated therewith. For illustration, in the embodiment shown, the lineshape of FIG. 6E corresponds to the derivative of the profile of FIG. 6A, albeit in a unitless manner without accounting for the amplitude values. The activity corresponds to the count (C) over time (taken in small pulsed intervals as noted above). Of course, other parameters and quantification or evaluation processing methods can be used depending on the particular application and information desired.

FIG. 6D illustrates that the system can obtain a plurality of different data sets, each corresponding to a desired monitoring period. As shown, three different temporally separate response periods are monitored. The third response period is shown as having an increase in detected radiation as may occur when an enhanced or favorable treatment is identified. These monitoring procedures can be performed prior to each therapeutic treatment, or several times before a favorable treatment window is indicated. The monitoring can also be done after steps are taken to influence or induce the targeted region to be more receptive to drug uptake (such as by directing external radiation at the target site).

It is noted that relative or absolute values of the detected signal can be used to assess the intensity or quantify the amount of radiation at the site (such as by taking a measurement before radiation is introduced to have a baseline indication to cancel out background information or by using the ratio of two measurements).

Figure 6F:
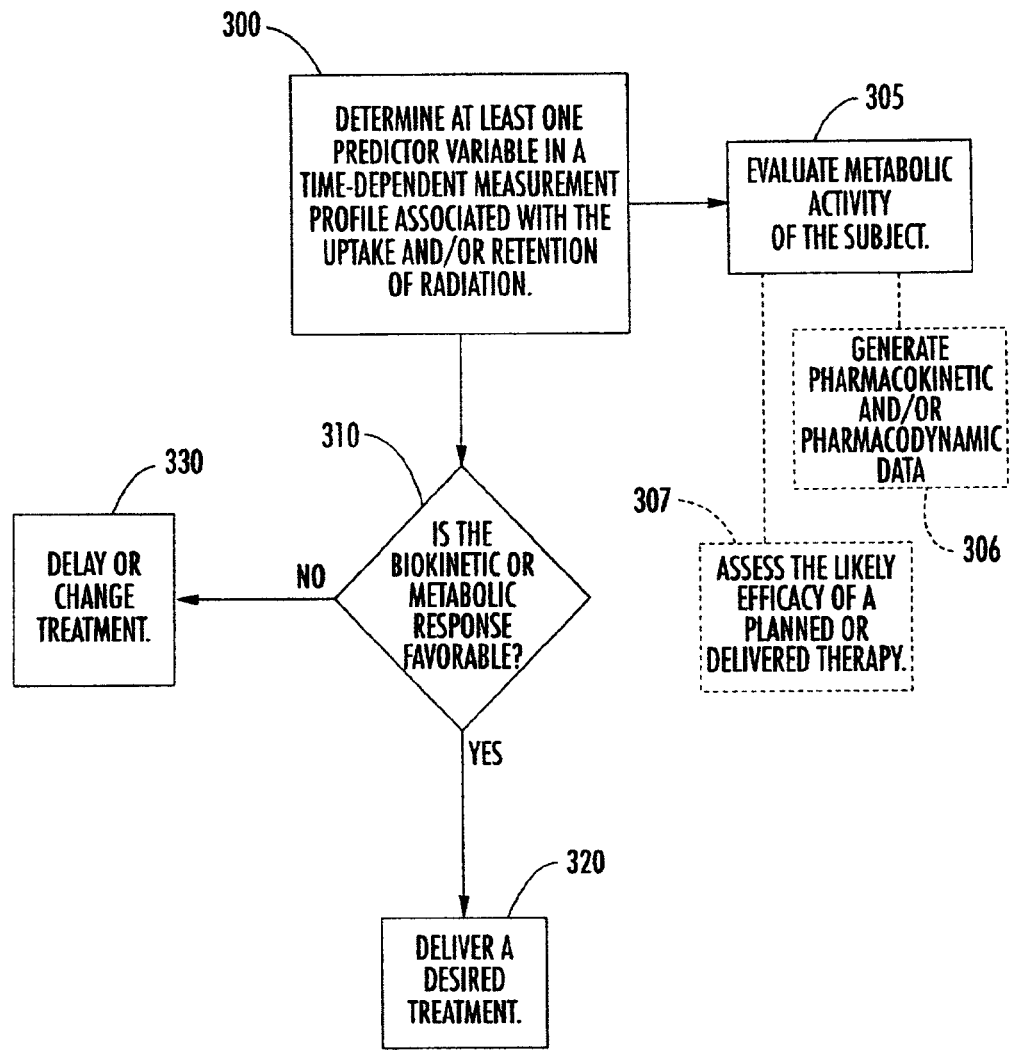
FIG. 6F is a flow diagram of a method for using calculated kinetic factors or one or more predictive variables to determine whether a biokinetic response is favorable in making therapeutic treatment decisions according to embodiments of the present invention.

FIG. 6F is a flow diagram of a method (preferably carried out by a computer program) for using at least one predictor variable taken from a time-dependent measurement profile associated with the uptake and/or retention of radiation in the tissue. The predictor variable can be a plurality of calculated kinetic factors to determine whether a biokinetic response (which can mean changes in the biological or physiological function of the subject) is favorable in order to make therapeutic treatment decisions according to embodiments of the present invention. As shown, at least one predictor variable (which can be a plurality of predictive kinetic factors) associated with the uptake and/or retention of radiation is determined (Block 300). The predictive variable can be one of those described above or other parameters. The method then assesses the metabolic activity of the subject (Block 305) and/or whether the biokinetic response of the subject is favorable (Block 310). If so, in certain embodiments then a desired treatment can be delivered to the subject (Block 320). If not, then a treatment can be delayed or postponed or altered (Block 330) to attempt to increase the chances for a favorable therapeutic response. The method may also consider the available therapy types and select one which is more likely to achieve a clinically satisfactory outcome based on tumor type, certain kinetic or activity based predictive factors, or other patient information (such as age, treatment number (such as whether it is a primary or secondary or tertiary treatment)) or the like. Alternatively, or additionally, the metabolic evaluation (Block 305) can be used to study or evaluate pharmacokinetic data (Block 306) and/or to assess the efficacy of a planned or delivered therapy (Block 307).

Figure 9B:
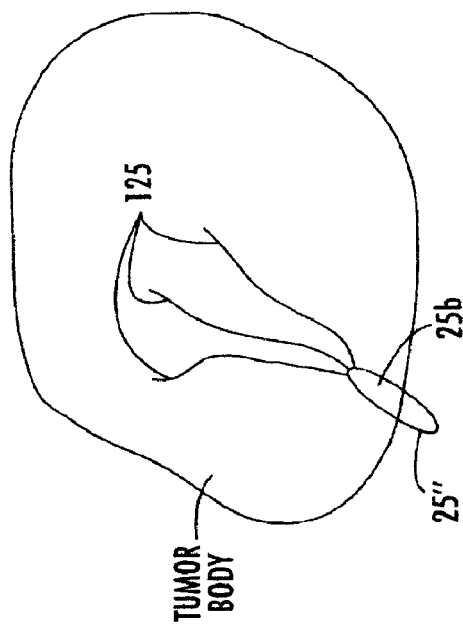
FIG. 9B is a schematic illustration of a sensor with a plurality of fiber optic leads used to relay light according to embodiments of the present invention.

The detection systems contemplated by embodiments of the present invention may be configured in several suitable configurations. For example, the system 10 can be configured: (a) as a fiber-based system with externally located operating electronics such as shown in FIGS. 5B and 10A; (b) as a multiple-implantable component system such as shown in FIG. 9 (indirect detection that use optical fibers with scintillators that can feed light back to a collective photodiode) and FIG. 10B (direct beta radiation such as with a detector crystal); (c) a single implantable unit telemetry linked to an external reader such as shown in FIG. 10C (semiconductor used as a direct detector that similar to FIG. 10B can directly convert the beta into electron-hole pairs that are electrically measured); and (d) a single implantable unit with an indirect detector such as shown in FIG. 7 (the body of the implantable unit is the scintillator and is in optical communication with a photodiode). A combination of the systems or selected components described herein may also be employed. In certain embodiments, a plurality of sensing probes (direct and/or indirect) can be used with a central or single external reader to monitor radiation at more than one location in the body.

Generally stated, there are two primary means for measuring ionizing radiation using a solid-state detector: namely, direct and indirect conversion. As noted above, the radiation sensor 25 of embodiments of the present invention may be configured for direct or indirect detection. In direct conversion, the ionizing radiation itself creates an electron-hole pair in a region of the detector, and these changes can be separated by a biasing electric field and collected as a current through or in the device. Indirect conversion converts ionizing radiation to light in a scintillator and the light is detected by the mechanism involved in the pair production described above.

As such, the detection system 10 and/or the associated sensor(s) 25 may be physically and/or operationally configured in a number of suitable designs. For example, referring now to FIG. 10A, the sensor 25 of the detection system 10 may be configured for acute placement of a percutaneous or internally located scintillating fiber(s) that couples to an externally located detector 10D. That is, the sensor 25 directly relays the light signal to a detector 10D located outside the body. In the embodiment shown in FIG. 10A, the external detector 10D comprises those components inside the broken line. Other configurations of detectors 10D may be employed. This embodiment may reduce the size and electronic operational complexity of the portion of the device inserted or placed into the patient.

Figure 10A:
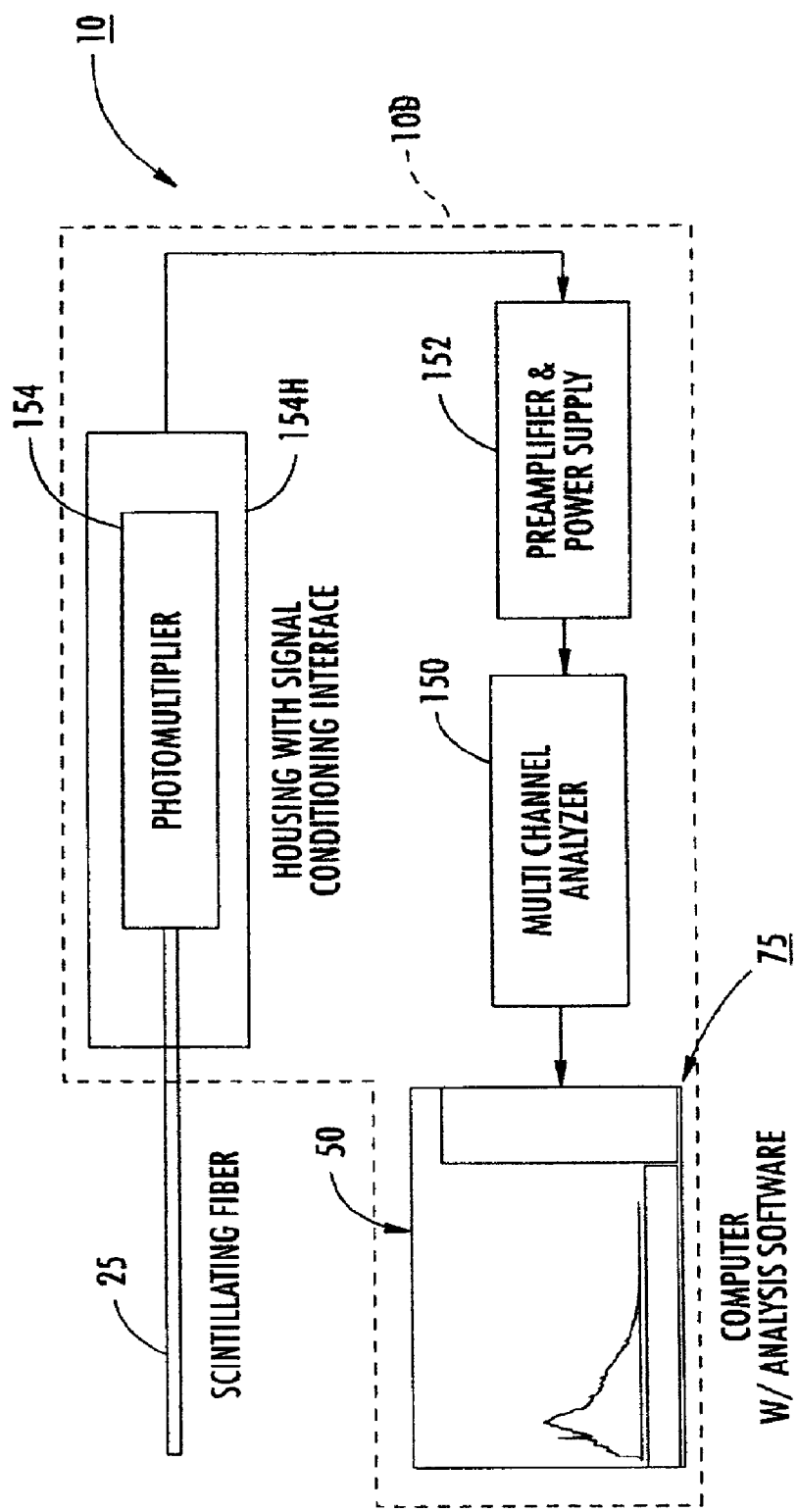
FIG. 10A is a schematic of a fiber optic system used to evaluate beta spectroscopy signals according to embodiments of the present invention.
Figure 10B:
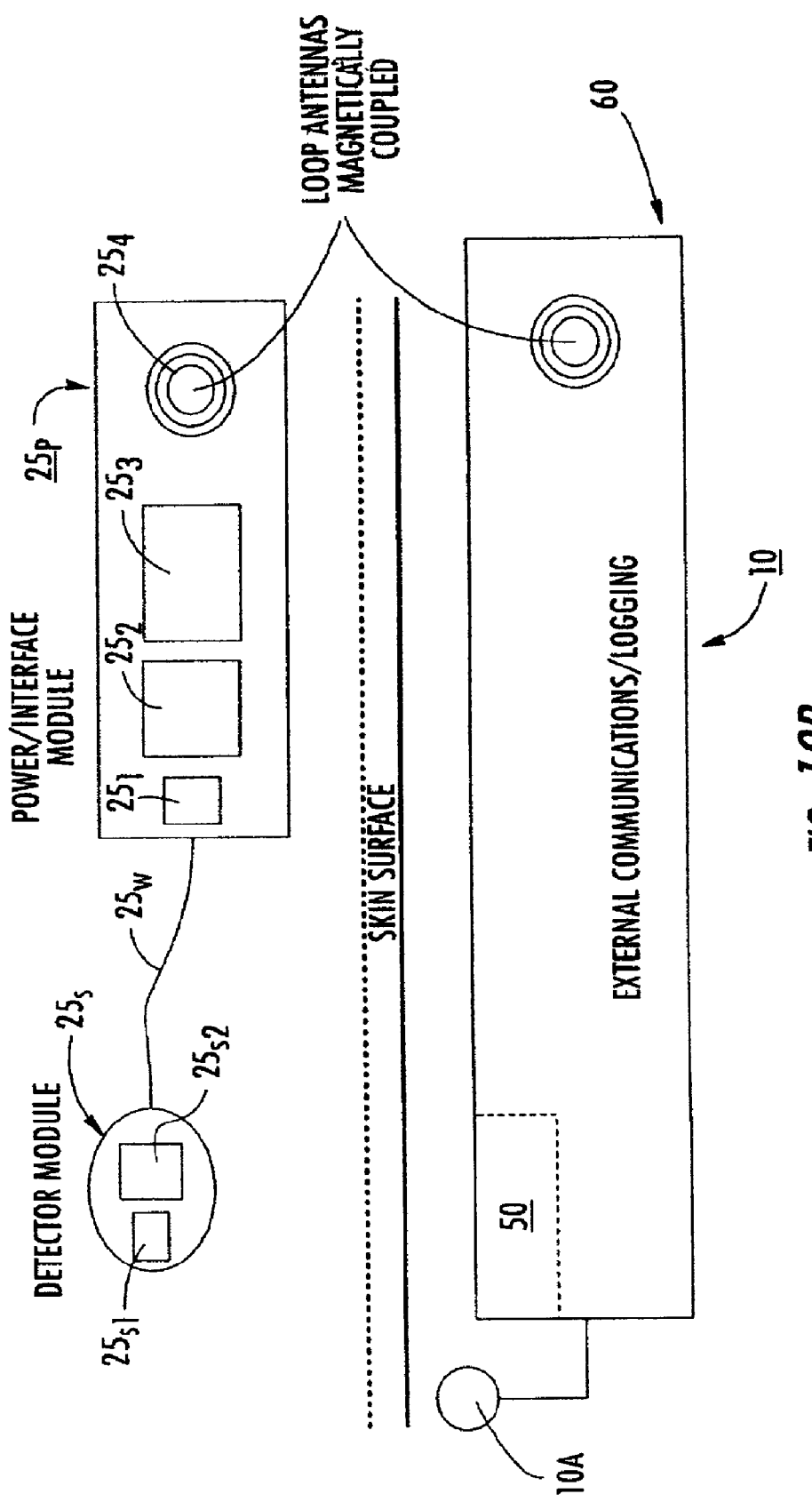
FIG. 10B is a schematic of an implantable wireless system used to obtain data associated with internally administered beta radiation.

As shown in FIG. 10B, in other embodiments, a fully implantable sensor assembly 25 may be configured with at least one sensor head (probe body) 25s that is independently positionable in the body of the subject so that it contacts the targeted tissue. The sensor or probe body 25s is connected to a processor body 25p via one or more fibers or wires 25w and can be (subcutaneously) implantable a distance away from the probe body 25s typically closer to the surface of the skin. Although illustrated as subcutaneously implanted, the processor body 25p may also be externally mounted onto the skin of the subject and secured in position with an external biocompatible covering. The processor body 25p can be configured to include most of the wireless transmit/receive circuitry and so that it communicates with an external reader 60. The internal processor body 25p can include a differential receiver $25_1$, an amplifier/pulse shaper $25_2$, a modulator $25_3$, and a loop antenna $25_4$ that can be magnetically coupled to a like component in the external reader 60. The processor body 25p can also include other components configured to power the sensor 25s and/or communicate or interface with the external reader 60. The probe body or sensor 25s can comprise the active sensing component such as a detector crystal $25_{s1}$ and a charge amplifier/bias network line, driver $25_{s2}$. The external reader 60 includes a telemetry antenna and the processor 50.

In still other embodiments, as shown in FIG. 10C, the sensor 25 is a unitary body that includes the active sensor, shown as a direct beta radiation detector 25s, as well as the operational and communication electronics 25e that is configured to wirelessly communicate with the external reader and collect the radiation data. The unitary body may be housed in a biocompatible sealed-glass or suitable material housing 25c that is configured for direct detection of the radiation and miniaturized and implantable into the target tissue. The support electronics 25e can be positioned on a circuit substrate 25sub. The implantable unit 25 may also include a ferrite core to promote external communication operations. The radiation sensor 25 can be implanted in the body of a subject via surgery, injection, or inserted through a medical trochar. The radiation sensor 25 can be miniaturized such as sized at about 2–3 mm in width (or less) and about 10–20, and typically less than 25 mm in length. Each of the implantable versions shown in FIGS. 10B and 10C may be particularly suitable for chronic in vivo placement.

The operating power for certain of the implantable sensor 25 configurations may be provided by an inductive coupling of a RF field positioned in the vicinity of the implantable sensor 25. This is typically provided by a reader 60 (FIG. 5A) which can generate the desired power field and receive the signals from the sensor 25 (devices which include both transmit and receive functions may be termed a "transponder"). Alternatively (or additionally), the implantable sensor 25 may employ an internally mounted battery as a power source (not shown). See U.S. patent application Ser. No. 09/407,359 incorporated by reference above. In certain embodiments, the reader 60 (FIG. 5A) can be configured to transmit information as well as power to the sensor 25 (for inductively powered models) and to receive the detected radiation signals (i.e., a "two-way" system).

FIG. 7 illustrates an indirect conversion sensor 25. Turning now to FIG. 7, an example of an alternate implantable radiation sensor 25 is illustrated. The radiation sensor 25 can be implanted in the body of a subject via surgery or inserted through a medical trochar. As before, the radiation sensor 25 can be miniaturized, such as sized at about 2–3 mm in width (or less) and about 10–20 mm, and typically less than 25 mm in length. The radiation sensor 25 shown in FIG. 7 is configured to measure or detect ionizing radiation by generating analog or digital signals that represent the detected or measured radiation.

In certain embodiments, the sensor 25 can include a photodiode or similar semiconductor element as the active sensor. Examples of suitable active sensors can include, but are not limited to, a silicon photodiode operating in photovoltaic mode, a silicon photodiode operating in reverse bias mode, silicon photodiode operating in avalanche mode, an avalanche photodiode (APD), an APD in Geiger mode, a silicon PIN diode, a charge coupled device (CCD), other photodiodes or radiation sensors composed of gallium arsenide, II-a natural and CVD diamond, GaN, SiC, CdZincT ("CZT"), and ionization chambers and miniature electron multiplier and photomultiplier devices.

In the embodiment shown in FIG. 7, the body of the sensor 25 may be molded into a desired geometry from a scintillating material 28. In the embodiment shown, a miniaturized elongated cylindrical body 25b is used to hold the internal circuitry. The inner and outer surfaces 25*i* and 25*o* of the body 25*b* include a reflective material 25*r*. As shown, in certain embodiments, the entire perimeter of the body of the sensor 25 is able to act as a scintillator. The reflective material 25*r* may be positioned to encase the outer and inner walls of the scintillator material. The reflective material 25*r* may be formed onto the scintillator material by various techniques such as vacuum deposition, coating, spraying, or the like. The reflective surfaces 25*r* define the boundaries of the light guide or light channel 33 which, in operation, captures and directs the light created by the conversion of the ionizing radiation to at least one "impinging" or detection point 26 which does not have the reflective coating, which allows the light to travel out of the light channel 33 and into to at least one proximately positioned photo detector 30.

As shown, the sensor 25 has two opposing light input points 26, each of which is in optical communication with a respective photo detector, such as one of the photodetectors 30. The photodetector 30 resides on a circuit substrate 32 on opposing sides of a line of symmetry extending axially along the body of the device. An index matching material can be positioned between the light entrance surface of the photodiode 30 and the exit portion of the light guide 26. The index matching material may be formed onto the exit portion of the light guide 26 or maybe formed as a film or pad held therebetween. The index matching material may be selected so that its refractive index is close to the average of the indices of the scintillating material and the material forming the entrance or front surface of the photodiode 30*f* (and typically such that it is substantially different from air). As noted above, for certain embodiments, the radiation sensor 25 is configured to detect peak radiation on the level of about 55 KeV. The radiation sensor may be operated to provide about 20–1000 or more counts per second. For example, for 166 nCi/cc, and about a 2 cm detector (active surface) region, the radiation sensor 25 may provide about 30 counts per second.

A ferrite core inductor 40 is positioned in the cavity of the sensor body 25*b* away from the photodiode(s) 30. Additional support or components 35 may be mounted to the circuit substrate to provide operational or mechanical support therefor.

It is noted that other suitable geometries can also be used to form the light guide or channel(s) 33. FIG. 8A illustrates a single photodiode 30 located at a light exit portion 26 at one end of the light guide channel 33. FIG. 8B illustrates a light exit portion 26 at an end portion of the body of the sensor 25*b*.

Figure 9A:
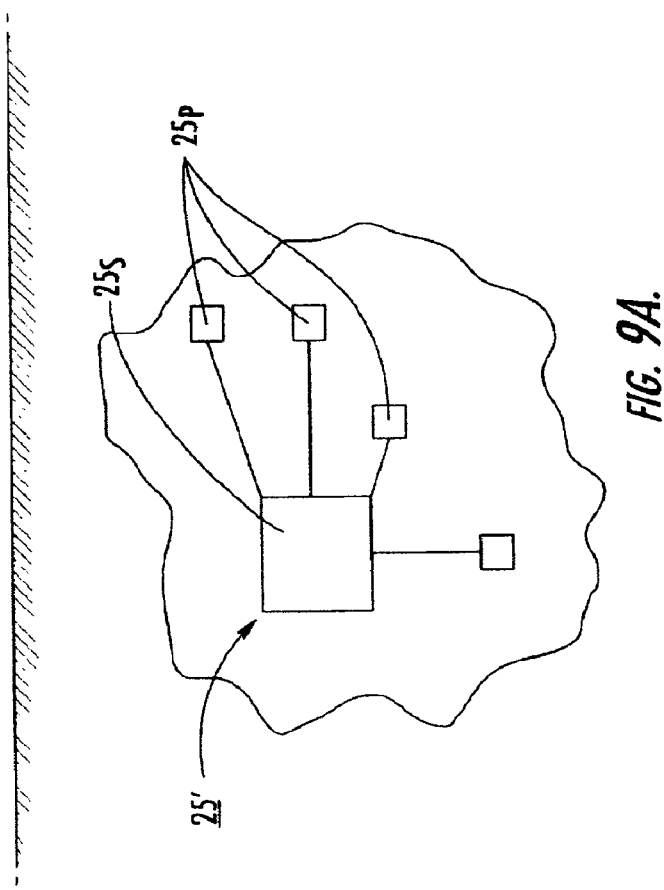
FIG. 9A is a schematic illustration of a sensor with a plurality of radiation sensing probes according to embodiments of the present invention.
Figure 10C:
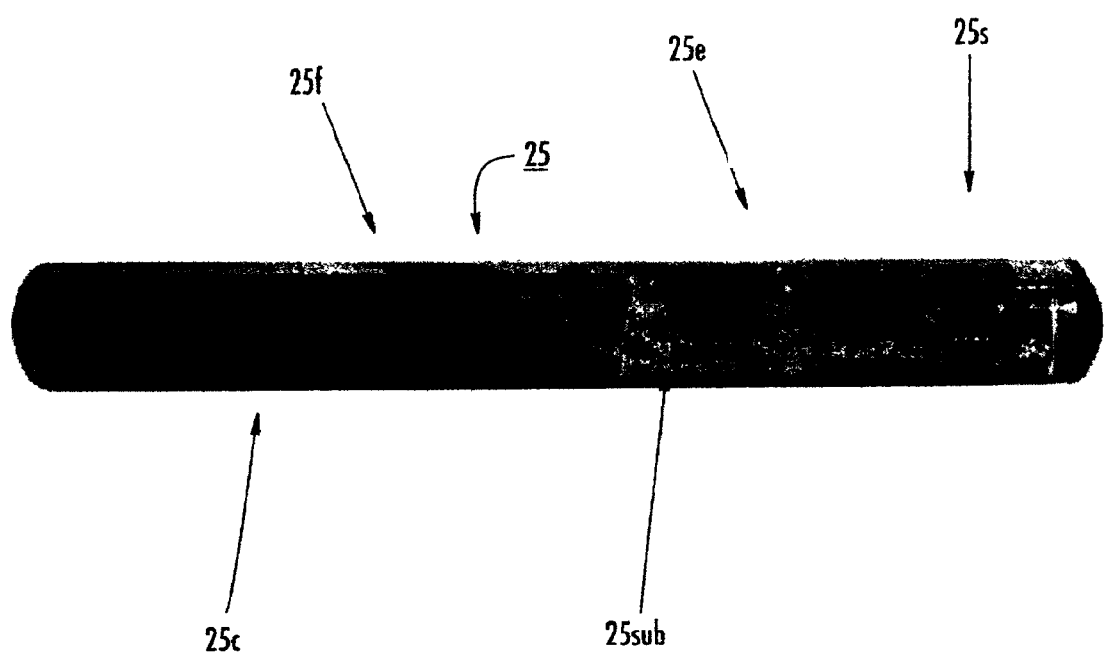
FIG. 10C is a greatly enlarged front view of an implantable wireless sensor configured to detect internally administered beta radiation according to embodiments of the present invention.

FIG. 9A illustrates that a sensor 25' with multiple radiation probes 25*p*, each on a flexible arm 25*arm* can be used to detect at different regions in the desired region of the body. The radiation sensor 25' may be implantable with the center body 25*s* housing the ferrite core inductor (acting as a power/transmitting satellite body) and the end probes 25*p* providing the lightguides and scintillators and being connected to the primary body. The arms of the probes 25*arm* can be covered in reflective material to channel the light to selected photodiodes in the center body 25*s* (the probes being configured so that they are each in optical communication with a selected photodiode therein). As noted before, the radiation sensor 25, 25' may also be positioned on a catheter or probe. In this embodiment, the sensor(s) 25, 25' may reside on a perimeter portion thereof such that, in position in the body, each (the active part of the probe or sensor) is exposed to the desired target region in the subject so as to allow the radiation to activate the scintillator material.

FIG. 9B illustrates that a sensor 25" may also include a sensor body 25*b* with a plurality of fiber optic segments or leads 125 positioned in the tumor mass. The fiber optic leads 125 may be coated with a scintillator material as noted above and used to collect, capture, and relay light scintillated from different regions of the target site to the sensor body 25*b*. Each lead 125 may be polled separately of the light funneled concurrently to one or more active sensing regions in the sensor body 25*b* which may be configured with or in optical communication with a PMT, photo-avalanche detector or the like.

The present invention is explained in greater detail in the following non-limiting Examples.

EXAMPLES

A fiber optic probe suitable for transcutaneous placement was used with a photomultiplier tube for detection of beta radiation from C-14 labeled glucose (available from Amersham Pharmacia Biotech). A commercially available channel multiplier tube (from Perkin Elmer, model C943 P) was used with a small array of scintillating fibers (from Bicron). The fibers were packed loosely into a retaining collet and fixed in place with epoxy (EPO-TEK 301). The sample surface was then polished to remove any residual epoxy from the faces of the fibers. The active area of the fiber bundle was about 0.17 $cm^2$, and typically the active surface is at least about 0.10–1 $cm^2$. The opposite end of the fiber bundle was mated to the surface of the channel multiplier with optical cement. The system was assembled with a power supply, the channel multiplier and the fiber bundle detector.

The C-14 labeled glucose was used at a concentration of about 50–200 $\mu$Ci/ml and the tips of the fibers were exposed to the solution in a light-tight enclosure. Current pulses from the channel multiplier due to beta events were amplified (using amplifier model A101 from Amptek) and sent as TTL pulses. A LabView device (from National Instruments) was used to record or monitor the counts per time. No pulse-height analysis was performed on the counts from the channel multiplier. About 850 counts per second were recorded whereas the background count was below about 25 counts per second.

The energy spectrum from C-14 decay peaks at 55 KeV. The average range of the C-14 beta in water is believed to be about 50 $\mu$m. Using the effective surface area of the fiber bundle, the count rate observed was consistent with an effective detection thickness of 50 $\mu$m. That is, the attenuation of betas reaching the fibers due to the water is equivalent to having the listed activity present in a uniform layer on the face of the fiber that is 50 $\mu$m thick.

The detector sensitivity can be impacted by the amount of surface area. In operation, each count corresponds to a pulse of charge and this charge can be quantified using a charge sensitive detector. The signal to noise ratio may be enhanced by allowing for signal integration over short time windows, in the range of 1–100 $\mu$s, and more typically closer to the lower end of the range so that dark counts are reduced. The time duration of the signal pulses can be less than about 100 ns.

For in vivo evaluations, a 2 mm fiber bundle may be inserted into position via a small incision at an entry site. A 13 gauge needle, with a solid removable component, can be inserted into the incision. The solid component can be removed and replaced with the fiber or fiber bundle. Once in place, a retention component can be applied to secure it in position (suture, surgical glue or the like) and the needle removed. The labeled glucose can be injected into the tail vein of test animals (such as rats) in a single bolus. The total activity may range from about 1–10 mCi based on the SNR noted above. After several passes in the blood stream, tissue levels of C-14 will rise (approximately 2–3 minutes after administration). The radiation detected by the fiber bundle and relayed to the photomultiplier tube can be monitored until the concentration drops to about 10% of the initial value in counts per second to evaluate individual differences in bio or pharmacokinetics between subjects and tumors.

Experiments using single or dual probe sensors have been used to obtain in vivo response data. The radiolabeled analytes used in the in vivo experiments included $^{14}$C-2DG (C-14 labeled 2-deoxyglucose) and $^{14}$C-5FU (C-14 labeled 5-Fluorouracil, a chemotherapeutic cytotoxic agent).

Figure 11A:
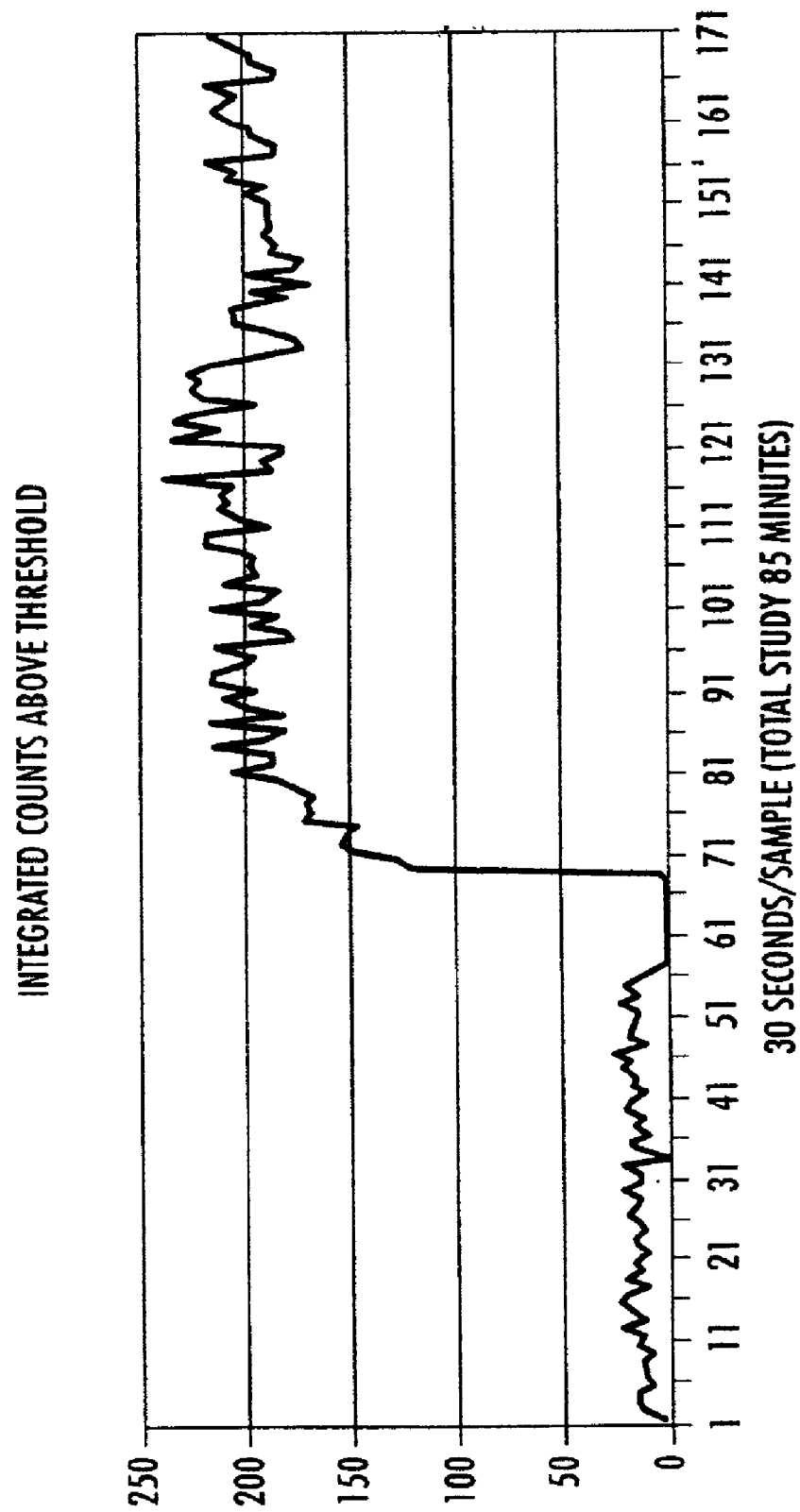
FIG. 11A is a graph of an exemplary in vivo response profile of the concentration or uptake over time of a radiolabeled analyte according to embodiments of the present invention.

FIG. 11A illustrates a response profile graph (an integrated counts (above threshold) over time profile) taken over a monitored time period of about 85 minutes (study #2). The counts were taken on a thirty seconds/sample count time frame. In this experiment, a fiber optic probe was positioned subcutaneously in "normal" or non-cancerous tissue in the back of a Fisher 344 rat. A dose of 50 $\mu$Ci of $^{14}$C-2DG was injected in the tail vein. The data was monitored for about 85 minutes. As shown, the counts increased after the injection as reached a plateau at about 10 minutes from the time of injection (about 35 minutes into the monitoring period). The initial portion of the graph has values that represent "baseline" or dark current. At about point "70" (corresponding to about 35 minutes), the injection is given and uptake continues until it plateaus around point "90" (corresponding to about 45 minutes).

Figure 11B:
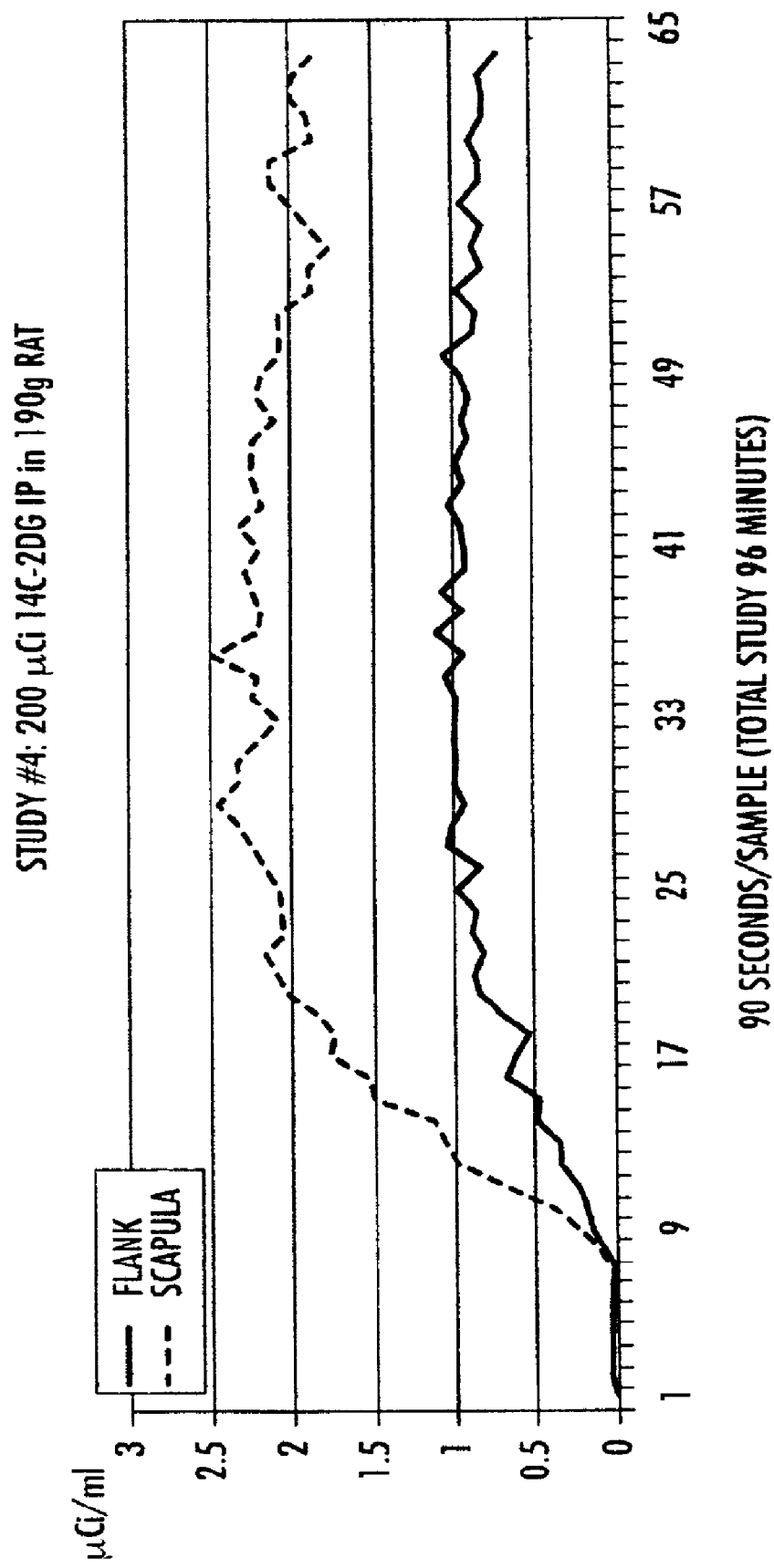
FIG. 11B is a graph of another exemplary in vivo response profile of the concentration or uptake over time of a radiolabeled analyte according to embodiments of the present invention.
Figure 11C:
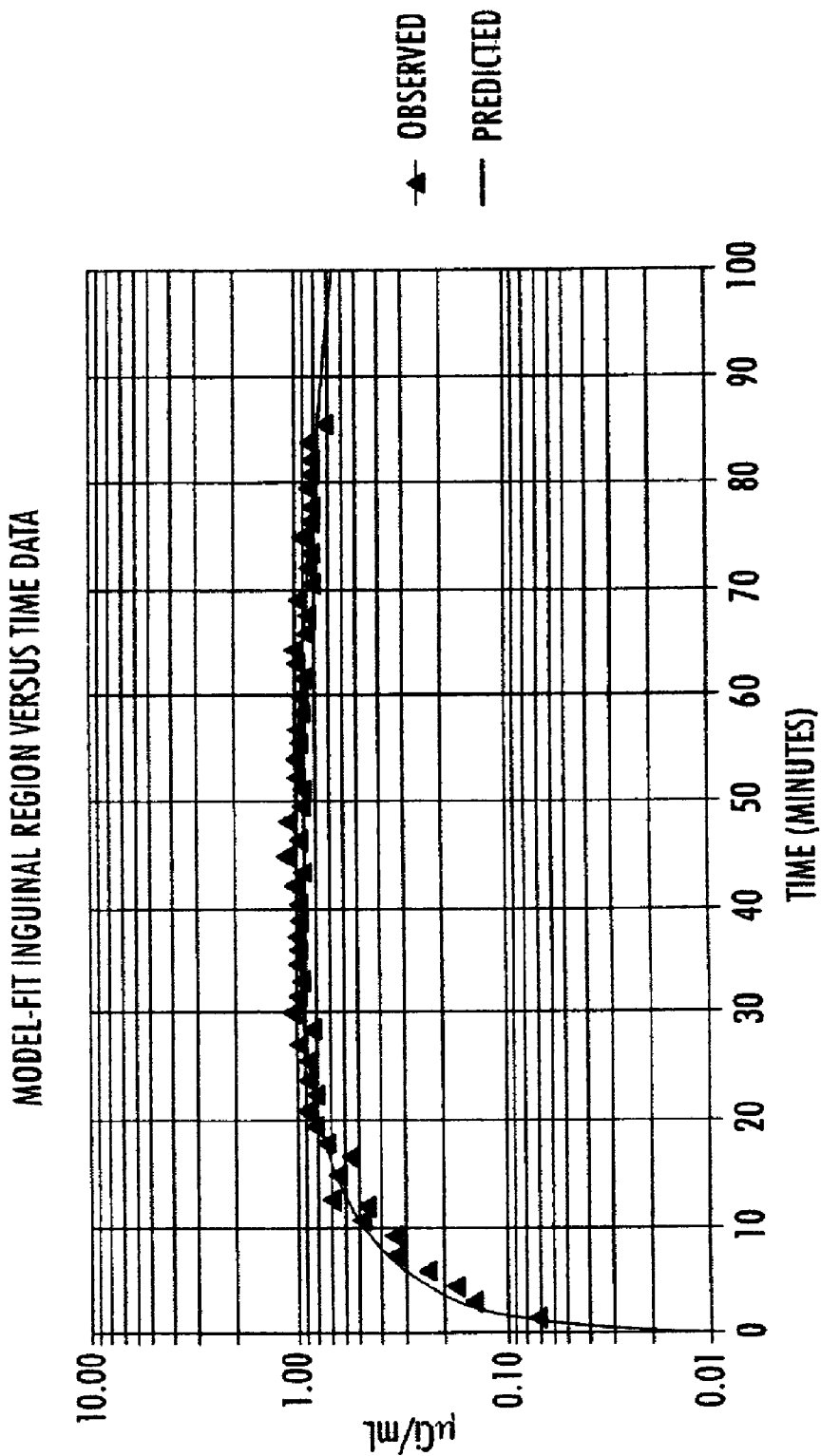
FIG. 11C is a graph of a statistical model of predicted values compared to observed results of the flank/inguinal probe region of FIG. 11B according to embodiments of the present invention.

FIGS. 11B–11C illustrate graphs of data obtained using two probes, each placed subcutaneously in normal tissue of a 190 gram female Fisher 344 rat, one placed in the flank/inguinal and the other in the scapula (study #4). The graph plots $\mu$Ci/ml over time at 90 second per mark with the upper line corresponding to the data obtained at the scapula and the lower line corresponding to the data obtained at the flank. In this experiment, a bolus of 200 $\mu$Ci of $^{14}$C 2-DG was administered via intra-peritoneal (IP) injection. The data was monitored for about 96 minutes. As shown, higher concentrations were obtained in the scapula region compared to the flank region. The data supports that pharmacokinetic modeling of in vivo concentration data is feasible.

FIG. 11C is a graph of a pharmacokinetic model-fit of the flank normal tissue data (from the inguinal region) of FIG. 11B versus time ($\mu$Ci/ml versus time in minutes). The triangulated points represent observed data and the line represents the predicted values. As shown, there is a significant ramp up in the value of the detected signal or counts during the first 10 minutes, tapering to a gradual slope uptake in the 10–30 minute range, followed by a substantial level region in the curve at about 35 minutes that extends to just over the 60 minute range, whereupon the line is predicted to taper down. The peak or maxima point in the graph is reached in the 20–50 minute range according to the observed points on the graph. FIG. 11C used a one compartmental PK model to generate the predicted data with 1st order input and 1st order elimination kinetics. This statistical model was used to model the observed values obtained from the flank/inguinal probe versus that which can be predicted using a model of the previously stated characteristics. Other statistical functions may also be used to develop a predictive model. Departures from the model may be used to evaluate tumor status such as growth, remission, or kill and/or irregular metabolic or response behavior.

Figure 11D:
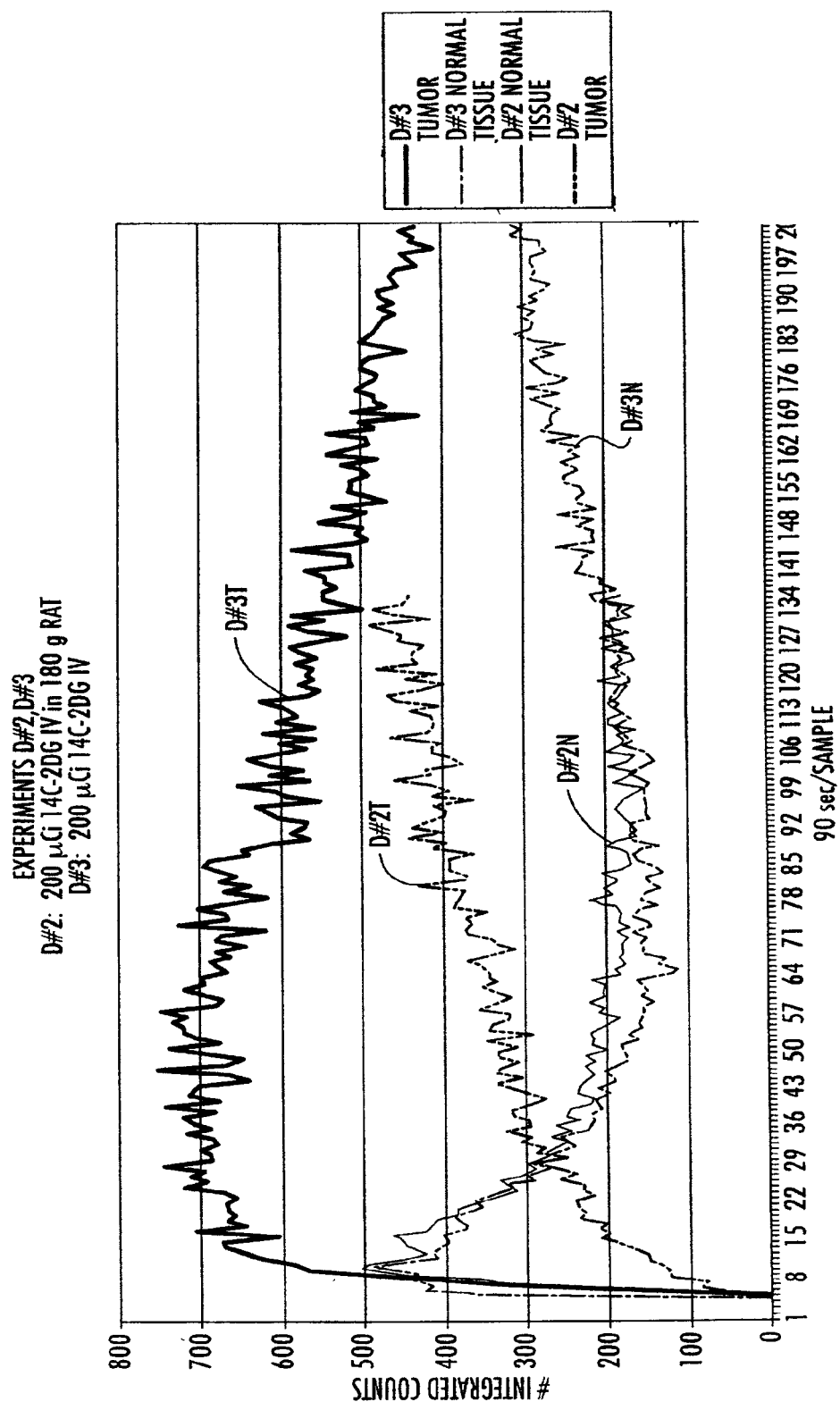
FIG. 11D is a graph of additional exemplary in vivo response profiles of the counts over time of a radiolabeled analyte according to embodiments of the present invention.

FIG. 11D is a graph of two other studies, identified by D#2 and D#3. Each of these studies used 200 $\mu$Ci of $^{14}$C-2DG administered via an IV to a 180 g rat to monitor the number of integrated counts obtained per 90 seconds in a sampling period (90 seconds per each indicated mark on the time axis). As shown, two probes were used to gather response data both in normal (D#2N, D#3N) and tumor (D#2T, D#3T) tissue.

Figure 12A:
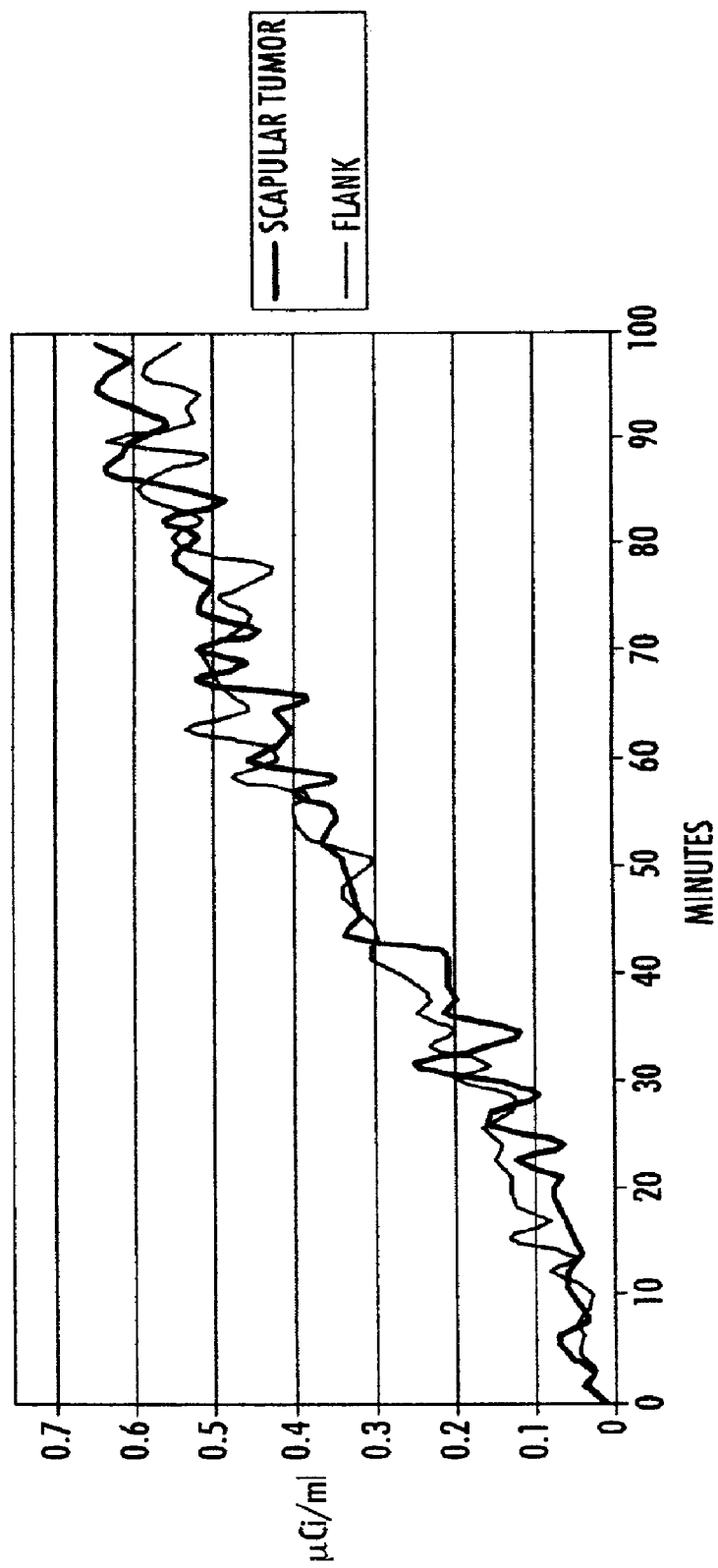
FIG. 12A is a graph of another exemplary in vivo response profile of the concentration or uptake over time of a radiolabeled analyte according to embodiments of the present invention.

FIG. 12A is a graph of a response profile of data in two locations in a tumor bearing 270 g Fisher 344 rat, obtained via a dual probe test set-up (study #5). Again, one of the two probes was positioned subcutaneously in the scapular tissue (in a tumor) and the other in the flank (normal tissue) of the rat. A dose of 250 $\mu$Ci of $^{14}$C labeled 5FU was administered via intraperitoneal injection. Data was monitored for about 100 minutes. FIG. 12A is a graph of the concentration of the radiolabeled analyte ($\mu$Ci) over time (minutes) and illustrates that $^{14}$C-5FU is relatively slowly absorbed into the flank tissue and scapular tumor after the injection. The concentration and uptake profiles of the $^{14}$C-5FU are similar for both locations. The uptake profile is consistent with results presented by Mahteme et al., Anti-Cancer Res, 18:943–50, 1998 (describing an autoradiographic study in the rat). As shown in FIG. 12A, the $^{14}$C concentrations continue to rise after about 90–100 minutes from the time of injection.

Figure 12B:
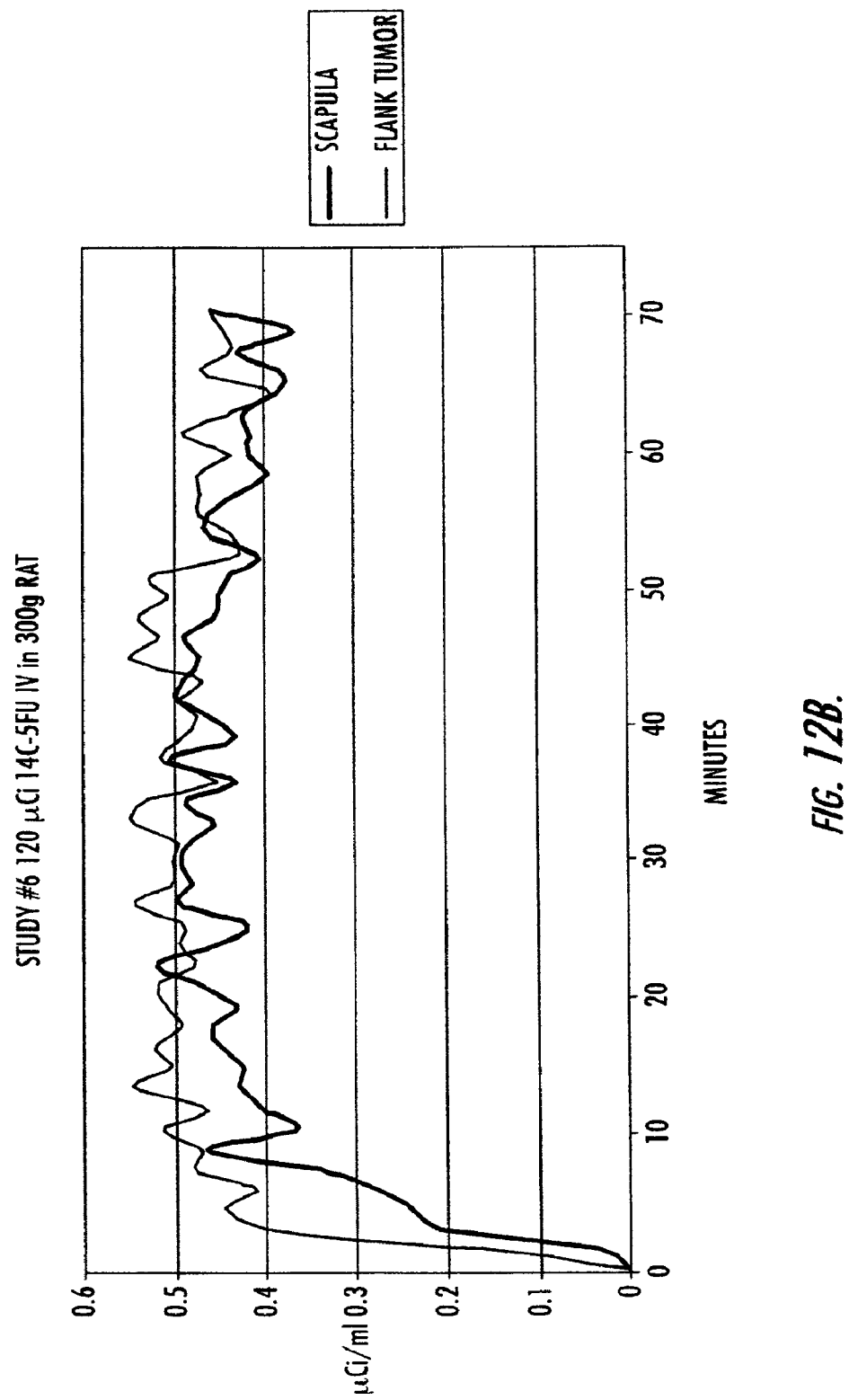
FIG. 12B is a graph of an additional exemplary in vivo response profile of the concentration or uptake over time of a radiolabeled analyte according to embodiments of the present invention.

FIG. 12B is a graph of a response profile of concentration (CCi) over time (minutes) of a 120 $\mu$Ci dose of $^{14}$C-5FU administered via an IV in the tail vein in a 300 gram Fisher 344 rat (study #6). Again, two probes were subcutaneously placed in the rat, one in the flank (in tumor tissue) and the other in normal tissue at the scapula. This subject was monitored about 70 minutes after injection. This graph illustrates that the $^{14}$C-5FU uptake is measurable or detectable shortly after the injection and that the concentrations peak after within about 10–30 minutes after dosing. The upper line represents the flank (tumor tissue) and the lower line represents the normal scapula tissue. Comparing the two lines in the graph, it is shown that in this experiment, the $^{14}$C concentration level peaks earlier in the tumor tissue than in the normal tissue.

It is anticipated that a glucose based radiolabeled analyte can be administered multiple times during a treatment period to evaluate metabolic activity and/or tumor response. In addition, a radiolabeled glucose (or other metabolite) can be administered along with a therapeutic agent (which may also be radiolabeled), typically each at different times.

In summary, in certain embodiments, the present invention may be used to assess metabolic response or activity and/or may help identify more favorable treatment periods or a subject's likely affinity or sensitivity to a drug before a therapeutic dose is administered. The data can be obtained in substantially real time via intermittent, episodic, or substantially continuous monitoring during desired monitoring periods to provide information on the biological, physiological, and/or metabolic behavior of one or more target regions of interest. Such data may be employed to assess (a) single or combination therapies (such as which therapy should precede the other or whether both should be delivered concurrently or proximate to the other, and the like); (b) pharmacokinetics/pharmacodynamics; (c) alterations in or status of metabolic activity or function; (d) tumor response or status; and (e) drug behavior in drug discovery programs or pre-clinical or clinical trials.

Unlike conventional treatments, where empirical protocols on the timing and the toxicity of the planned treatment can guide deliveries of cytotoxic agents which may be more damaging to normal tissue than to any positive treatment impact on the malignant cell population, certain embodiments of the present invention can allow for customized treatments based on the dynamic changes during treatment that occurs within a malignant cell population. Making this information available to attending physicians and clinicians can allow them to exploit the revealed differences between malignant and normal cells, and hence improve the treatment procedures to achieve better outcomes.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, where used, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for determining whether to administer a therapeutic amount of a chemotherapeutic drug for tumor treatment by determining an in vivo localized uptake response in solid tissue in a patient, comprising the steps of:
   positioning at least one sensor in vivo in solid tissue in a region of interest in the body of the patient;
   administering a test dose of a C-14 radiolabeled chemotherapeutic drug to the patient;
   detecting a signal from the at least one sensor corresponding to the radiation in the region of interest in the patient based on the administering step;
   monitoring the signal over time to determine a localized uptake response in the solid tissue of the patient based on the administered test dose; and
   determining whether to administer a therapeutic amount of a non-radiolabled version of the chemotherapeutic drug based on the determined localized uptake response to the test dose.

2. A method according to claim 1, further comprising:
   wirelessly relaying the data to an external reader; and
   processing the relayed signal to electronically generate a time dependent measurement profile of radioactivity in localized solid tissue to identify at least one predictor variable of interest to assess the drug uptake response in the solid tissue.

3. A method according to claim 1, wherein said determining step determines whether uptake and retention of the radiolabeled test dose in the localized solid tissue is above a predetermined threshold level.

4. A method according to claim 3, wherein said determining step determines the rate of the increase and decay in the signal strength over time.

5. A method according to claim 1, wherein said determining step determines at least one of the following; the amount of time the detected signal remains above a threshold level, the time the signal takes to reach a peak level, the time the signal takes to decay to below a threshold value, and the rate of decay from the peak to the threshold value.

6. A method according to claim 1, wherein said monitoring step monitors, over a period of at least about 15 minutes from the time said administering step is initiated, and wherein said determining step determines at least one kinetic and/or static predictor variable associated with the uptake response of the radiation in the localized solid tissue, the predictor variable including at least one of the following:
   (a) a time at which a detected peak radiation occurs;
   (b) biological ½ life of the detected radiation;
   (c) rate of increase of detected radiation;
   (d) rate of decrease of detected radiation;
   (e) a time at which the detected radiation falls a predetermined amount below the peak detected value;
   (f) a duration of time that the detected radiation signal increases in strength; and
   (g) a time during the monitored period when the detected radiation signal begins to decay.

7. A method according to claim 1, wherein the test dose is administered to the subject locally proximate to the region of interest.

8. A method according to claim 1, wherein the test dose is administered to the subject directly to the region of interest.

9. A method according to claim 1, wherein the test dose is administered to the subject systemically.

10. A method according to claim 1, wherein said determining step comprises generating a patient specific predictive treatment outcome of a planned drug therapy based on the monitored behavior of the test dose.

11. A method according to claim 1, wherein the sensor is implanted in solid tissue at a tumor treatment site, and wherein said determining step comprises evaluating radiation emitted from the C-14 radiolabeled test dose in the localized solid tissue to predict the likelihood of the respective patient having a favorable response to a known chemotherapeutic to thereby provide a patient-specific oncologic treatment evaluation.

12. A method according to claim 11, wherein the tumor treatment site comprises cancerous and/or precancerous cells, and wherein said monitoring step comprises determining cancer cell sensitivity and/or receptiveness to the radiolabeled test dose.

13. A method according to claim 1, wherein the administered radiolabeled test dose comprises C-14 labeled glucose.

14. A method according to claim 1, wherein the administered radiolabeled test dose comprises a C-14 labeled glucose derivative, wherein the glucose derivative is selected so that it has a modified glucose molecule chemical structure that is biocompatible and can be bio-chemically processed by the body.

15. A method according to claim 1, wherein the administered radiolabeled test dose comprises C-14 labeled 2-deoxyglucose.

16. A method according to claim 1, wherein the administered radiolabeled test dose comprises C-14 labeled dextraglucose.

17. A method according to claim 1, wherein the administered C-14 radiolabeled test dose comprises C-14 labeled 5-FU.

18. A method according to claim 1, further comprising evaluating metabolic activity in the subject based on data collected during said monitoring step.

19. A method according to claim 1, wherein said sensor is positioned in solid tissue spatially proximate a tumor site, and wherein said administering step is first carried out at a time which is proximate to a first planned therapeutic cancer treatment, said method further comprising:

administering a second test dose of the C-14 radiolabeled chermotherapeutic drug after the first test dose and after after administering a therapeutic treatment to monitor changes in cell kinetics following a therapeutic treatment.

20. A method according to claim 19, further comprising the step of selecting a subsequent therapeutic treatment type based on said determining step.

21. A method according to claim 1, further comprising identifying at least one type of known cancer treatment as being unlikely to be clinically effective for the respective patient in generally real-time based on said monitoring and determining steps.

22. A method according to claim 1, wherein the step of positioning is carried out so that at least one sensor is positioned in the body such that at least one sensor resides in solid tissue proximate to and/or in a cancerous tumor site.

23. A method according to claim 22, wherein the step of positioning is carried out so that the sensor is chronically implanted in the subject.

24. A method according to claim 23, wherein the sensor is a unitary body implantable sensor configured to detect radiation in at least one of a director indirect mode of detection and wirelessly communicate the detected radiation data to an externally located reader.

25. A method according to claim 23, wherein the sensor includes a sensor probe body connected to and spaced apart from a processor body, and wherein the step of positioning comprises implanting the sensor probe body at a first location proximate to or in the tumor site so that it can detect radiation in a direct and/or indirect radiation detection mode and implanting the processor body at a second subcutaneous location proximate normal tissue, the second location being spaced apart from the first location.

26. A method according to claim 1, wherein the at least one sensor is a plurality of sensors, each positioned in different locations in the body of the subject.

27. A method according to claim 1, wherein the test dose of the C-14 radiolabeled chemotherapeutic drug comprises an antibody for treating cancer.

28. A method according to claim 1, wherein said at least one sensor is a plurality of sensors configured to detect the emitted radiation from the test dose at a plurality of different solid tissue locations in vivo within the region of interest to determine the biokinetics of the tissue at different positions thereof.

29. A method according to claim 1, wherein the step of positioning is carried out so that at least one sensor is positioned proximate to cancerous tissue and another sensor is positioned proximate to normal tissue, and wherein said determining step comprises determining uptake in both normal and cancerous tissue.

30. A method according to claim 1, wherein said at least one sensor is implanted in solid tissue in the target region of interest and configured to operate wirelessly.

31. A method according to claim 1, wherein the radiolabeled test dose is is a radiolabeled version of a chemotherapeutic drug undergoing clinical evaluation, and wherein the determining step comprises generating a patient-specific time dependent response profile for determining whether the pharmaceutical product reaches the region of interest and/or the pharmacodynamics and/or pharmacokinetics thereof.

32. A method according to claim 1, wherein said monitoring step is carried out such that the radioactivity in the region of interest is monitored for a period of at least about 15 minutes, and wherein the determining step comprises predicting whether a therapeutic amount of the non-radiolabeled version of the chemotherapeutic agent is likely to be clinically effective for the particular subject based on said determining step and a priori data that defines at least one predetermined predictor variable associated with the uptake response.

33. A method according to claim 1, wherein said detecting step is at least periodically performed over a period of time extending for at least between about 0.25–24 hours.

34. A method according to claim 1, wherein said determining step identifies the biological ½ life of the test dose in the solid tissue.

35. A method according to claim 1, wherein said monitoring and/or determining steps determine the radiation activity in the solid tissue at a plurality of points in time and then determines at least one of the pharmacokinetic, the pharmacodynamic, and/or the biokinetic response to the radiolabeled test dose in solid tissue in the region of interest.

36. A method according to claim 1, wherein the radiolabeled test dose comprises a known anti-cancer chemotherapeutic drug with a priori data associating clinical efficacy to dose, retention and/or uptake of the anti-cancer drug at a tumor treatment site.

37. A method according to claim 1, wherein the determining the response profile comprises determining whether a tumor site is taking up and/or retaining the radiolabeled test dose.

38. A method according to claim 1, wherein the monitoring and determining are carried out to determine whether the radiation from the radiolabeled analyte exhibits a ½ life greater than about 15 minutes at a target localized tumor treatment site.

39. A method for predicting, on a patient-specific basis, a likelihood of response to a known chemotherapeutic agent in a tumor site of a respective patient, comprising:

chronically positioning at least one sensor in vivo in solid tissue proximate a tumor site in a patient's body;

administering a test dose of a C-14 radiolabeled chemotherapeutic agent;

detecting in vivo from the at least one sensor a signal over time corresponding to radiation proximate the tumor site in response to the administering step;

relaying the detected radiation signal to a location external of the patient's body;

determining a patient-specific in vivo uptake response of the C-14 radiolabeled test dose in solid tissue proximate the tumor site based on the relayed radiation signal; and determining whether to administer a therapeutic amount of a non-radiolabeled version of the chemotherapeutic agent based on the determined uptake response.

40. A method according to claim 39, wherein the determining step comprises comparing at least one predetermined predictor parameter associated with the uptake response in a patient-specific response profile to a corresponding at least one a priori predictor standard indicating the C-14 radiolabeled test dose is retained at or above a target level in the solid tissue proximate the tumor site for a target time.

41. A method according to claim 40, wherein the at least one predictor parameter comprises a C-14 half-life at the tumor site that is above about 15 minutes.

42. A method according to claim 39, the method further comprising administering the therapeutic dose amount of the non-radiolabeled chemotherapeutic agent to the patient if a favorable response is predicted by said determining whether to administer step.

43. A method according to claim 39, wherein the patient is a human, and wherein the determining whether to administer step comprises evaluating the patient uptake response to determine a likely treatment outcome of the corresponding therapeutic amount of the non-radiolabeled chemotherapeutic agent based on the monitored patient-specific uptake behavior of the radiolabeled test dose in the patient.

44. A method according to claim 39, wherein the administered C-14 labeled test dose of the chemotherapeutic agent comprises C-14 labeled glucose.

45. A method according to claim 39, wherein the administered C-14 labeled test dose of the chemotherapeutic agent comprises a C-14 labeled glucose derivative, wherein the glucose derivative is selected so that it has a modified glucose molecule chemical structure that is biocompatible and can be bio-chemically processed by the body.

46. A method according to claim 39, wherein the administered C-14 labeled test dose of the chemotherapeutic agent comprises C-14 labeled 2-deoxyglucose.

47. A method according to claim 39, wherein the administered C-14 labeled test dose of the chemotherapeutic agent comprises C-14 labeled dextraglucose.

48. A method according to claim 39, wherein the administered C-14 test dose comprises C-14 labeled 5-FU.

49. A method according to claim 39, wherein the administered C-14 test dose comprises a C-14 labeled antibody.

50. A method according to claim 39, wherein the determining step comprises generating a time-dependent patient uptake response profile.

* * * * *